(12) United States Patent
Fujita et al.

(10) Patent No.: US 6,387,547 B1
(45) Date of Patent: May 14, 2002

(54) COMPOUND FOR USE IN ORGANIC EL DEVICE AND ORGANIC EL DEVICE

(75) Inventors: Tetsuji Fujita; Tetsushi Inoue; Junji Aotani, all of Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 09/476,139

(22) Filed: Jan. 3, 2000

Related U.S. Application Data

(63) Continuation of application No. PCT/JP99/02334, filed on Apr. 30, 1999.

(30) Foreign Application Priority Data

May 1, 1998 (JP) ............................................. 10-137505

(51) Int. Cl.[7] ............................................. H05B 33/14
(52) U.S. Cl. ...................... 428/690; 428/917; 428/704; 313/504; 313/506; 252/301.16
(58) Field of Search ................................ 428/690, 917, 428/704; 313/504, 506; 252/301.16

(56) References Cited

FOREIGN PATENT DOCUMENTS

| JP | 61-85487 | 5/1986 |
| JP | 4-335087 | 11/1992 |
| JP | 6-167807 | 6/1994 |
| JP | 7-65958 | 3/1995 |
| JP | 8-231951 | 9/1996 |
| JP | 10-114890 | 5/1998 |
| JP | 10-289786 | 10/1998 |

OTHER PUBLICATIONS

J.A. Dodge, et al., The Journal of Organic Chemistry, vol. 55, No. 13, pp. 4190–4198, Regioselective Synthesis of Substituted Rubrenes, Jun. 22, 1990.

*Primary Examiner*—Cynthia H. Kelly
*Assistant Examiner*—Ling Xu
(74) *Attorney, Agent, or Firm*—Oblon, Spivak, McClelland, Maier & Neustadt, P.C.

(57) ABSTRACT

An object of the invention is to provide an organic EL device-forming compound and an organic EL device which produce light emission of satisfactory luminance, especially at long wavelength and are durable in that improved light emitting performance lasts for a long time. The object is attained by a compound having a basic skeleton represented by formula (I) and an organic EL device comprising the same.

(CF 55)

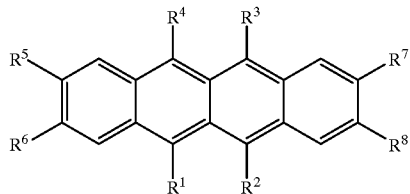

formula (I)

In formula (I), $R^1$, $R^2$, $R^3$, and $R^4$ each are a substituted or unsubstituted aryl or alkenyl group; $R^5$, $R^6$, $R^7$, and $R^8$ each are hydrogen; at least two of $R^1$ to $R^4$ are aryl groups which are at least bicyclic, aryl groups having aryl, amino, alkenyl, aryloxy or heterocyclic groups as substituents, or alkenyl groups, and when at least two substituents are monocyclic aryl groups, they further have substituents, and when the substituents are amino groups, at least two of $R^1$, $R^2$, $R^3$, and $R^4$ have substituted or unsubstituted aryl groups as substituents.

13 Claims, 10 Drawing Sheets

ILLUSTRATIVE COMPOUND I-85 MS SPECTRUM

FIG. 4 ILLUSTRATIVE COMPOUND I-85 IR SPECTRUM

ILLUSTRATIVE COMPOUND II-40 MS SPECTRUM

ILLUSTRATIVE COMPOUND II-40 NMR SPECTRUM

ILLUSTRATIVE COMPOUND III-38 MS SPECTRUM

ILLUSTRATIVE COMPOUND III-38 NMR SPECTRUM

ILLUSTRATIVE COMPOUND III-38 IR SPECTRUM

COMPOUND FOR USE IN ORGANIC EL DEVICE AND ORGANIC EL DEVICE

This application is a con PCT/JP99/02334 filed Apr. 30, 1999.

FIELD OF THE INVENTION

This invention relates to an organic electroluminescent (EL) device, and more particularly, to a compound for use in a device of the type wherein an electric field is applied across a thin film of an organic compound to emit light.

BACKGROUND ART

Organic electroluminescent (EL) devices include a thin film containing a luminescent organic compound interleaved between an electron injecting electrode and a hole injecting electrode. Electrons and holes are injected into the thin film where they are recombined to create excitons. Light is emitted by utilizing luminescence (phosphorescence or fluorescence) upon deactivation of excitons.

The organic EL devices are characterized by plane light emission at a high luminance of about 100 to 10,000 cd/m$^2$ with a voltage of about 10 volts and light emission in a spectrum from blue to red color by a simple choice of the type of fluorescent material.

Doping is one technique for producing light emission of any desired color from EL devices. It was reported in Jpn. J. Appl. Phys., 10, 527 (1971) to change emission color from blue to green by doping anthracene crystals with a minor level of tetracene. With respect to organic thin film EL devices having a multilayer structure, it was reported in JP-A 63-264692 to incorporate in a host material having a light emitting function a minor amount of a fluorescent dye capable of emitting light different from that of the host material in response to light emission from the host material as a dopant to form a light emitting layer, thereby changing the color of light emission from green to orange or red.

With respect to long wavelength light emission of yellow to red, known light emitting materials or dopant materials include laser dyes capable of red oscillation (EP 0281381), compounds capable of exciplex emission (JP-A 2-255788), perylene compounds (JP-A 3-791), coumarin compounds (JP-A 3-792), dicyanomethylene compounds (JP-A 3-162481), thioxanthene compounds (JP-A 3-177486), mixtures of a conjugated polymer and an electron transporting compound (JP-A 6-73374), squalirium compounds (JP-A 6-93257), oxadiazole compounds (JP-A 6-136359), oxynate derivatives (JP-A 6-145146), and pyrene compounds (JP-A 6240246).

Other light emitting materials disclosed heretofore include condensed polycyclic aromatic compounds (JP-A 5-32966 and 5-214334). Also dopant materials proposed heretofore include various condensed polycyclic aromatic compounds (JP-A 5-258859).

These light emitting systems, however, do not provide high luminance or stable light emitting performance, especially at long wavelength. A further improvement in luminance or durability is thus desired.

DISCLOSURE OF THE INVENTION

An object of the invention is to provide a compound for use in an organic EL device and an organic EL device which produce light emission of satisfactory luminance, especially at long wavelength and are durable in that improved light emitting performance lasts for a long time.

This and other objects of the invention are attained by the following construction.

(1) A compound for organic electroluminescent devices, having a basic skeleton represented by the following formula (I):

(CF 1)

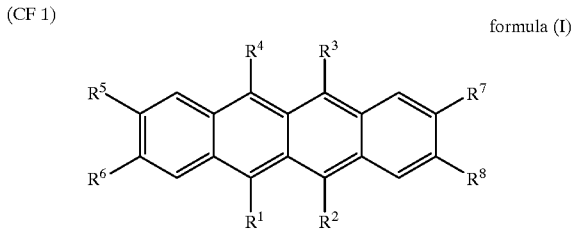

formula (I)

wherein $R^1$, $R^2$, $R^3$, and $R^4$ each are a substituted or unsubstituted aryl or alkenyl group; $R^5$, $R^6$, $R^7$, and $R^8$ each are hydrogen; at least two of $R^1$ to $R^4$ are aryl groups which are at least bicyclic, aryl groups having aryl, amino, alkenyl, aryloxy or heterocyclic groups as substituents, or alkenyl groups, and when at least two substituents are monocyclic aryl groups, they further have substituents, and when the substituents are amino groups, at least two of $R^1$, $R^2$, $R^3$, and $R^4$ have substituted or unsubstituted aryl groups as substituents.

(2) The compound for organic electroluminescent devices of (1), having a basic skeleton represented by the following formula (II):

(CF 2)

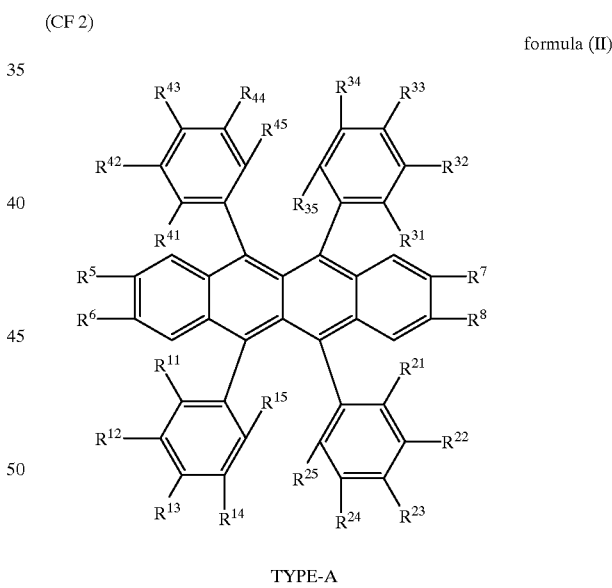

formula (II)

TYPE-A wherein each R group in sets of $R^{11}$ to $R^{15}$, $R^{21}$ to $R^{25}$, $R^{31}$ to $R^{35}$, and $R^{41}$ to $R^{45}$ is hydrogen or a substituted or unsubstituted alkyl, aryl, amino, heterocyclic or phenoxy group, the R groups in at least two sets have substituted or unsubstituted aryl, heterocyclic or aryloxy groups as substituents, or when the R groups are all hydrogen, at least two R groups in each of the sets of $R^{11}$ to $R^{15}$, $R^{23}$ to $R^{25}$, $R^{31}$ to $R^{35}$, and $R^{41}$ to $R^{45}$ form a fused ring.

(3) The compound for organic electroluminescent devices of (1), having a basic skeleton represented by the following formula (III):

(III)

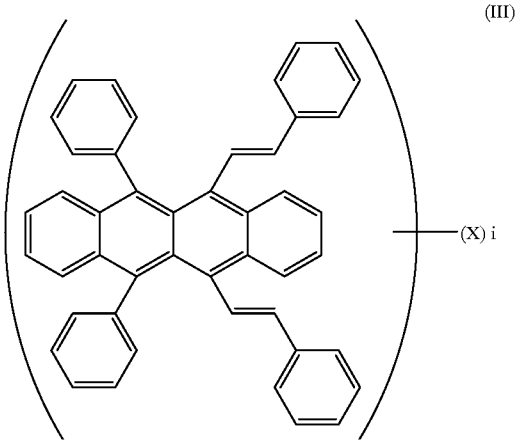

wherein X represents a substituent as defined for the substituents on $R^1$, $R^2$, $R^3$ and $R^4$, and i is an integer of 0 to 20.

(4) An organic electroluminescent device comprising a hole injecting electrode, an electron injecting electrode, and an organic layer disposed between the electrodes and including at least a light emitting layer, wherein said light emitting layer contains the compound set forth in any one of (1) to (3).

(5) The organic electroluminescent device of (4) wherein said light emitting layer further contains an electron injecting and transporting compound and/or a hole injecting and transporting compound.

(6) The organic electroluminescent device of (4) or (5) wherein said light emitting layer contains at least two compounds.

(7) The organic electroluminescent device of (4) or (6) wherein said light emitting layer contains at least two dopants, the content of the dopants combined being up to 30% by weight based on a host material.

(8) The organic electroluminescent device of any one of (4) to (7) wherein the overall content of the compound of (1) in said light emitting layer is up to 30% by weight based on a host material.

(9) The organic electroluminescent device of (7) or (8) wherein said light emitting layer contains at least two compounds having different carrier trapping capabilities.

(10) The organic electroluminescent device of any one of (7) to (9) wherein said light emitting layer contains at least a compound having a hole trapping capability and a compound having an electron trapping capability.

(11) The organic electroluminescent device of any one of (4) to (10) wherein at least two light emitting layers are included, and said light emitting layers contain dopants having different carrier trapping capabilities.

(12) The organic electroluminescent device of any one of (4) to (11) wherein at least two light emitting layers are included, at least one layer of said light emitting layers contains a dopant having a hole trapping capability, and at least one other layer of said light emitting layers contains a dopant having an electron trapping capability.

(13) An organic electroluminescent device comprising a hole injecting electrode, an electron injecting electrode, and an organic layer disposed between the electrodes and including at least a light emitting layer, wherein said light emitting layer contains at least two organic electroluminescent device-forming compounds having different carrier trapping capabilities, each said compound having a basic skeleton represented by the following formula (IV):

(IV)

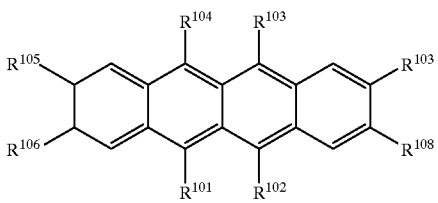

wherein $R^{101}$, $R^{102}$, $R^{103}$, and $R^{104}$ each are hydrogen or a substituted or unsubstituted aryl or alkenyl group, excluding the case where at least three R's are hydrogen atoms; $R^{105}$, $R^{106}$, $R^{107}$, and $R^{108}$ each are hydrogen or a substituted or unsubstituted aryl or alkenyl group; at least two of $R^{101}$ to $R^{104}$ are aryl groups which are at least bicyclic or alkenyl groups, or have alkyl, aryl, amino, alkenyl, aryloxy or heterocyclic groups as substituents.

BEST MODE FOR CARRYING OUT THE INVENTION

Figure 1:
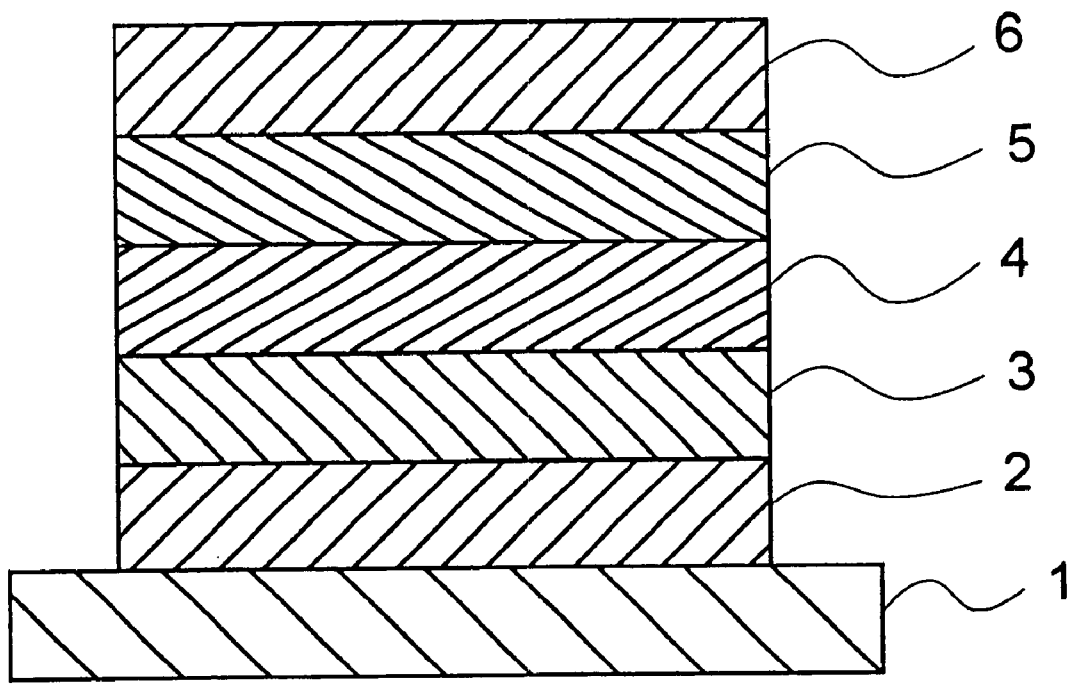
FIG. 1 is a schematic cross-sectional view showing the basic construction of an organic EL device according to the invention.

The compounds of the present invention have a basic skeleton represented by the following formula (I).

formula (I)

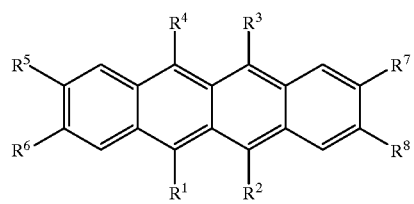

By incorporating a compound of formula (I) in a light emitting layer, there is obtained an organic EL device capable of light emission having a maximum wavelength in the long wavelength range. Particularly when the compound of formula (I) is used in the light emitting layer as a dopant for a host material having a light emitting function in itself or as a dopant in a mix layer with a light emitting function formed from a mixture of an electron injecting and transporting compound and a hole injecting and transporting compound, light emission of blue to red, especially long wavelength light emission is possible at a sufficient luminance and the light emitting performance lasts long.

In formula (I), $R^1$, $R^2$, $R^3$, and $R^4$ each are a substituted or unsubstituted aryl or alkenyl group. $R^5$, $R^6$, $R^7$, and $R^8$ each are hydrogen. At least two of $R^1$ to $R^4$ are aryl groups which are at least bicyclic, aryl groups having aryl, amino, alkenyl, aryloxy or heterocyclic groups as substituents, or alkenyl groups. When at least two substituents are monocyclic aryl groups, they further have substituents. Also, when the substituents are amino groups, at least two of $R^1$, $R^2$, $R^3$, and $R^4$ have substituted or unsubstituted aryl groups as substituents.

The aryl groups represented by $R^1$ to $R^4$ may be monocyclic or polycyclic, inclusive of fused rings and a collection of rings. Those aryl groups having 6 to 30 carbon atoms in total are preferred and they may have substituents. When the aryl groups are monocyclic, it is preferable that at least three of them have aryl groups substituted thereon, which in turn, preferably have aryl groups as substituents.

The alkenyl groups represented by $R^1$ to $R^4$ are preferably those having a phenyl group as at least one substituent, such as 1- and 2-phenylalkenyl, 1,2- and 2,2-diphenylalkenyl, and 1,2,2-triphenylalkenyl, although unsubstituted alkenyl groups are acceptable.

Where $R^1$ to $R^4$ have substituents thereon, it is preferable that at least two of these substituents are selected from among aryl, amino, heterocyclic, alkenyl and aryloxy groups. The aryl, amino, heterocyclic and alkenyl groups are as defined above for $R^1$ to $R^4$.

The aryl groups to substitute on $R^1$ to $R^4$ are preferably phenyl, o-, m- or p-tolyl, pyrenyl, perylenyl, coronenyl, 1- or 2-naphthyl, anthryl, o-, m- or biphenylyl, terphenyl and phenanthryl groups.

The amino groups to substitute on $R^1$ to $R^4$ may be selected from among alkylamino, arylamino, aralkylamino and analogous groups. They preferably have aliphatic groups having 1 to 6 carbon atoms in total and/or aromatic carbocyclic groups having 1 to 4 rings. Illustrative examples include dimethylamino, diethylamino, dibutylamino, diphenylamino, ditolylamino, bisdiphenylylamino, and bisnaphthylamino groups.

The heterocyclic groups to substitute on $R^1$ to $R^4$ include 5- or 6-membered ring aromatic heterocyclic groups containing O, N or S as a hetero atom, and fused polycyclic aromatic heterocyclic groups having 2 to 20 carbon atoms.

Examples of the aromatic heterocyclic groups and fused polycyclic aromatic heterocyclic groups include thienyl, furyl, pyrolyl, pyridyl, quinolyl, and quinoxalyl groups.

The aryloxy groups to substitute on $R^1$ to $R^4$ are preferably those of aryl groups having 6 to 18 carbon atoms in total, for example, o-, m- and p-phenoxy.

At least two of these substituents may form a fused ring. Also, these substituents may be further substituted ones, in which preferred substituents are as described above.

When $R^1$ to $R^4$ have substituents, it is preferred that at least two of the substituents have the above-described substituents. The position of substitution is not particularly limited and may be a meta, para or ortho position. $R^1$ and $R^4$, and $R^2$ and $R^3$ in the respective pairs are preferably identical although they may be different. Also preferably, when the substituents are aryl groups, they have further substituents thereon.

$R^5$, $R^6$, $R^7$, and $R^8$ each are hydrogen.

Further preferably, the compounds for organic electroluminescent devices according to the invention are those having a basic skeleton represented by the following formula (II):
(CF 10)

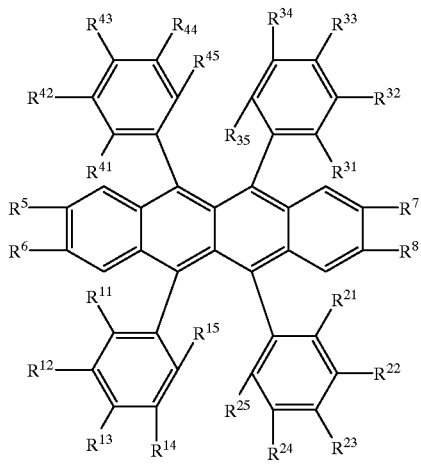

formula (II)

TYPE-A

In formula (II), each R group in sets of $R^{11}$ to $R^{15}$, $R^{21}$ to $R^{25}$, $R^{31}$ to $R^{35}$, and $R^{41}$ to $R^{45}$ is hydrogen or a substituted or unsubstituted alkyl, aryl, amino, heterocyclic or phenoxy group. The R groups in at least two sets have substituted or unsubstituted aryl, heterocyclic or aryloxy groups as substituents, or when these R groups are all hydrogen, at least two R groups in each of the sets of $R^{11}$ to $R^{15}$, $R^{21}$ to $R^{25}$, $R^{31}$ to $R^{35}$, and $R^{41}$ to $R^{45}$ form a fused ring.

Preferred examples of the aryl, amino, heterocyclic and aryloxy groups are the same as exemplified above for $R^1$ to $R^4$. It is preferred that $R^{11}$ to $R^{15}$, $R^{21}$ to $R^{25}$, $R^{31}$ to $R^{35}$, and $R^{41}$ to $R^{45}$ in the respective sets are identical although they may be different.

The amino groups to substitute on $R^{11}$ to $R^{15}$, $R^{21}$ to $R^{25}$, $R^{31}$ to $R^{35}$, and $R^{41}$ to $R^{45}$ may be alkylamino, arylamino, aralkylamino and analogous groups. They preferably have aliphatic groups with 1 to 6 carbon atoms in total and/or aromatic carbocyclic groups of 1 to 4 rings. Illustrative examples are dimethylamino, diethylamino, dibutylamino, diphenylamino, ditolylamino, and bisbiphenylylamino groups.

Examples of the fused ring formed include indene, naphthalene, anthracene, phenanthrene, quinoline, isoquinoline, quinoxaline, phenazine, acridine, indole, carbazole, phenoxazine, phenothiazine, benzothiazole, benzothiophene, benzofuran, acridone, benzimidazole, coumarin, and flavone.

Further the compound of the invention may have the following basic skeleton.

(CF 11)

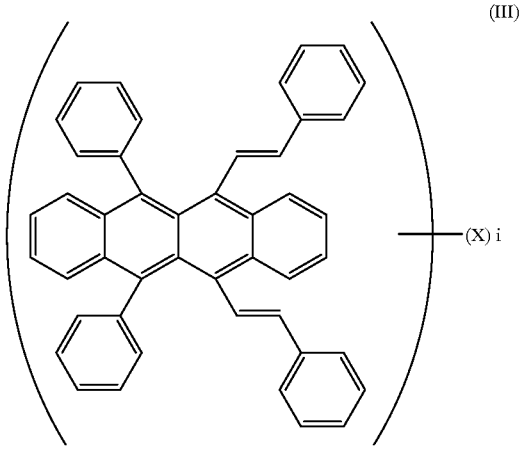

In formula (III), X represents a substituent as defined for the substituents on $R^1$, $R^2$, $R^3$ and $R^4$, and i is an integer of 0 to 20, preferably 0 to 10, more preferably 2 to 10, and most preferably 2 to 4.

Especially preferred illustrative examples of the compound of the invention are shown below in Tables 1 to 33. The substituents $R^1$ to $R^8$ are represented by $R^{10}$ to $R^{80}$, respectively.

TABLE 1

| Compound No. | $R^{10}$ | $R^{20}$ | $R^{30}$ | $R^{40}$ | $R^{50}$ | $R^{60}$ | $R^{70}$ | $R^{80}$ |
|---|---|---|---|---|---|---|---|---|
| 1-4 | phenyl | terphenyl | terphenyl | phenyl | H | H | H | H |
| 1-5 | phenyl | terphenyl | terphenyl | phenyl | H | H | H | H |
| 1-7 | phenyl | tetraphenyl-substituted phenyl | tetraphenyl-substituted phenyl | phenyl | H | H | H | H |
| 1-8 | phenyl | tetraphenyl-substituted phenyl | tetraphenyl-substituted phenyl | phenyl | H | H | H | H |

TABLE 1-continued
| Compound No. | R^{10} | R^{20} | R^{30} | R^{40} | R^{50} | R^{60} | R^{70} | R^{80} |
|---|---|---|---|---|---|---|---|---|
| 1-10 | 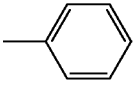 | 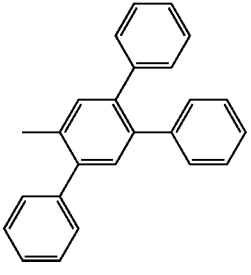 | 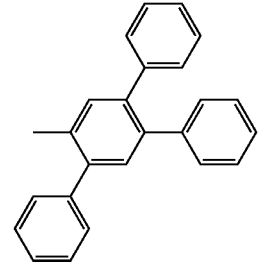 | 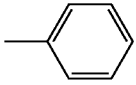 | H | H | H | H |
| 1-11 | 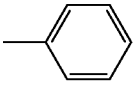 | 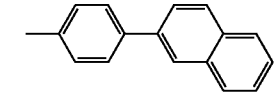 | 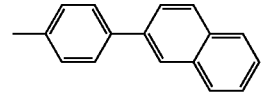 | 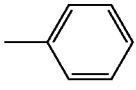 | H | H | H | H |
| 1-14 | 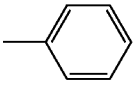 | 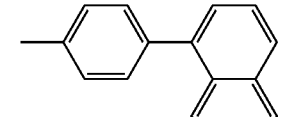 | 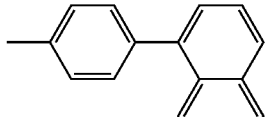 | 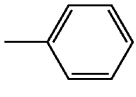 | H | H | H | H |
TABLE 2
| Compound No. | R^{10} | R^{20} | R^{30} |
|---|---|---|---|
| I-17 | 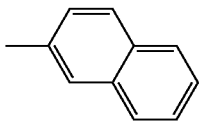 | 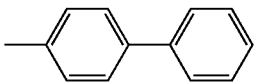 | 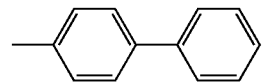 |
| I-18 | 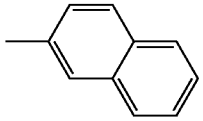 | 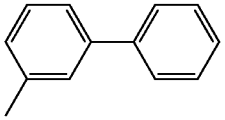 | 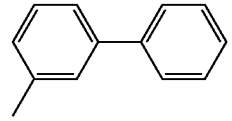 |
| I-20 | 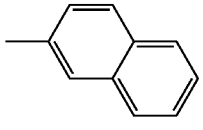 | 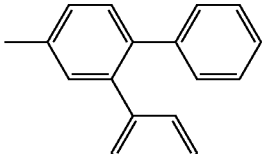 | 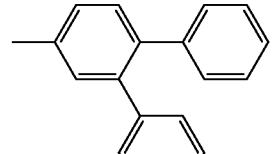 |
| I-21 | 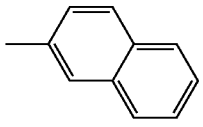 | 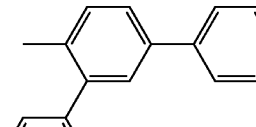 | 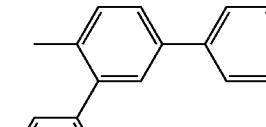 |

TABLE 2-continued

| | Substituent |
|---|---|
| I-23 | [naphthyl] [phenyl-substituted benzene with three phenyls] [phenyl-substituted benzene with three phenyls] |
| I-24 | [naphthyl] [phenyl-substituted benzene with three phenyls] [phenyl-substituted benzene with three phenyls] |

| Compound No. | $R^{40}$ | $R^{50}$ | $R^{60}$ | $R^{70}$ | $R^{80}$ |
|---|---|---|---|---|---|
| I-17 | [2-naphthyl] | H | H | H | H |
| I-18 | [2-naphthyl] | H | H | H | H |
| I-20 | [2-naphthyl] | H | H | H | H |
| I-21 | [2-naphthyl] | H | H | H | H |
| I-23 | [2-naphthyl] | H | H | H | H |
| I-24 | [2-naphthyl] | H | H | H | H |

TABLE 3

| Compound No. | R¹⁰ | R²⁰ | R³⁰ |
|---|---|---|---|
| I-26 | 2-naphthyl | 2,4,5-triphenylphenyl | 2,4,5-triphenylphenyl |
| I-27 | 2-naphthyl | 4-(2-naphthyl)phenyl | 4-(2-naphthyl)phenyl |
| I-30 | 2-naphthyl | 4-(1-naphthyl)phenyl | 4-(1-naphthyl)phenyl |

| Compound No. | R⁴⁰ | R⁵⁰ | R⁶⁰ | R⁷⁰ | R⁸⁰ |
|---|---|---|---|---|---|
| I-26 | 2-naphthyl | H | H | H | H |
| I-27 | 2-naphthyl | H | H | H | H |
| I-30 | 2-naphthyl | H | H | H | H |

TABLE 4

| Compound No. | R¹⁰ | R²⁰ | R³⁰ |
|---|---|---|---|
| I-33 | 4-biphenyl | 4-biphenyl | 4-biphenyl |
| I-34 | 4-biphenyl | 3-biphenyl | 3-biphenyl |

TABLE 4-continued
Substituent
I-35 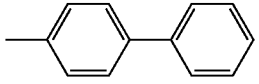 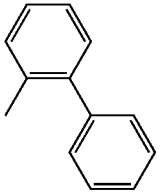 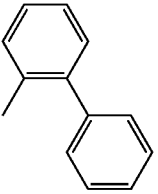
I-36 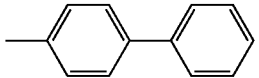 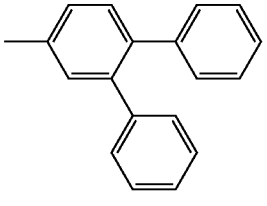 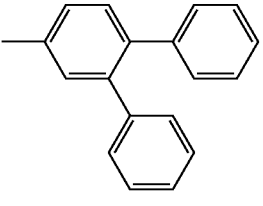
I-37 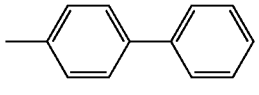 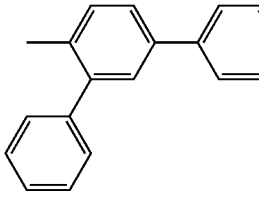 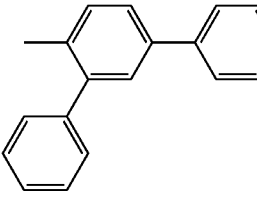
I-38 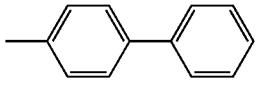 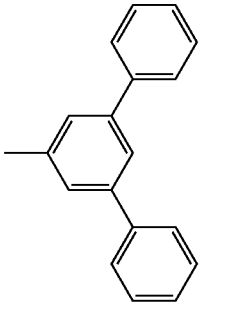 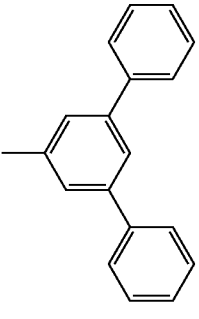
I-39 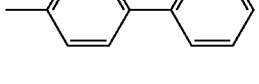 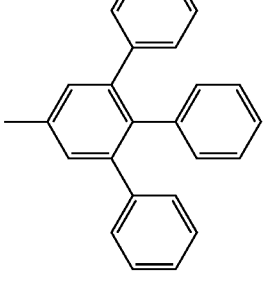 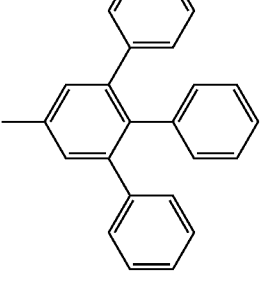
I-40 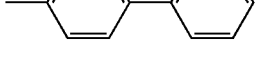 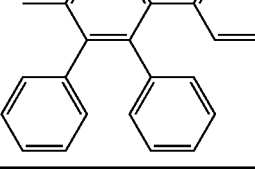 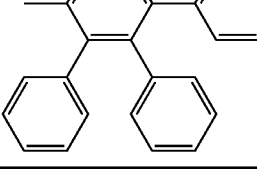

TABLE 4-continued
| Compound No. | R40 | R50 | R60 | R70 | R80 |
|---|---|---|---|---|---|
| I-33 | 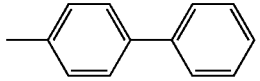 | H | H | H | H |
| I-34 | 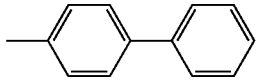 | H | H | H | H |
| I-35 | 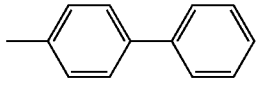 | H | H | H | H |
| I-36 | 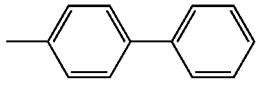 | H | H | H | H |
| I-37 | 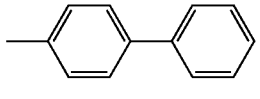 | H | H | H | H |
| I-38 | 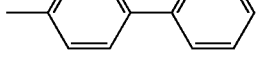 | H | H | H | H |
| I-39 | 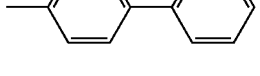 | H | H | H | H |
| I-40 | 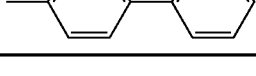 | H | H | H | H |
TABLE 5
| Compound No. | R10 | R20 | R30 |
|---|---|---|---|
| I-41 | 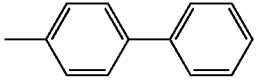 | 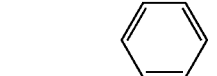 |  |

TABLE 5-continued
| | Substituent | | |
|---|---|---|---|
| I-42 | 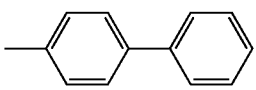 | 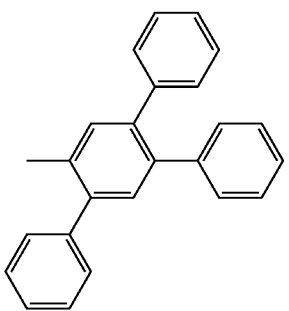 | 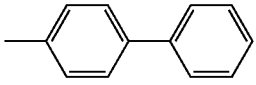 |
| I-43 | 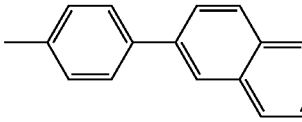 | | |
| I-44 | 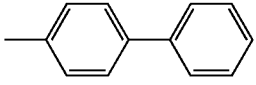 | | |
| I-45 | 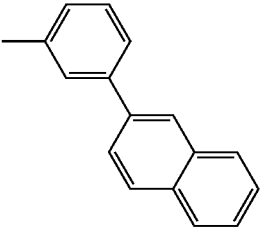 | | |
| I-46 | 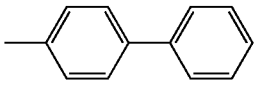 | | |
| I-47 | 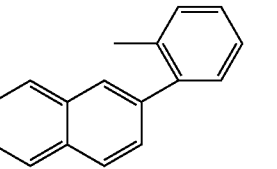 | | |
| I-48 | 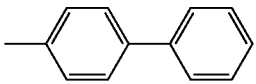 | | |

TABLE 5-continued

| | Substituent | | | | | |
|---|---|---|---|---|---|---|
| Compound No. | R⁴⁰ | R⁵⁰ | R⁶⁰ | R⁷⁰ | R⁸⁰ |
| I-41 | —[biphenyl] | H | H | H | H |
| I-42 | —[biphenyl] | H | H | H | H |
| I-43 | —[biphenyl] | H | H | H | H |
| I-44 | —[biphenyl] | H | H | H | H |
| I-45 | —[biphenyl] | H | H | H | H |
| I-46 | —[biphenyl] | H | H | H | H |
| I-47 | —[biphenyl] | H | H | H | H |
| I-48 | —[biphenyl] | H | H | H | H |

TABLE 6

| | Substituent | | |
|---|---|---|---|
| Compound No. | R¹⁰ | R²⁰ | R³⁰ |
| I-49 | —[phenyl] | —[phenyl-anthracenyl] | —[phenyl-anthracenyl] |
| I-52 | —[phenyl] | —[phenyl-anthracenyl] | —[phenyl-anthracenyl] |

TABLE 6-continued

| | Substituent | | |
|---|---|---|---|
| I-55 | [phenyl] | [p-tolyl-9-anthracenyl] | [p-tolyl-9-anthracenyl] |
| I-61 | [2-naphthyl] | [p-phenyl-2-anthracenyl] | [p-phenyl-2-anthracenyl] |
| I-64 | [2-naphthyl] | [p-phenyl-1-anthracenyl] | [p-phenyl-1-anthracenyl] |
| I-67 | [2-naphthyl] | [p-tolyl-9-anthracenyl] | [p-tolyl-9-anthracenyl] |

| Compound No. | $R^{40}$ | $R^{50}$ | $R^{60}$ | $R^{70}$ | $R^{80}$ |
|---|---|---|---|---|---|
| I-49 | [phenyl] | H | H | H | H |
| I-52 | [phenyl] | H | H | H | H |
| I-55 | [phenyl] | H | H | H | H |
| I-61 | [2-naphthyl] | H | H | H | H |
| I-64 | [2-naphthyl] | H | H | H | H |

TABLE 6-continued
| | Substituent | | | | | |
|---|---|---|---|---|---|---|
| I-67 | 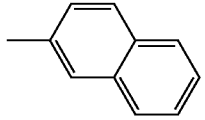 | H | H | H | H | |
TABLE 7
| | Substituent | | |
|---|---|---|---|
| Compound No. | $R^{10}$ | $R^{20}$ | $R^{30}$ |
| I-73 | 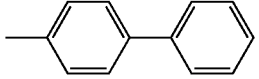 | 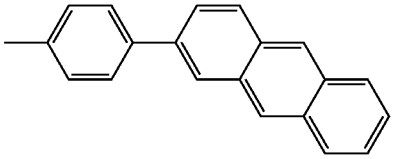 | 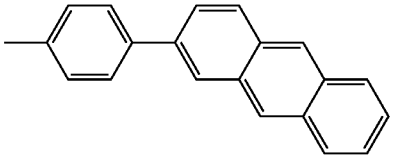 |
| I-74 | 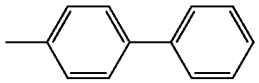 | 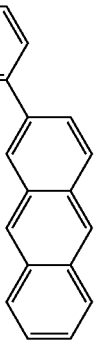 | 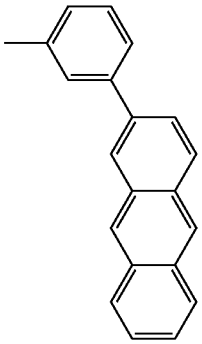 |
| I-75 | 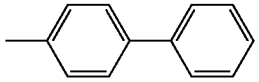 | 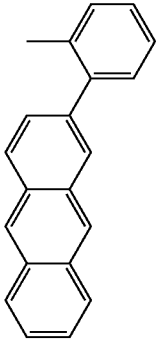 | 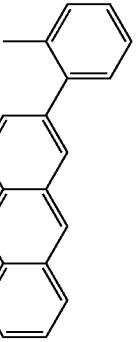 |
| I-76 | 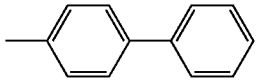 | 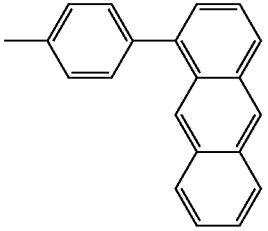 | 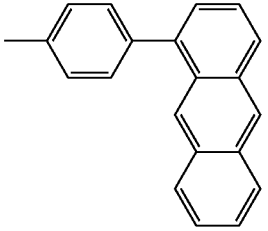 |

TABLE 7-continued

| | Substituent | | |
|---|---|---|---|
| I-77 | [4-methylbiphenyl group] | [3-(anthracen-1-yl)tolyl group] | [3-(anthracen-1-yl)tolyl group] |
| I-78 | [4-methylbiphenyl group] | [2-(anthracen-1-yl)tolyl group] | [2-(anthracen-1-yl)tolyl group] |
| I-79 | [4-methylbiphenyl group] | [10-(4-methylphenyl)anthracen-9-yl group] | [10-(4-methylphenyl)anthracen-9-yl group] |

| Compound No. | $R^{40}$ | $R^{50}$ | $R^{60}$ | $R^{70}$ | $R^{80}$ |
|---|---|---|---|---|---|
| I-73 | [4-methylbiphenyl] | H | H | H | H |
| I-74 | [4-methylbiphenyl] | H | H | H | H |
| I-75 | [4-methylbiphenyl] | H | H | H | H |
| I-76 | [4-methylbiphenyl] | H | H | H | H |
| I-77 | [4-methylbiphenyl] | H | H | H | H |
| I-78 | [4-methylbiphenyl] | H | H | H | H |
| I-79 | [4-methylbiphenyl] | H | H | H | H |

TABLE 8
| Compound No. | R¹⁰ | R²⁰ | R³⁰ |
|---|---|---|---|
| I-80 | 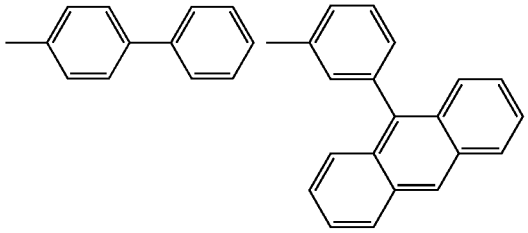 | 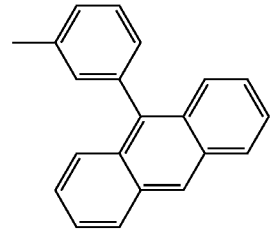 | 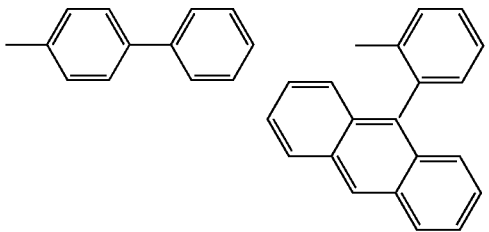 |
| I-81 | 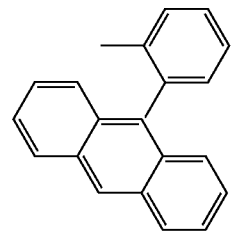 | 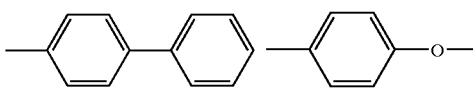 | 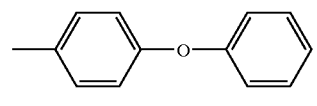 |
| I-82 | 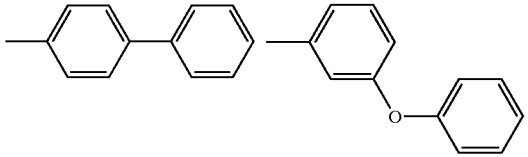 | 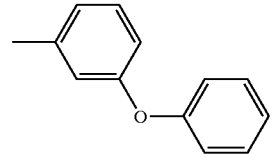 | 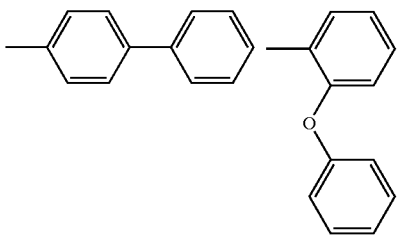 |
| I-83 | 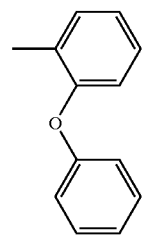 | 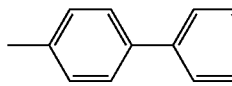 | 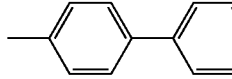 |
| I-84 | 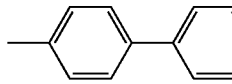 | 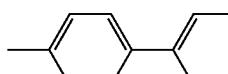 | |
| Compound No. | R⁴⁰ | R⁵⁰ | R⁶⁰ | R⁷⁰ | R⁸⁰ |
|---|---|---|---|---|---|
| I-80 | | H | H | H | H |
| I-81 | | H | H | H | H |
| I-82 | | H | H | H | H |
| I-83 | | H | H | H | H |

TABLE 8-continued
| | Substituent | | | | |
|---|---|---|---|---|---|
| I-84 | 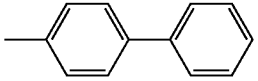 | H | H | H | H |
TABLE 9
| | Substituent | | |
|---|---|---|---|
| Compound No. | $R^{10}$ | $R^{20}$ | $R^{30}$ |
| I-90 | 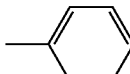 | 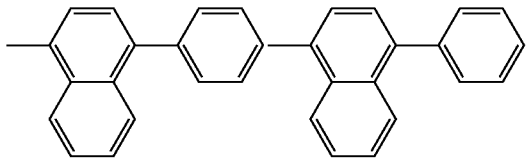 | |
| I-105 | 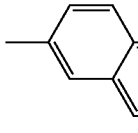 | 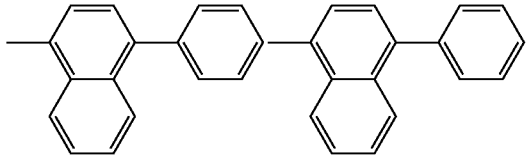 | |
| Compound No. | $R^{40}$ | $R^{50}$ | $R^{60}$ | $R^{70}$ | $R^{80}$ |
|---|---|---|---|---|---|
| I-90 | 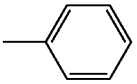 | H | H | H | H |
| I-105 | 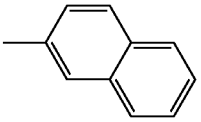 | H | H | H | H |
TABLE 10
| | Substituent | | |
|---|---|---|---|
| Compound No. | $R^{10}$ | $R^{20}$ | $R^{30}$ |
| I-115 | 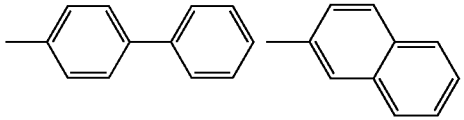 | 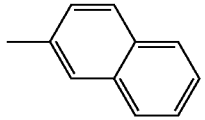 | 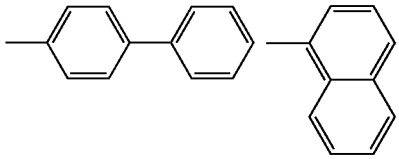 |
| I-116 | 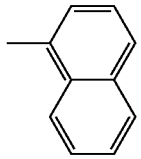 | | |

TABLE 10-continued

| Compound No. | R⁴⁰ | R⁵⁰ | R⁶⁰ | R⁷⁰ | R⁸⁰ |
|---|---|---|---|---|---|
| I-115 | [4-phenylphenyl] | H | H | H | H |
| I-116 | [4-phenylphenyl] | H | H | H | H |
| I-117 | [4-phenylphenyl] | H | H | H | H |

TABLE 10-continued
| | | Substituent | | | | |
|---|---|---|---|---|---|---|
| | I-118 | 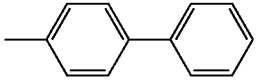 | H | H | H | H |
| | I-119 | 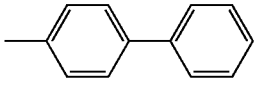 | H | H | H | H |
| | I-120 | 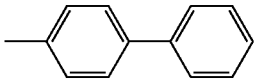 | H | H | H | H |
| | I-121 | 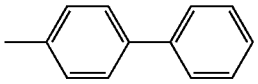 | H | H | H | H |
| | I-122 | 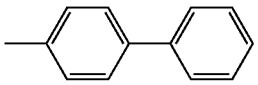 | H | H | H | H |
TABLE 11
| | Substituent | | |
|---|---|---|---|
| Compound No. | $R^{10}$ | $R^{20}$ | $R^{30}$ |
| I-123 | 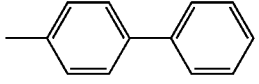 | 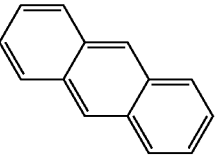 | 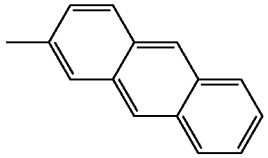 |
| I-124 | 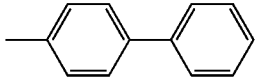 |  | 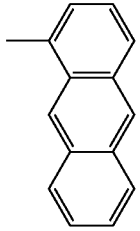 |
| I-125 | 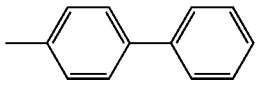 | 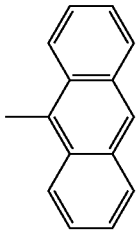 | 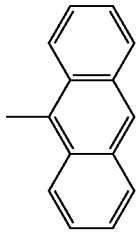 |

TABLE 11-continued

| Compound No. | R⁴⁰ | R⁵⁰ | R⁶⁰ | R⁷⁰ | R⁸⁰ |
|---|---|---|---|---|---|
| I-123 | [4-biphenyl] | H | H | H | H |
| I-124 | [4-biphenyl] | H | H | H | H |
| I-125 | [4-biphenyl] | H | H | H | H |
| I-126 | [4-biphenyl] | H | H | H | H |
| I-127 | [4-biphenyl] | H | H | H | H |
| I-128 | [4-biphenyl] | H | H | H | H |

TABLE 11-continued
| | Substituent | | | | |
|---|---|---|---|---|---|
| I-129 | 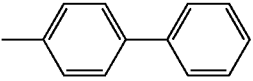 | H | H | H | H |
TABLE 12
| | Substituent | | |
|---|---|---|---|
| Compound No. | $R^{10}$ | $R^{20}$ | $R^{30}$ |
| I-130 | 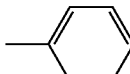 | 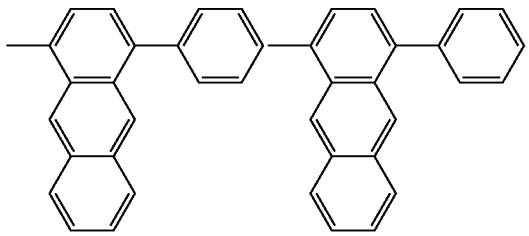 | |
| I-135 | 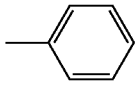 | 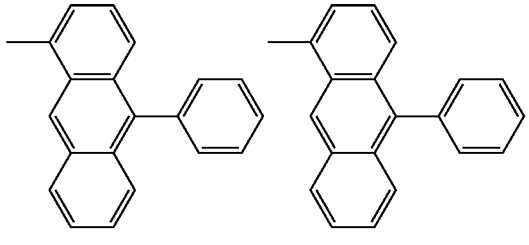 | |
| I-137 | 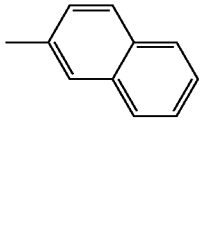 | 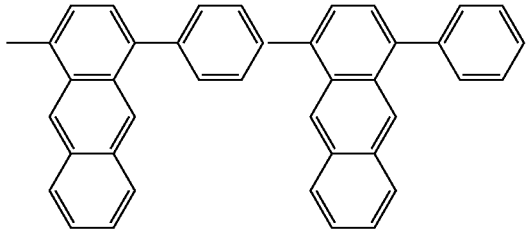 | |
| I-142 | 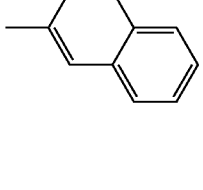 | 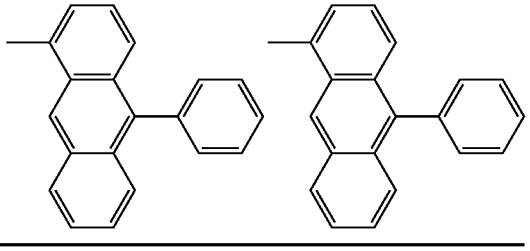 | |
| Compound No. | $R^{40}$ | $R^{50}$ | $R^{60}$ | $R^{70}$ | $R^{80}$ |
|---|---|---|---|---|---|
| I-130 | 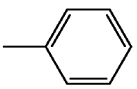 | H | H | H | H |
| I-135 | 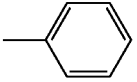 | H | H | H | H |

TABLE 12-continued
| | Substituent | | | | | |
|---|---|---|---|---|---|---|
| I-137 | 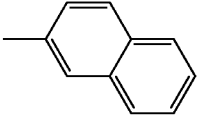 | H | H | H | H | |
| I-142 | 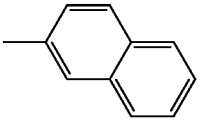 | H | H | H | H | |
TABLE 13
| | Substituent | | |
|---|---|---|---|
| Compound No. | $R^{10}$ | $R^{20}$ | $R^{30}$ |
| I-144 | 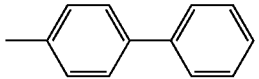 | 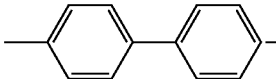 | 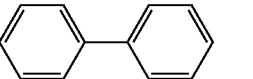 |
| I-145 | 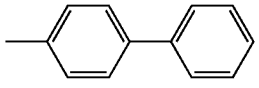 | 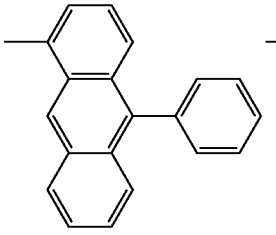 | 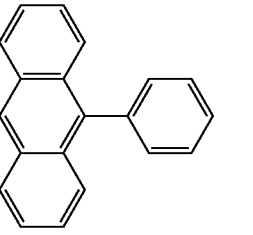 |
| I-146 | 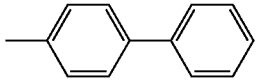 | 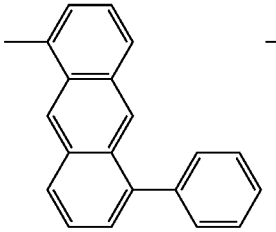 | 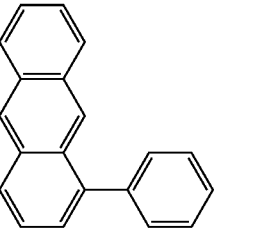 |
| I-147 | 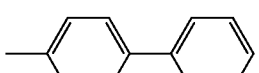 | 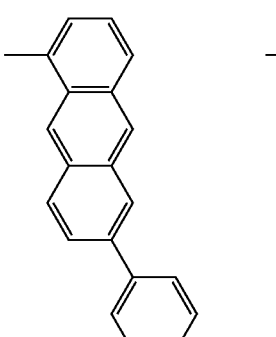 | 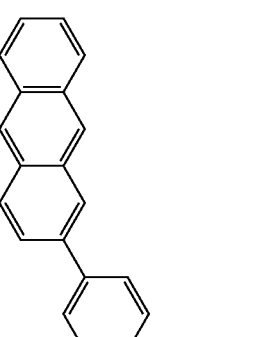 |

TABLE 13-continued

| Substituent | | | |
|---|---|---|---|
| I-148 | [structure] | [structure] | [structure] |
| I-149 | [structure] | [structure] | [structure] |
| I-150 | [structure] | [structure] | [structure] |

| Compound No. | $R^{40}$ | $R^{50}$ | $R^{60}$ | $R^{70}$ | $R^{80}$ |
|---|---|---|---|---|---|
| I-144 | [structure] | H | H | H | H |
| I-145 | [structure] | H | H | H | H |
| I-146 | [structure] | H | H | H | H |
| I-147 | [structure] | H | H | H | H |
| I-148 | [structure] | H | H | H | H |
| I-149 | [structure] | H | H | H | H |

TABLE 13-continued
| | Substituent | | | | |
|---|---|---|---|---|---|
| I-150 | 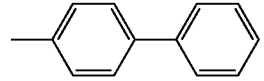 | H | H | H | H |
TABLE 14
| | Substituent | | | | | | | |
|---|---|---|---|---|---|---|---|---|
| Compound No. | $R^{10}$ | $R^{20}$ | $R^{30}$ | $R^{40}$ | $R^{50}$ | $R^{60}$ | $R^{70}$ | $R^{80}$ |
| I-199 | 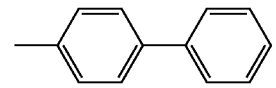 | 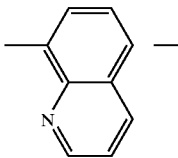 | 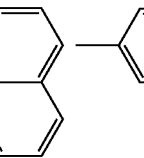 | 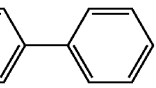 | H | H | H | H |
| I-200 | 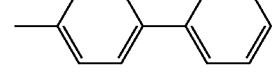 | 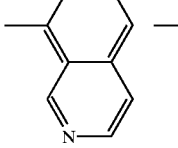 | 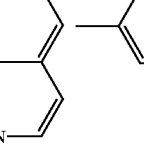 | 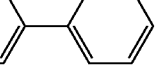 | H | H | H | H |
| I-201 | 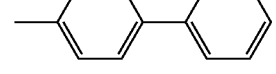 | 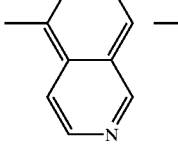 | 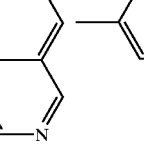 | 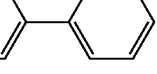 | H | H | H | H |
| I-202 | 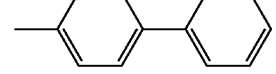 | 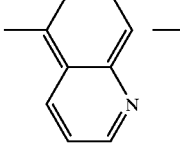 | 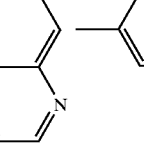 | 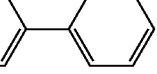 | H | H | H | H |
| I-203 | 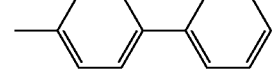 | 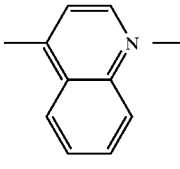 | 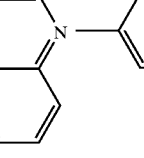 | 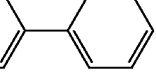 | H | H | H | H |
| I-204 | 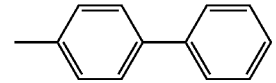 | 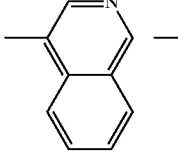 | 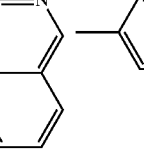 | 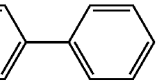 | H | H | H | H |
| I-205 | 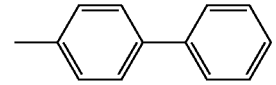 | 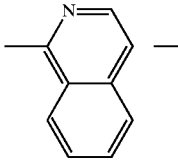 | 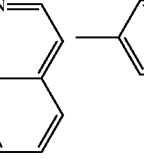 | 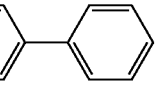 | H | H | H | H |

TABLE 14-continued
| Compound No. | Substituent | | | | | | | |
|---|---|---|---|---|---|---|---|---|
| | R$^{10}$ | R$^{20}$ | R$^{30}$ | R$^{40}$ | R$^{50}$ | R$^{60}$ | R$^{70}$ | R$^{80}$ |
| I-206 | 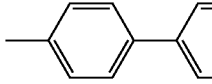 | 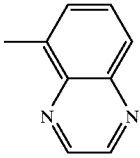 | 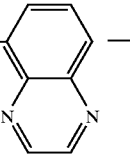 | 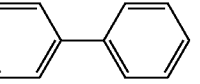 | H | H | H | H |
TABLE 15
| Compound No. | Substituent | | |
|---|---|---|---|
| | R$^{10}$ | R$^{20}$ | R$^{30}$ |
| I-207 | 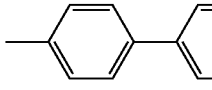 | 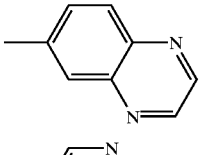 | 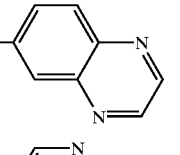 |
| I-208 | 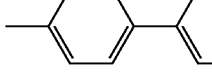 | 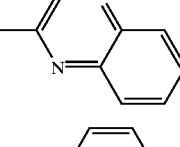 | 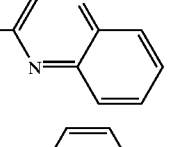 |
| I-209 | 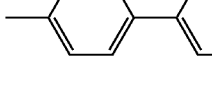 | 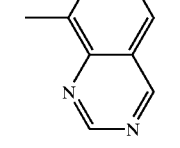 | 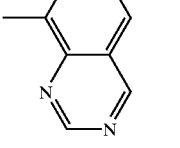 |
| I-210 | 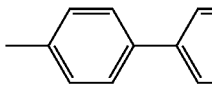 | 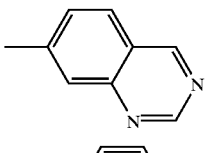 | 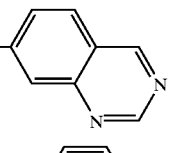 |
| I-211 | 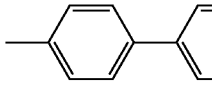 | 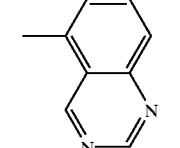 | 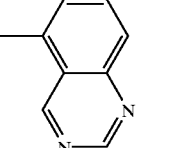 |
| I-212 | 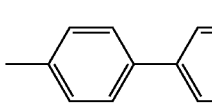 | 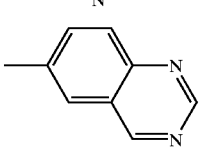 | 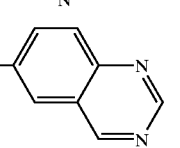 |
| I-213 | 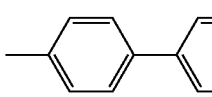 | 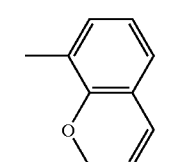 | 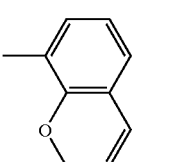 |

TABLE 15-continued

| Compound No. | Substituent | | | | |
|---|---|---|---|---|---|
| | R⁴⁰ | R⁵⁰ | R⁶⁰ | R⁷⁰ | R⁸⁰ |
| I-214 | [biphenyl-coumarin-coumarin structure] | | | | |
| I-207 | [biphenyl group] | H | H | H | H |
| I-208 | [biphenyl group] | H | H | H | H |
| I-209 | [biphenyl group] | H | H | H | H |
| I-210 | [biphenyl group] | H | H | H | H |
| I-211 | [biphenyl group] | H | H | H | H |
| I-212 | [biphenyl group] | H | H | H | H |
| I-213 | [biphenyl group] | H | H | H | H |
| I-214 | [biphenyl group] | H | H | H | H |

TABLE 16

| Compound No. | Substituent | | |
|---|---|---|---|
| | R¹⁰ | R²⁰ | R³⁰ |
| I-215 | [biphenyl group] | [coumarin group] | [coumarin group] |
| I-216 | [biphenyl group] | [coumarin group] | [coumarin group] |

TABLE 16-continued

| Compound No. | Substituent | | | | |
|---|---|---|---|---|---|
| | $R^{40}$ | $R^{50}$ | $R^{60}$ | $R^{70}$ | $R^{80}$ |
| I-215 | (biphenyl structure) | H | H | H | H |
| I-216 | (biphenyl structure) | H | H | H | H |

TABLE 16-continued
| | | | | | | |
|---|---|---|---|---|---|---|
| I-217 | 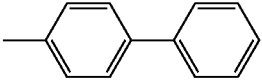 | H | H | H | H | |
| I-218 | 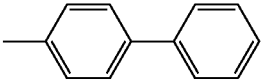 | H | H | H | H | |
| I-219 | 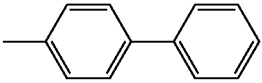 | H | H | H | H | |
| I-220 | 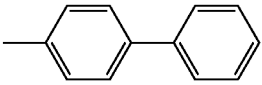 | H | H | H | H | |
| I-221 | 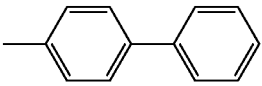 | H | H | H | H | |
| I-222 | 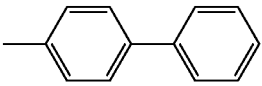 | H | H | H | H | |

TABLE 17
| Compound No. | R$^{10}$ | R$^{20}$ | R$^{30}$ |
|---|---|---|---|
| I-223 | 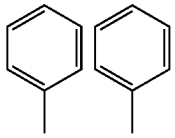 |  | 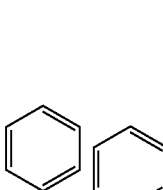 |
| I-224 | 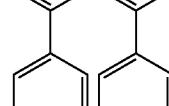 |  | 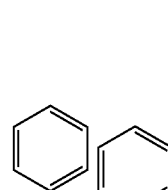 |
| I-225 | 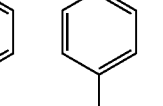 |  | 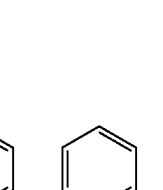 |
| I-226 | 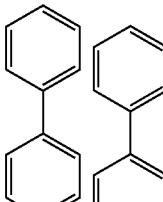 | 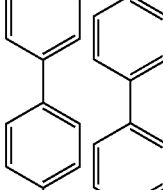 | 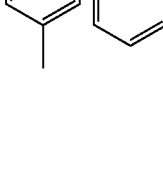 |
| I-227 | 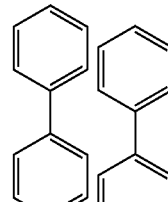 | 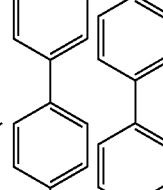 | 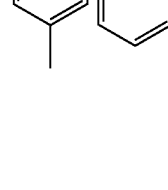 |
| I-228 | 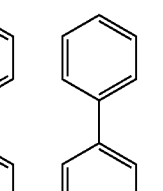 | 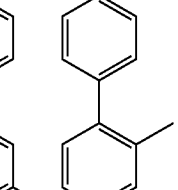 | 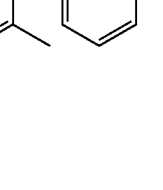 |
| I-229 | 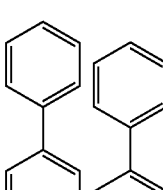 | 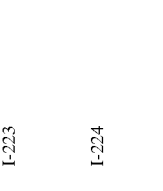 | 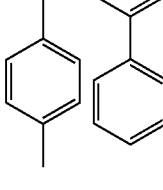 |
| I-230 | 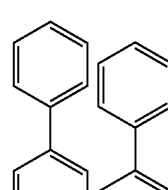 | 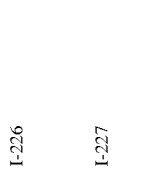 | 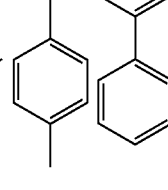 |
| I-231 | 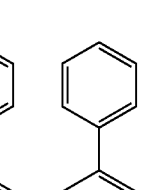 | 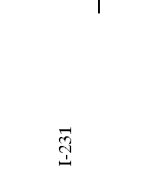 | 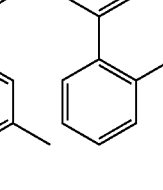 |

TABLE 17-continued
| Compound No. | Substituent | | | | |
|---|---|---|---|---|---|
| | R⁴⁰ | R⁵⁰ | R⁶⁰ | R⁷⁰ | R⁸⁰ |
| I-223 | 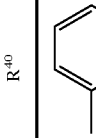 | H | H | H | H |
| I-224 | 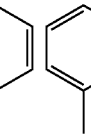 | | H | H | H |
| I-225 | 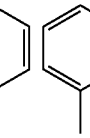 | H | H | H | H |
| I-226 | 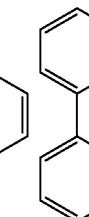 | | H | H | H |
| I-227 | 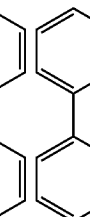 | H | H | H | H |

TABLE 17-continued

| | | | | | | | |
|---|---|---|---|---|---|---|---|
| H | H | H | H | H | H | H | H |
| H | H | H | H | H | H | H | H |
| H | H | H | H | H | H | H | H |
| H | H | H | H | H | H | H | H |
| I-228 | I-229 | I-230 | I-231 | I-232 | I-233 | I-234 | I-235 |

TABLE 18
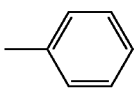
| Compound No. | R¹⁰ | R²⁰ | R³⁰ |
|---|---|---|---|
| I-238 | 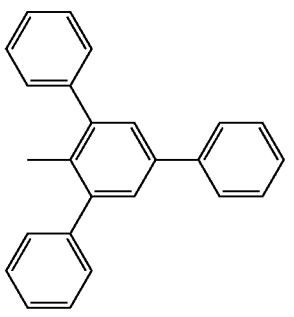 | 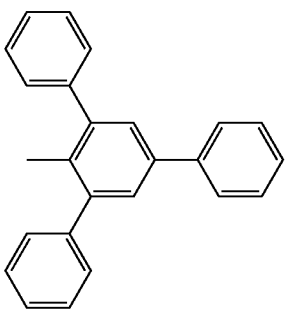 | 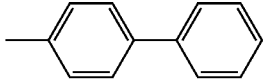 |
| I-254 | 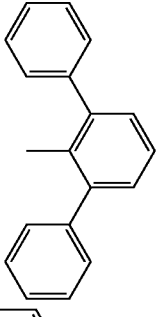 | 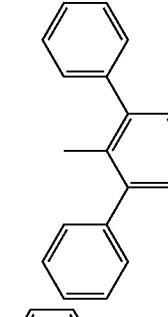 | 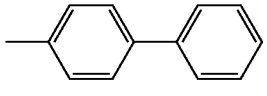 |
| I-255 | 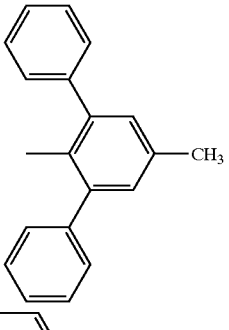 | 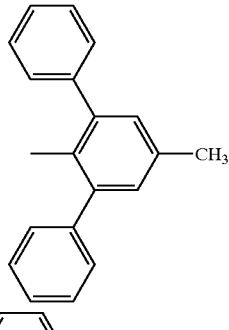 | 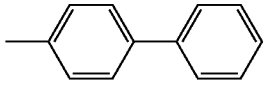 |
| I-256 | 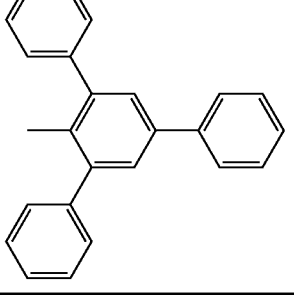 | 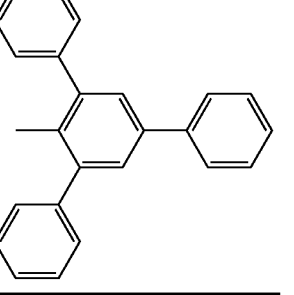 | |

TABLE 18-continued

| Compound No. | Substituent | | | | |
|---|---|---|---|---|---|
| | R⁴⁰ | R⁵⁰ | R⁶⁰ | R⁷⁰ | R⁸⁰ |
| I-238 | [phenyl] | —H | —H | —H | —H |
| I-254 | [biphenyl-4-yl] | —H | —H | —H | —H |
| I-255 | [biphenyl-4-yl] | —H | —H | —H | —H |
| I-256 | [biphenyl-4-yl] | —H | —H | —H | —H |

TABLE 19

| Compound No. | Substituent | | |
|---|---|---|---|
| | R¹⁰ | R²⁰ | R³⁰ |
| I-272 | [phenyl] | [m-terphenyl group] | [m-terphenyl group] |
| I-273 | [phenyl] | [o-terphenyl group] | [o-terphenyl group] |
| I-274 | [phenyl] | [substituted terphenyl] | [substituted terphenyl] |
| I-275 | [phenyl] | [substituted terphenyl] | [substituted terphenyl] |

TABLE 19-continued
| | | | | | | |
|---|---|---|---|---|---|---|
| I-276 | 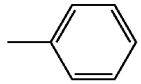 | | | | | |
| I-277 | 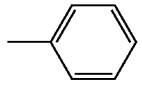 | | | | | |
| I-278 | 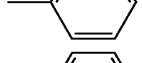 | | | | | |
| | Substituent | | | | |
|---|---|---|---|---|---|
| Compound No. | $R^{40}$ | $R^{50}$ | $R^{60}$ | $R^{70}$ | $R^{80}$ |
| I-272 | 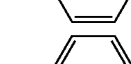 | H | H | H | H |
| I-273 | 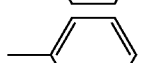 | H | H | H | H |
| I-274 | 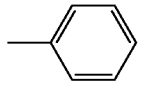 | H | H | H | H |
| I-275 |  | H | H | H | H |
| I-276 | 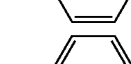 | H | H | H | H |
| I-277 | 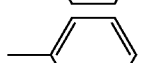 | H | H | H | H |
| I-278 | 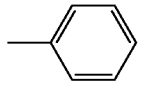 | H | H | H | H |

TABLE 20
| Compound No. | R¹⁰ | R²⁰ | R³⁰ |
|---|---|---|---|
| II-27 | 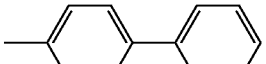 | 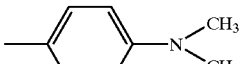 | 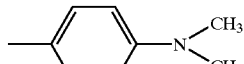 |
| II-28 | 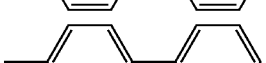 | 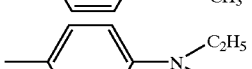 | 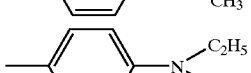 |
| II-29 | 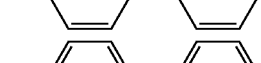 | 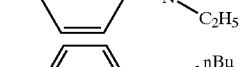 | 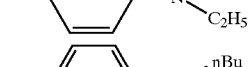 |
| II-30 | 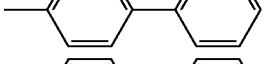 | 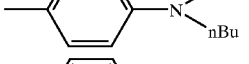 | 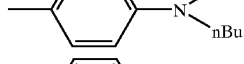 |
| II-31 | 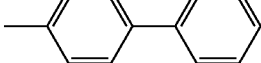 | 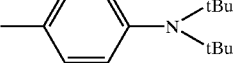 | 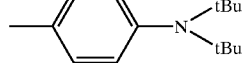 |
| II-32 | 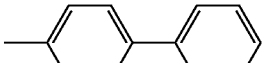 | 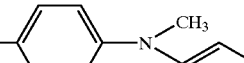 | 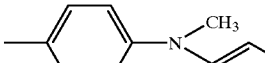 |
| II-33 | 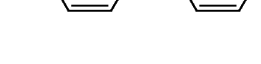 |  |  |
| II-34 | 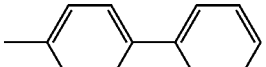 | 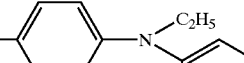 | 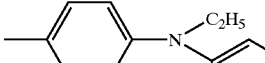 |
| II-35 | 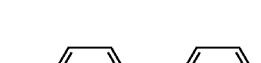 |  |  |
| II-36 | 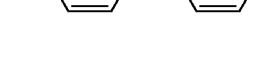 |  |  |
| Compound No. | R⁴⁰ | R⁵⁰ | R⁶⁰ | R⁷⁰ | R⁸⁰ |
|---|---|---|---|---|---|
| II-27 | 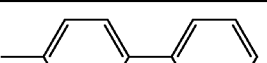 | H | H | H | H |
| II-28 | 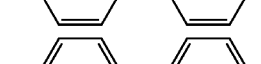 | H | H | H | H |

TABLE 20-continued
| | | | | | | |
|---|---|---|---|---|---|---|
| II-29 | 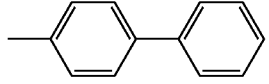 | H | H | H | H | |
| II-30 | 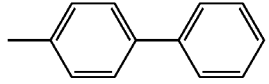 | H | H | H | H | |
| II-31 | 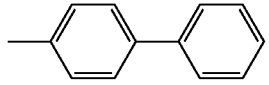 | H | H | H | H | |
| II-32 | 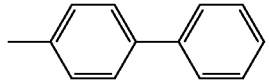 | H | H | H | H | |
| II-33 | 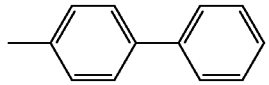 | H | H | H | H | |
| II-34 | 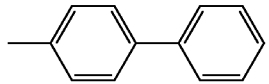 | H | H | H | H | |
| II-35 | 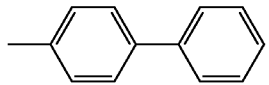 | H | H | H | H | |
| II-36 | 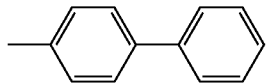 | H | H | H | H | |
TABLE 21
| Compound No. | Substituent | | |
|---|---|---|---|
| | $R^{10}$ | $R^{20}$ | $R^{30}$ |
| II-37 | 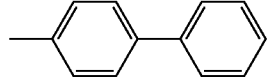 | 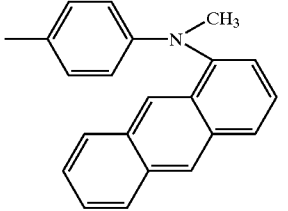 | 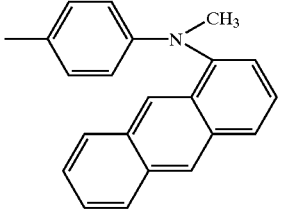 |
| II-38 | 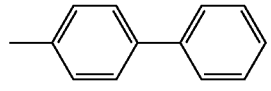 | 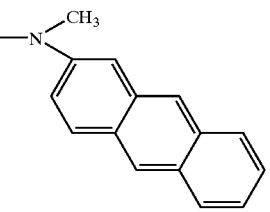 | 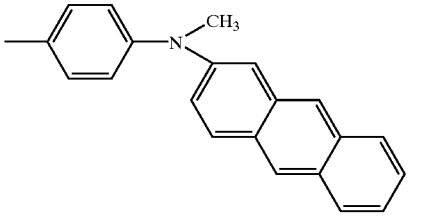 |
| II-39 | 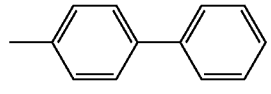 | 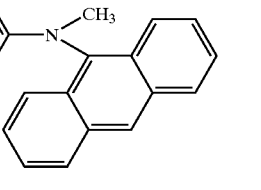 | 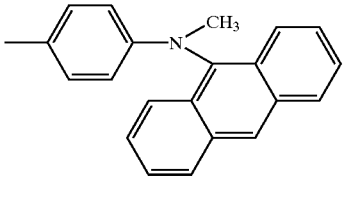 |

TABLE 21-continued

| Compound No. | Substituent | | | | |
|---|---|---|---|---|---|
| | $R^{40}$ | $R^{50}$ | $R^{60}$ | $R^{70}$ | $R^{80}$ |
| II-37 | [biphenyl group] | H | H | H | H |
| II-38 | [biphenyl group] | H | H | H | H |
| II-39 | [biphenyl group] | H | H | H | H |

TABLE 22

| Compound No. | Substituent | | |
|---|---|---|---|
| | $R^{10}$ | $R^{20}$ | $R^{30}$ |
| II-70 | [biphenyl group] | [N,N-diphenyl-p-tolylamine group] | [N,N-diphenyl-p-tolylamine group] |
| II-71 | [biphenyl group] | [N-phenyl-N-(p-tolyl)-p-tolylamine group] | [N-phenyl-N-(p-tolyl)-p-tolylamine group] |
| II-72 | [biphenyl group] | [N-phenyl-N-(m-tolyl)-p-tolylamine group] | [N-phenyl-N-(m-tolyl)-p-tolylamine group] |
| II-73 | [biphenyl group] | [N-phenyl-N-(o-tolyl)-p-tolylamine group] | [N-phenyl-N-(o-tolyl)-p-tolylamine group] |

TABLE 22-continued

| Compound No. | | Substituent | | | | |
|---|---|---|---|---|---|---|
| | | R⁴⁰ | R⁵⁰ | R⁶⁰ | R⁷⁰ | R⁸⁰ |
| II-70 | | biphenyl | H | H | H | H |
| II-71 | | biphenyl | H | H | H | H |
| II-72 | | biphenyl | H | H | H | H |
| II-73 | | biphenyl | H | H | H | H |
| II-74 | | biphenyl | H | H | H | H |
| II-75 | | biphenyl | H | H | H | H |
| II-76 | | biphenyl | H | H | H | H |

TABLE 23

| Compound No. | Substituent | | |
| --- | --- | --- | --- |
| | R¹⁰ | R²⁰ | R³⁰ |
| II-77 | 4-biphenylyl | N-phenyl-N-(1-naphthyl)-4-aminotolyl | N-phenyl-N-(1-naphthyl)-4-aminotolyl |
| II-78 | 4-biphenylyl | N-phenyl-N-(2-naphthyl)-4-aminotolyl | N-phenyl-N-(2-naphthyl)-4-aminotolyl |
| II-79 | 4-biphenylyl | N,N-di(1-naphthyl)-4-aminotolyl | N,N-di(1-naphthyl)-4-aminotolyl |
| II-80 | 4-biphenylyl | N,N-di(2-naphthyl)-4-aminotolyl | N,N-di(2-naphthyl)-4-aminotolyl |

TABLE 23-continued
| | | | |
|---|---|---|---|
| II-81 | 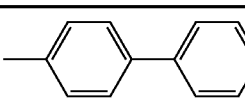 | 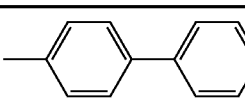 | 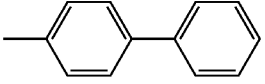 |
| II-82 | 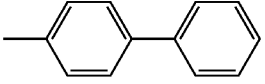 | 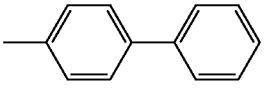 | 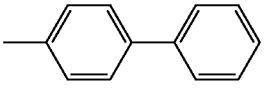 |
| Compound No. | Substituent | | | | |
|---|---|---|---|---|---|
| | $R^{40}$ | $R^{50}$ | $R^{60}$ | $R^{70}$ | $R^{80}$ |
| II-77 | 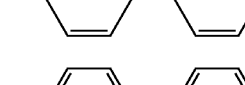 | H | H | H | H |
| II-78 | 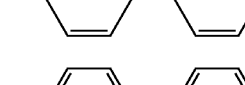 | H | H | H | H |
| II-79 | 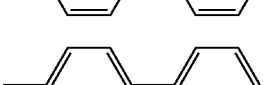 | H | H | H | H |
| II-80 | 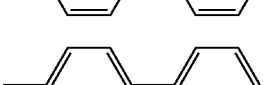 | H | H | H | H |
| II-81 | 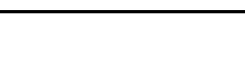 | H | H | H | H |
| II-82 | 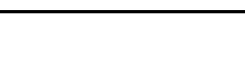 | H | H | H | H |

TABLE 24
| Compound No. | Substituent | | |
|---|---|---|---|
| | $R^{10}$ | $R^{20}$ | $R^{30}$ |
| II-83 | 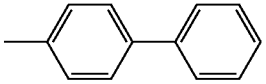 | 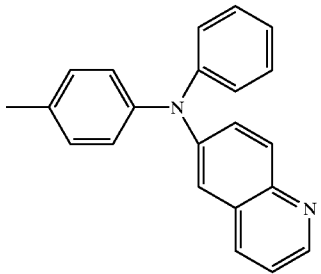 | 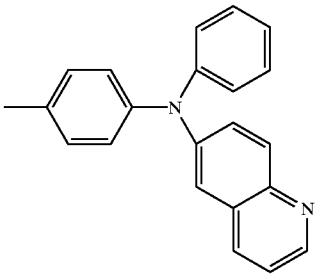 |
| II-84 | 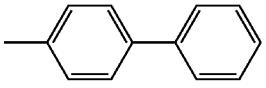 | 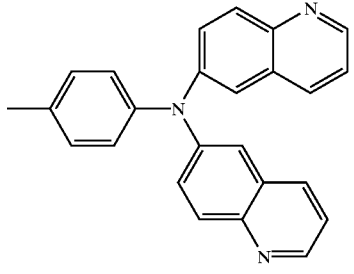 | 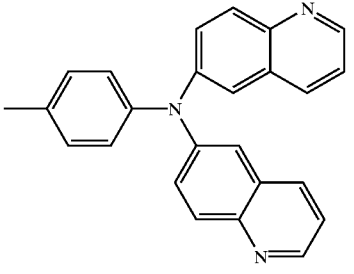 |
| Compound No. | Substituent | | | | |
|---|---|---|---|---|---|
| | $R^{40}$ | $R^{50}$ | $R^{60}$ | $R^{70}$ | $R^{80}$ |
| II-83 | 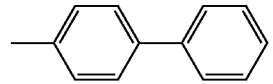 | H | H | H | H |
| II-84 | 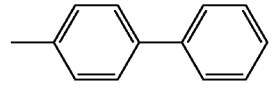 | H | H | H | H |
TABLE 25
| Compound No. | Substituent | | |
|---|---|---|---|
| | $R^{10}$ | $R^{20}$ | $R^{30}$ |
| II-85 | 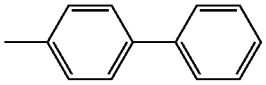 | 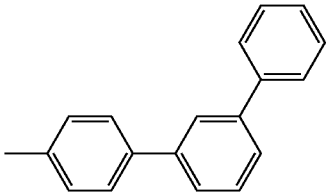 | 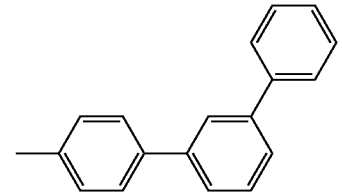 |
| II-86 | 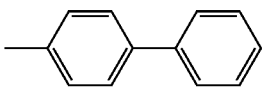 | 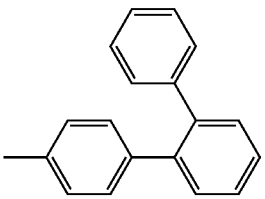 | 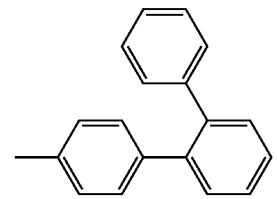 |

TABLE 25-continued
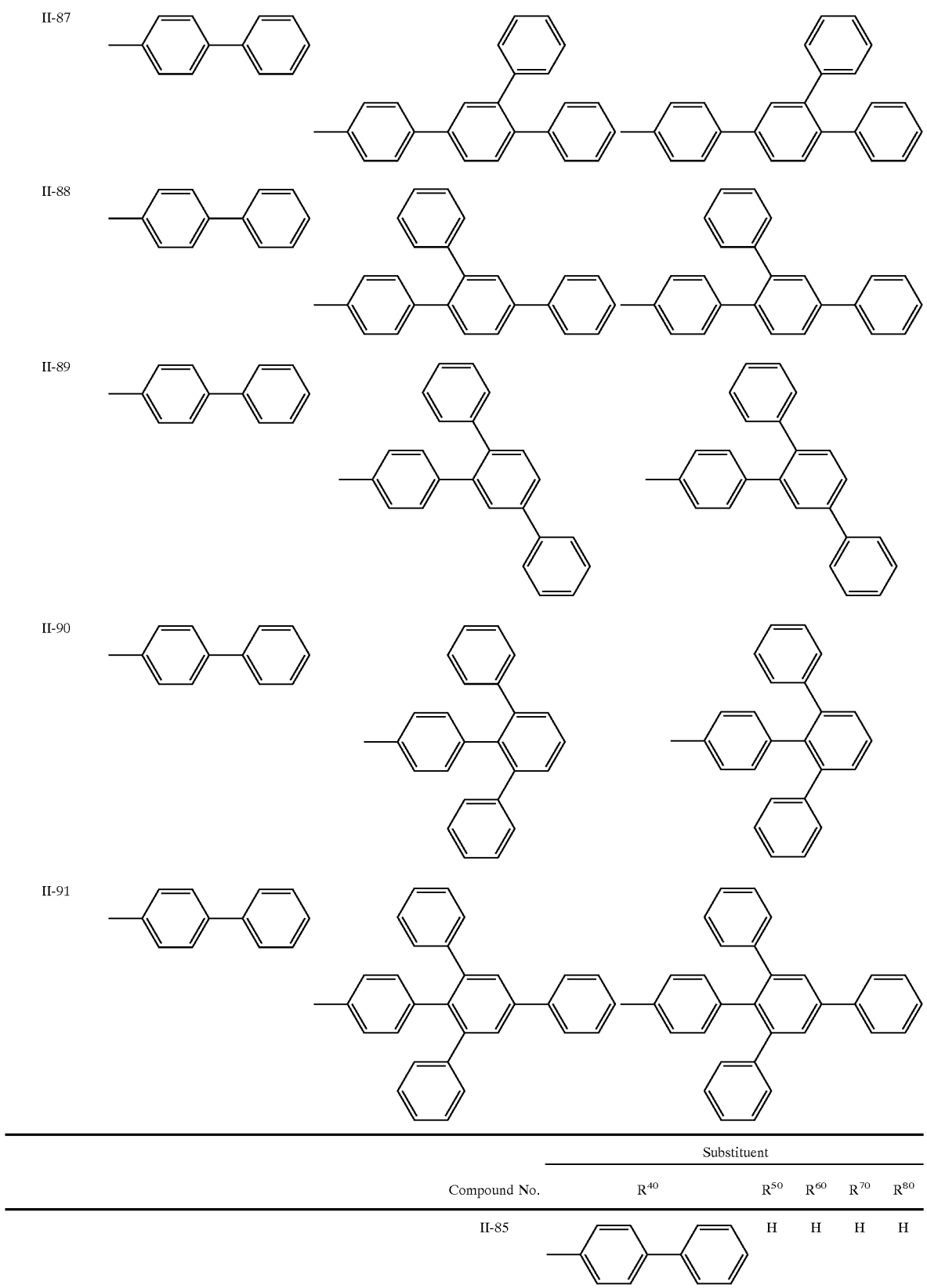
| | Substituent | | | | |
|---|---|---|---|---|---|
| Compound No. | $R^{40}$ | $R^{50}$ | $R^{60}$ | $R^{70}$ | $R^{80}$ |
| II-85 | (4-biphenylyl) | H | H | H | H |

TABLE 25-continued
| | | R¹⁰ | | | | |
|---|---|---|---|---|---|---|
| | II-86 | 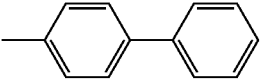 | H | H | H | H |
| | II-87 | 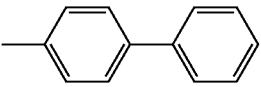 | H | H | H | H |
| | II-88 | 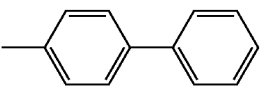 | H | H | H | H |
| | II-89 | 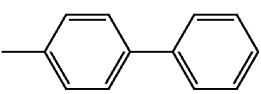 | H | H | H | H |
| | II-90 | 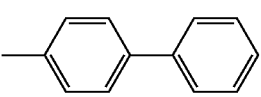 | H | H | H | H |
| | II-91 | 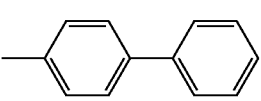 | H | H | H | H |
TABLE 26
| | Substituent | | |
|---|---|---|---|
| Compound No. | $R^{10}$ | $R^{20}$ | $R^{30}$ |
| III-21 | 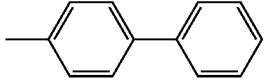 | 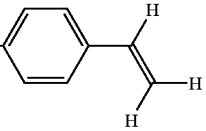 | 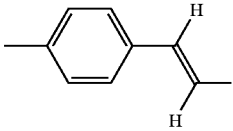 |
| III-22 | 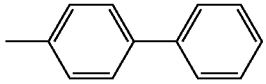 | 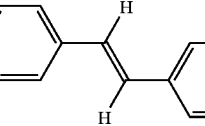 | 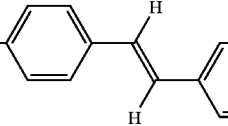 |
| III-23 | 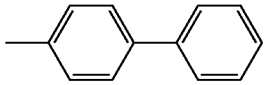 | 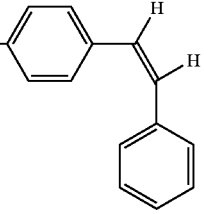 | 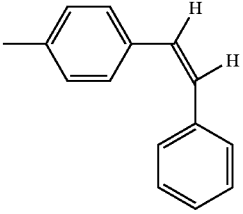 |
| III-24 | 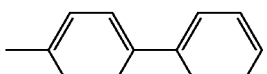 | 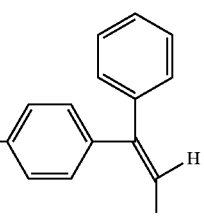 | 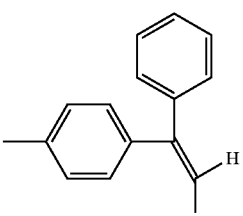 |

TABLE 26-continued
| Compound No. | Substituent R⁴⁰ | R⁵⁰ | R⁶⁰ | R⁷⁰ | R⁸⁰ |
|---|---|---|---|---|---|
| III-21 | 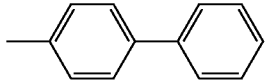 | H | H | H | H |
| III-22 | 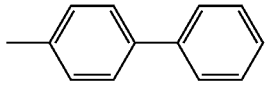 | H | H | H | H |
| III-23 | 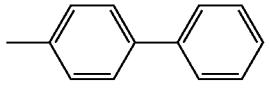 | H | H | H | H |
| III-24 | 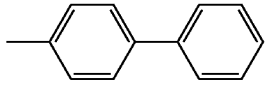 | H | H | H | H |
| III-25 | 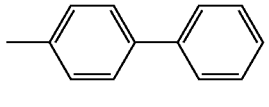 | H | H | H | H |
| III-26 | 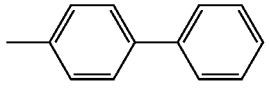 | H | H | H | H |
| III-27 | 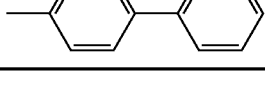 | H | H | H | H |
III-25 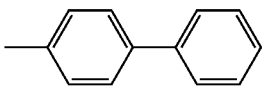
III-26 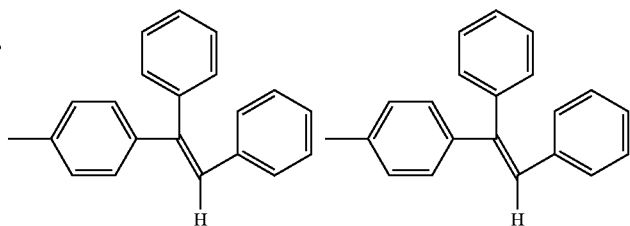
III-27 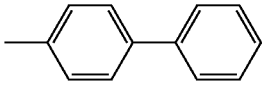

TABLE 27

| Compound No. | Substituent | | |
|---|---|---|---|
| | $R^{10}$ | $R^{20}$ | $R^{30}$ |
| III-28 | 4-biphenylyl | 1,2,2-triphenylvinyl-substituted phenyl | 1,2,2-triphenylvinyl-substituted phenyl |
| III-29 | 4-biphenylyl | 4-(4-phenyl-1,3-butadienyl)phenyl | 4-(4-phenyl-1,3-butadienyl)phenyl |
| III-30 | 4-biphenylyl | 4-(4-vinylstyryl)phenyl-styryl | 4-(4-vinylstyryl)phenyl-styryl |

| Compound No. | Substituent | | | | |
|---|---|---|---|---|---|
| | $R^{40}$ | $R^{50}$ | $R^{60}$ | $R^{70}$ | $R^{80}$ |
| III-28 | 4-biphenylyl | H | H | H | H |
| III-29 | 4-biphenylyl | H | H | H | H |
| III-30 | 4-biphenylyl | H | H | H | H |

TABLE 28
| Compound No. | R¹⁰ | R²⁰ | R³⁰ | R⁴⁰ | R⁵⁰ | R⁶⁰ | R⁷⁰ | R⁸⁰ |
|---|---|---|---|---|---|---|---|---|
| III-31 | 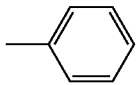 | 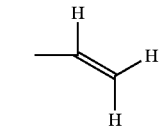 | 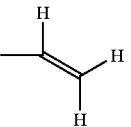 | 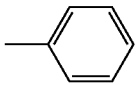 | H | H | H | H |
| III-32 | 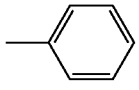 | 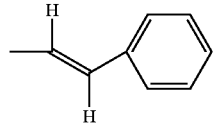 | 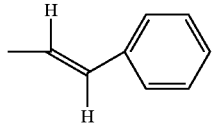 | 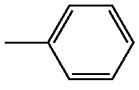 | H | H | H | H |
| III-33 | 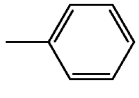 | 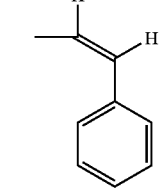 | 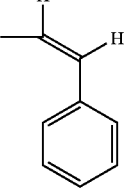 | 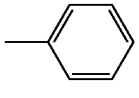 | H | H | H | H |
| III-34 | 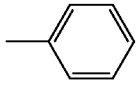 | 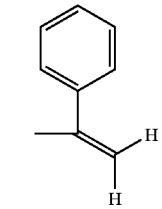 | 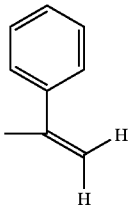 | 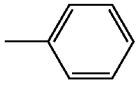 | H | H | H | H |
| III-35 | 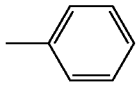 | 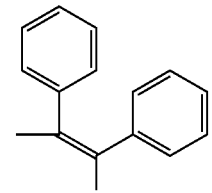 | 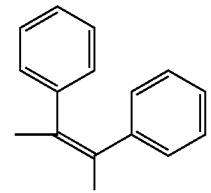 | 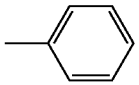 | H | H | H | H |
| III-36 | 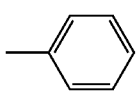 | 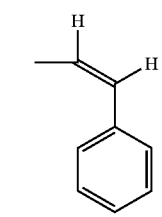 | 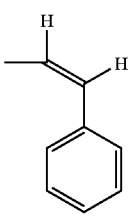 | 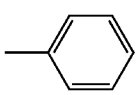 | H | H | H | H |
| III-37 | 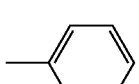 | 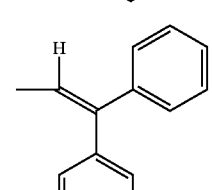 | 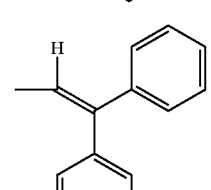 | 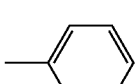 | H | H | H | H |

TABLE 28-continued
| Compound No. | Substituent | | | | | | | |
|---|---|---|---|---|---|---|---|---|
| | $R^{10}$ | $R^{20}$ | $R^{30}$ | $R^{40}$ | $R^{50}$ | $R^{60}$ | $R^{70}$ | $R^{80}$ |
| III-38 | 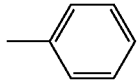 | 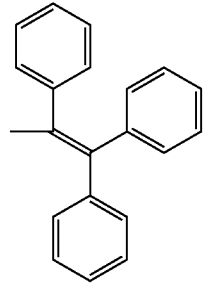 | 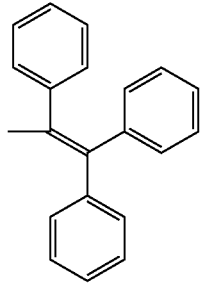 | 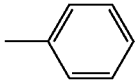 | H | H | H | H |
TABLE 29
| Compound No. | Substituent | | |
|---|---|---|---|
| | $R^{10}$ | $R^{20}$ | $R^{30}$ |
| III-39 | 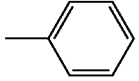 | 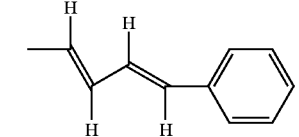 | 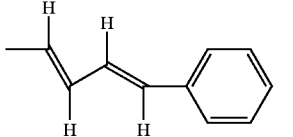 |
| III-40 | 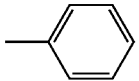 | 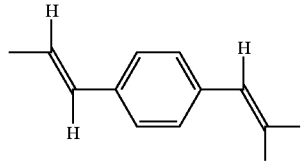 | 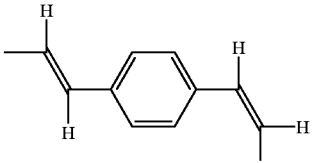 |
| Compound No. | Substituent | | | | |
|---|---|---|---|---|---|
| | $R^{40}$ | $R^{50}$ | $R^{60}$ | $R^{70}$ | $R^{80}$ |
| III-39 | 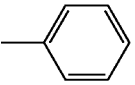 | H | H | H | H |
| III-40 | 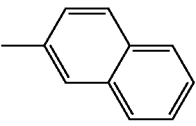 | H | H | H | H |
TABLE 30
| Compound No. | Substituent | | | | | | | |
|---|---|---|---|---|---|---|---|---|
| | $R^{10}$ | $R^{20}$ | $R^{30}$ | $R^{40}$ | $R^{50}$ | $R^{60}$ | $R^{70}$ | $R^{80}$ |
| III-41 | 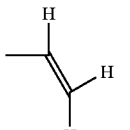 | 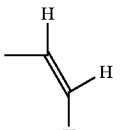 | 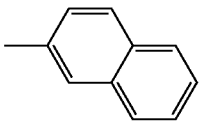 | | H | H | H | H |

TABLE 30-continued
| Compound No. | R¹⁰ | R²⁰ | R³⁰ | R⁴⁰ | R⁵⁰ | R⁶⁰ | R⁷⁰ | R⁸⁰ |
|---|---|---|---|---|---|---|---|---|
| III-42 | 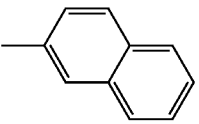 | 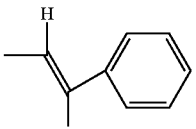 | 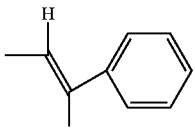 | 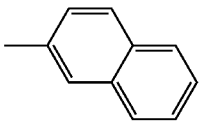 | H | H | H | H |
| III-43 | 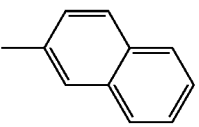 | 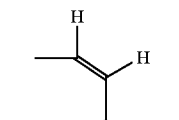 | 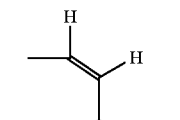 | 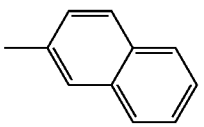 | H | H | H | H |
| III-44 | 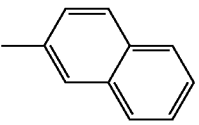 | 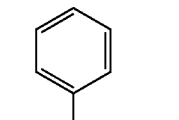 | 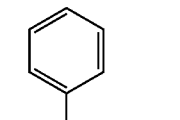 | 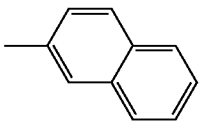 | H | H | H | H |
| III-45 | 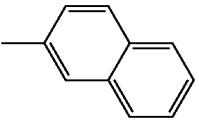 | 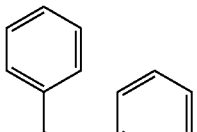 | 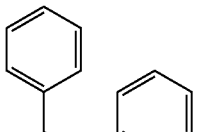 | 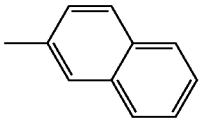 | H | H | H | H |
| III-46 | 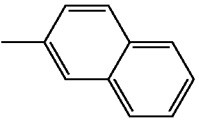 | 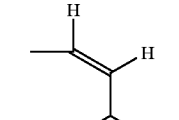 | 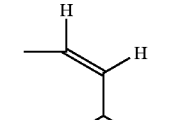 | 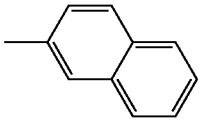 | H | H | H | H |
| III-47 | 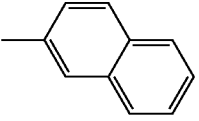 | 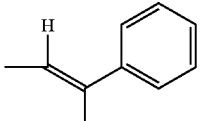 | 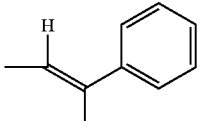 | 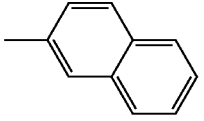 | H | H | H | H |

TABLE 30-continued
| Compound No. | Substituent | | | | | | | |
|---|---|---|---|---|---|---|---|---|
| | R10 | R20 | R30 | R40 | R50 | R60 | R70 | R80 |
| III-48 | 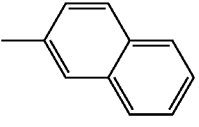 | 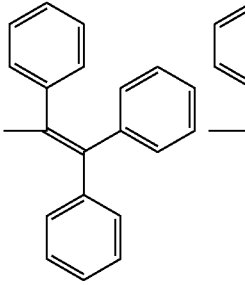 | 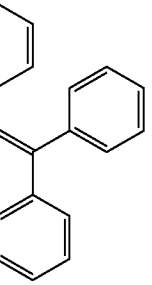 | 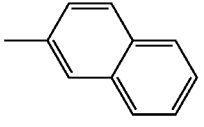 | H | H | H | H |
TABLE 31
| Compound No. | Substituent | | |
|---|---|---|---|
| | R10 | R20 | R30 |
| III-49 | 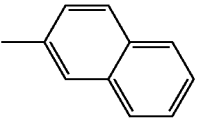 | 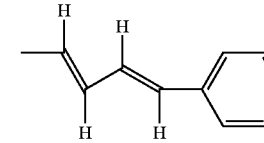 | 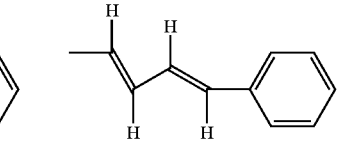 |
| III-50 | 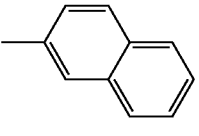 | 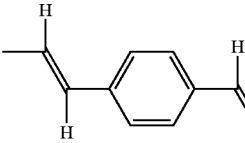 | 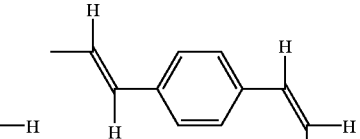 |
| Compound No. | Substituent | | | | |
|---|---|---|---|---|---|
| | R40 | R50 | R60 | R70 | R80 |
| III-49 | 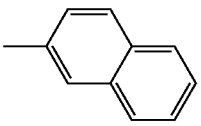 | H | H | H | H |
| III-50 | 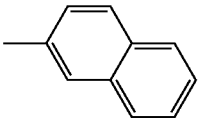 | H | H | H | H |

TABLE 32

| Compound No. | Substituent | | |
| --- | --- | --- | --- |
| | R¹⁰ | R²⁰ | R³⁰ |
| III-51 | 4-biphenyl | propenyl | propenyl |
| III-52 | 4-biphenyl | β-methylstyryl | β-methylstyryl |
| III-53 | 4-biphenyl | styryl (α-methyl) | styryl (α-methyl) |
| III-54 | 4-biphenyl | α-phenylpropenyl | α-phenylpropenyl |
| III-55 | 4-biphenyl | 1,2-diphenylpropenyl | 1,2-diphenylpropenyl |
| III-56 | 4-biphenyl | styryl | styryl |
| III-57 | 4-biphenyl | 1,2-diphenylvinyl | 1,2-diphenylvinyl |

TABLE 32-continued

| Compound No. | Substituent | | | | |
|---|---|---|---|---|---|
| | R⁴⁰ | R⁵⁰ | R⁶⁰ | R⁷⁰ | R⁸⁰ |
| III-51 | [biphenyl] | H | H | H | H |
| III-52 | [biphenyl] | H | H | H | H |
| III-53 | [biphenyl] | H | H | H | H |
| III-54 | [biphenyl] | H | H | H | H |
| III-55 | [biphenyl] | H | H | H | H |
| III-56 | [biphenyl] | H | H | H | H |
| III-57 | [biphenyl] | H | H | H | H |
| III-58 | [biphenyl] | H | H | H | H |

TABLE 33

| Compound No. | Substituent | | |
|---|---|---|---|
| | R¹⁰ | R²⁰ | R³⁰ |
| III-59 | [biphenyl] | [styryl group] | [styryl group] |

TABLE 33-continued
| | | | | | | |
|---|---|---|---|---|---|---|
| III-60 | ![biphenyl] | ![divinyl benzene] | | ![divinyl benzene] | | |
| | | Substituent | | | | |
|---|---|---|---|---|---|---|
| Compound No. | $R^{40}$ | | $R^{50}$ | $R^{60}$ | $R^{70}$ | $R^{80}$ |
| III-59 | ![biphenyl group] | | H | H | H | H |
| III-60 | ![biphenyl group] | | H | H | H | H |
The compound of the invention is obtained, for example, according to the following synthetic scheme.
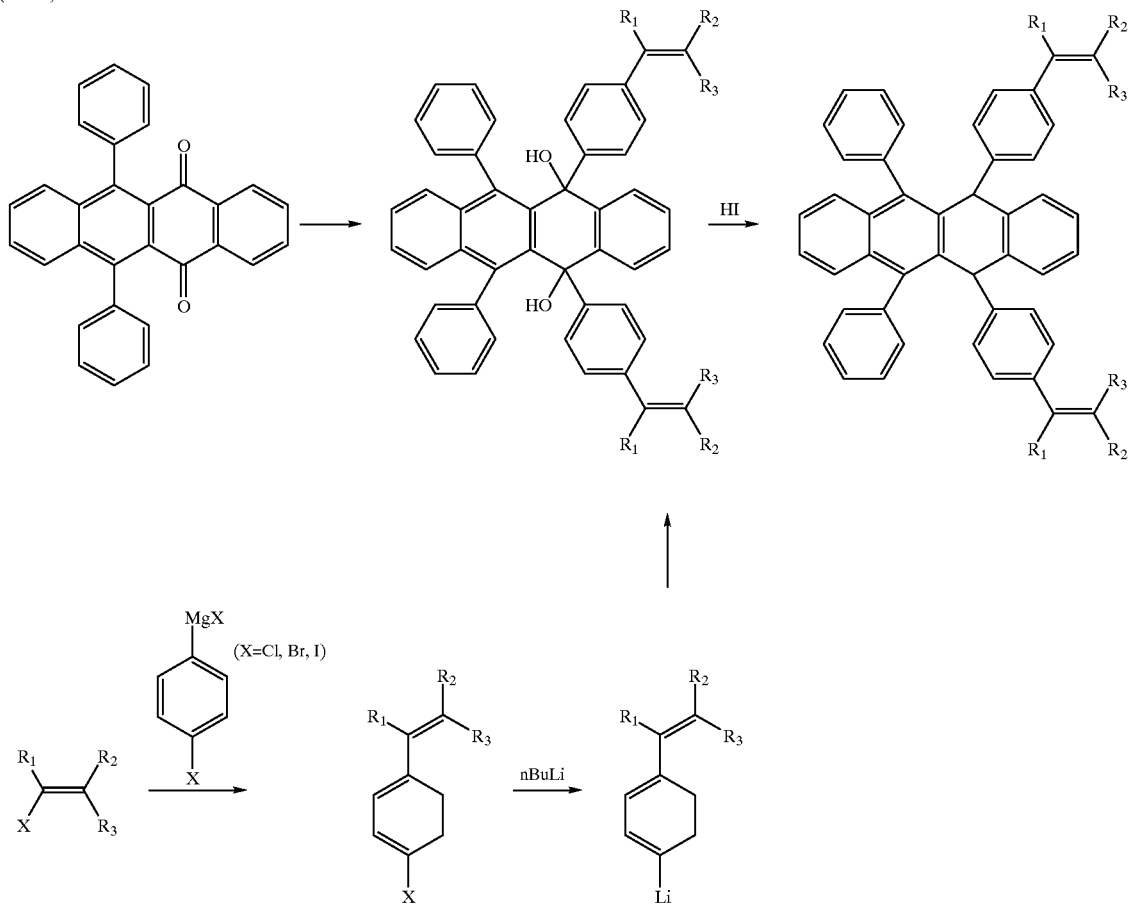
(CF 12)

(CF 13)

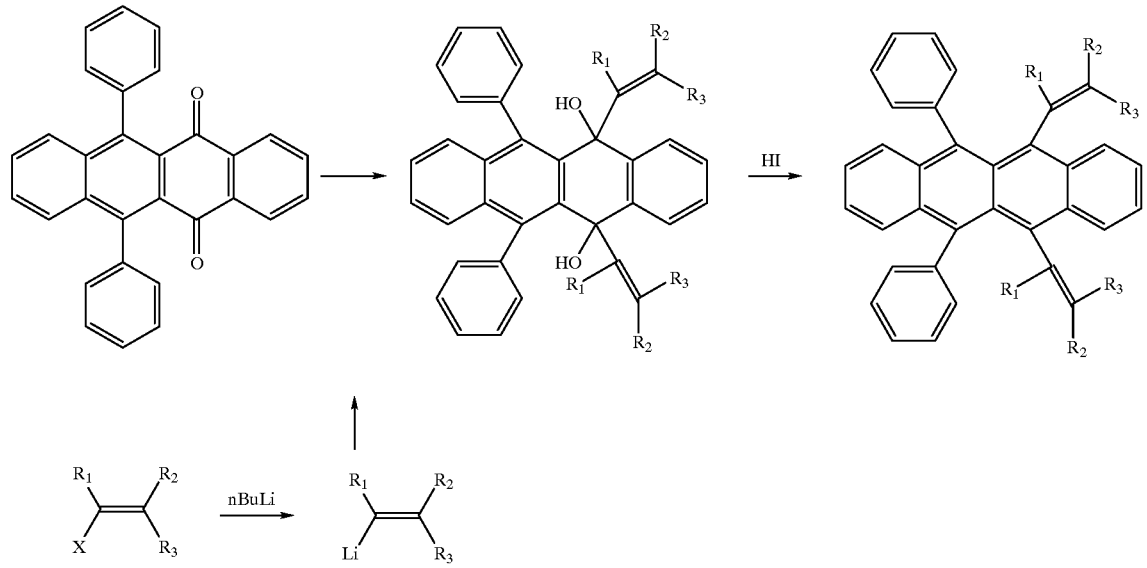

The organic EL device of the invention has a hole injecting electrode, an electron injecting electrode, and an organic layer disposed between the electrodes and including at least a light emitting layer, wherein the light emitting layer contains the above-described compound.

Also, the organic EL device of the invention may contain at least two compounds having a basic skeleton represented by the above formula (IV).

In formula (IV), $R^{101}$, $R^{102}$, $R^{103}$, and $R^{104}$ each are hydrogen or a substituted or unsubstituted aryl or alkenyl group, excluding the case where at least three R's are hydrogen atoms. $R^{105}$, $R^{106}$, $R^{107}$, and $R^{108}$ each are hydrogen or a substituted or unsubstituted aryl or alkenyl group. At least two of $R^{101}$ to $R^{104}$ are aryl groups of at least two rings or alkenyl groups, or have alkyl, aryl, amino, alkenyl, aryloxy or heterocyclic groups as substituents.

The detail of the groups $R^{101}$, $R^{102}$, $R^{103}$, and $R^{104}$ and the substituents thereon are the same as described for $R^1$, $R^2$, $R^3$, and $R^4$ in above formula (I).

$R^{105}$, $R^{106}$, $R^{107}$, and $R^{108}$ each are hydrogen or a substituted or unsubstituted alkyl, aryl, amino or alkenyl group.

The aryl, amino and alkenyl groups represented by $R^{105}$, $R^{106}$, $R^{107}$, and $R^{108}$ are as described above for $R^1$ to $R^4$. It is preferred that $R^{105}$ and $R^{106}$, and $R^{107}$ and $R^{108}$ in the respective pairs are identical although they may be different.

By incorporating at least two such compounds having different carrier trapping capabilities, it becomes possible to reduce the drive voltage and extend the life of the device for continuous light emission. The luminance of light emission is improved by a proper choice of the compounds to be combined.

When the light emitting layer contains at least two of the compounds, the preferred combination is a combination of a hole trapping compound having an arylamino or aryloxy group and an electron trapping compound consisting of hydrocarbon. Illustrative preferred combinations are combinations of (CF 15) with (CF 29), (CF 15) with (CF 16), (CF 15) with (CF 17), and (CF 15) with (CF 30) to be described below.

Also, similar effects are achieved by combinations of only compounds consisting of hydrocarbon. Exemplary are combinations of (1) a compound of formula (IV) wherein $R^{101}$, $R^{102}$, $R^{103}$, and $R^{104}$ are all aryl or ethenyl groups with a compound of formula (IV) wherein $R^{101}$ to $R^{106}$ are all aryl or ethenyl groups; (2) a compound of formula (IV) wherein $R^{101}$, $R^{102}$, and $R^{103}$ are all aryl or ethenyl groups with a compound of formula (IV) wherein $R^{101}$ to $R^{108}$ are all aryl or ethenyl groups; (3) a compound of formula (IV) wherein two of $R^{101}$, $R^{102}$, $R^{103}$, and $R^{104}$ are aryl groups with a compound of formula (IV) wherein $R^{101}$, $R^{102}$, $R^{103}$, and $R^{104}$ are all aryl or ethenyl groups; and (4) compounds of formula (IV) wherein $R^{101}$, $R^{102}$, $R^{103}$, and $R^{104}$ are all aryl groups.

Illustrative combinations are given below.

Examples of combination (1) are (CF 29) with (CF 30), (CF 14) with (CF 30), and (CF 16) with (CF 30);

examples of combination (2) are (CF 29) with (CF 54), (CF 14) with (CF 54), (CF 16) with (CF 54), and (CF 17) with (CF 54);

examples of combination (3) are (CF 32) with (CF 29), (CF 32) with (CF 14), (CF 32) with (CF 16), and (CF 32) with (CF 17); and examples of combination (4) are (CF 29) with (CF 14), (CF 29) with (CF 16), (CF 29) with (CF 17), (CF 14) with (CF 16), (CF 14) with (CF 17), and (CF 16) with (CF 17).

(CF 54)

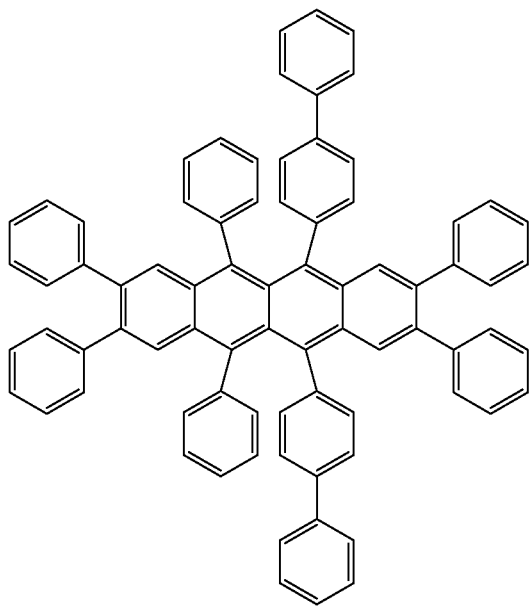

The light emitting layer containing the compound of the invention has functions of injecting holes and electrons, transporting them, and recombining holes and electrons to create excitons. The use of relatively electronically neutral compounds in the light emitting layer in addition to the compound of the invention enables easy and well-balanced injection and transportation of electrons and holes.

In the light emitting layer of the organic EL device of the invention, it is preferred to use the inventive compound in combination with a host material capable of light emission by itself, that is, to use the compound as a dopant. In this embodiment, the content of the inventive compound in the light emitting layer is preferably 0.01 to 10% by weight, especially 0.1 to 5% by weight. By using the compound in combination with the host material, the light emission wavelength of the host material can be altered, enabling light emission shifted to a longer wavelength and improving the luminous efficiency and stability of the device.

Preferred host materials are quinolinolato complexes, more preferably aluminum complexes having 8-quinolinol or a derivative thereof as a ligand. Examples of the aluminum complex are disclosed in JP-A 63-264692, 3-255190, 5-70733, 5-258859, and 6-215874.

Examples of the former include tris(8-quinolinolato) aluminum, bis(8-quinolinolato)magnesium, bis(benzo[f]-8-quinolinolato)zinc, bis(2-methyl-8-quinolinolato)aluminum oxide, tris(8-quinolinolato)indium, tris(5-methyl-8-quinolinolato)aluminum, 8-quinolinolatolithium, tris(5-chloro-8-quinolinolato)gallium, bis(5-chloro-8 quinolinolato)calcium, 5,7-dichloro-8-quinolinolatoaluminum, tris(5,7-dibromo-8-hydroxyquinolinolato)aluminum, and poly[zinc(II)-bis(8-hydroxy-5-quinolinyl)methane].

Also useful are aluminum complexes having another ligand in addition to 8-quinolinol or a derivative thereof. Examples include bis(2-methyl-8-quinolinolato)(phenolato) aluminum(III), bis(2-methyl-8-quinolinolato) (orthocresolato)aluminum(III), bis(2-methyl-8-quinolinolato)(meta-cresolato)aluminum(III), bis(2-methyl-8-quinolinolato)(para-cresolato)aluminum(III), bis(2-methyl-8-quinolinolato)(ortho-phenylphenolato)aluminum (III), bis(2-methyl-8-quinolinolato)(meta-phenylphenolato) aluminum(III), bis(2-methyl-8-quinolinolato)(para-phenylphenolato)aluminum(III), bis(2-methyl-8-quinolinolato)(2,3-dimethylphenolato)aluminum(III), bis(2-methyl-8-quinolinolato)(2,6-dimethylphenolato)aluminum (III), bis(2-methyl-8-quinolinolato)(3,4-dimethylphenolato) aluminum(III), bis(2-methyl-8-quinolinolato)(3,5-dimethylphenolato)aluminum(III), bis(2-methyl-8-quinolinolato)(3,5-di-tert-butylphenolato)aluminum(III), bis(2-methyl-8-quinolinolato)(2,6-diphenylphenolato) aluminum(III), bis(2-methyl-8-quinolinolato)(2,4,6-triphenylphenolato)aluminum(III), bis(2-methyl-8-quinolinolato)(2,3,6-trimethylphenolato)aluminum(III), bis(2-methyl-8-quinolinolato)(2,3,5,6-tetramethylphenolato) aluminum(III), bis(2-methyl-8-quinolinolato)(1-naphtholato)aluminum(III), bis(2-methyl-8-quinolinolato) (2-naphtholato)aluminum(III), bis(2,4-dimethyl-8-quinolinolato)(ortho-phenylphenolato)aluminum(III), bis(2,4-dimethyl-8-quinolinolato)(para-phenylphenolato) aluminum(III), bis(2,4-dimethyl-8-quinolinolato) (metaphenylphenolato)aluminum(III), bis(2,4-dimethyl-8-quinolinolato)(3,5-dimethylphenolato)aluminum(III), bis(2,4-dimethyl-8-quinolinolato)(3,5-di-tertbutylphenolato) aluminum(III), bis(2-methyl-4-ethyl-8-quinolinolato)(para-cresolato)aluminum(III), bis(2-methyl4-methoxy-8-quinolinolato)(para-phenylphenolato)aluminum(III), bis(2-methyl-5-cyano-8-quinolinolato)(orthocresolato)aluminum (III), and bis(2-methyl-6-trifluoromethyl-8-quinolinolato) (2-naphtholato)aluminum(III).

Also acceptable are bis(2-methyl-8-quinolinolato) aluminum(III)-$\mu$-oxo-bis(2-methyl-8-quinolinolato) aluminum(III), bis(2,4-dimethyl-8-quinolinolato)aluminum (III)-$\mu$-oxo-bis(2,4-dimethyl-8-quinolinolato)aluminum (III), bis(4-ethyl-2-methyl-8-quinolinolato)aluminum(III)-$\mu$-oxo-bis(4-ethyl-2-methyl-8-quinolinolato)aluminum(III), bis(2-methyl-4-methoxyquinolinolato)aluminum(III)-$\mu$-oxo-bis(2-methyl-4-methoxyquinolinolato)aluminum(III), bis(5-cyano-2-methyl-8-quinolinolato)aluminum(III)-$\mu$-oxo-bis(5-cyano-2-methyl-8-quinolinolato)aluminum(III), and bis(2-methyl-5-trifluoromethyl-8-quinolinolato) aluminum(III)-$\mu$-oxo-bis(2-methyl-5-trifluoromethyl-8-quinolinolato)aluminum(III).

Other useful host materials are the phenylanthracene derivatives described in Japanese Patent Application No. 6-110569 and the tetraarylethene derivatives described in Japanese Patent Application No. 6-114456. Also, triphenylamine derivatives as typified by TPD are preferred host materials.

The light emitting layer may contain another luminescent material. Such a luminescent material may be at least one compound selected from compounds as disclosed in JP-A 63-264692, for example, quinacridone and styryl dyes. Also included are quinoline derivatives, for example, metal complex dyes having 8-quinolinol or a derivative thereof as a ligand such as tris(8-quinolinolato)aluminum, tetraphenylbutadiene, anthracene, perylene, coronene, and 12-phthaloperinone derivatives. Further included are the phenylanthracene derivatives of Japanese Patent Application No. 6-110569 and the tetraarylethene derivatives of Japanese Patent Application No. 6-114456.

The light emitting layer may also serve as an electron injecting and transporting layer. In this embodiment, the use of tris(8-quinolinolato)aluminum or the like is preferred. These fluorescent materials may be evaporated.

If desired, the light emitting layer is a layer of a mixture of at least one hole injecting and transporting compound and at least one electron injecting and transporting compound in which the inventive compound is contained as a dopant. In such a mix layer, the content of the inventive compound is preferably 0.01 to 20% by weight, especially 0.1 to 15% by weight.

In the mix layer, carrier hopping conduction paths are created, allowing carriers to move through a polarly predominant material while injection of carriers of opposite polarity is rather inhibited. The organic compound is less susceptible to damage, resulting in the advantage of an extended device life. By incorporating the above-described dopant in such a mix layer, the light emission wavelength the mix layer itself possesses can be altered, enabling light emission shifted to a longer wavelength and improving the luminous intensity and stability of the device. In particular, the inventive compound, which is stable to both electron and hole injection, can contribute to a drastic increase of the light emission life even at a doping level of about 2% by weight.

When the carrier trapping capability of a dopant is biased toward the electron or hole side, at least two dopants having different carrier trapping capabilities may be used to improve recombination and hence, to increase the probability of recombination. By using dopants having different carrier trapping capabilities, the probability of recombination of holes and electrons in the light emitting layer is improved so that the light emission efficiency and luminous intensity are improved. The especially preferred combination is a combination of a dopant having a high electron trapping capability to the host material with a dopant having a high hole trapping capability to the host material.

The hole injecting and transporting compound and electron injecting and transporting compound used in the mix layer may be selected from compounds for the hole injecting and transporting layer and compounds for the electron injecting and transporting layer to be described later, respectively. Specifically, the compounds for the hole injecting and transporting layer are preferably amine derivatives having strong fluorescence, for example, triphenyldiamine (TPD) derivatives, styrylamine derivatives and amine derivatives having an aromatic fused ring known as the hole injecting and transporting material.

The compounds for the electron injecting and transporting layer are preferably quinoline derivatives and metal complexes having 8-quinolinol or a derivative thereof as a ligand, especially tris(8-quinolinolato)aluminum (Alq3). The phenylanthracene derivatives and tetraarylethene derivatives described above are also preferably used.

The compounds for the hole injecting and transporting layer are preferably amine derivatives having strong fluorescence, for example, triphenyldiamine derivatives, styrylamine derivatives and amine derivatives having an aromatic fused ring known as the hole injecting and transporting material.

With respect to the mix ratio, which is determined in consideration of the respective carrier mobility and carrier concentration, it is preferred that the weight ratio of the hole injecting and transporting compound to the electron injecting and transporting compound range from about 1/99 to 99/1, more preferably from about 10/90 to 90/10, especially from about 20/80 to 80/20.

The thickness of the mix layer preferably ranges from the thickness corresponding to a single molecule layer to less than the thickness of an organic compound layer, for example, preferably from 1 to 85 nm, more preferably 5 to 60 nm, most preferably 5 to 50 nm.

Preferably the mix layer is formed by a co-deposition process of evaporating the compounds from distinct sources. If both the compounds have equal or very close vapor pressure or evaporation temperature, they may be pre-mixed in a common evaporation boat, from which they are evaporated together. The mix layer is preferably a uniform mixture of both the compounds although the compounds can be present in island form. The light emitting layer is generally formed to a predetermined thickness by evaporating an organic fluorescent material or coating a dispersion thereof in a resin binder.

One exemplary construction of the organic EL light emitting device fabricated using the inventive compound has on a substrate, a hole injecting electrode, a hole injecting and transporting layer, a light emitting and electron injecting and transporting layer, and an electron injecting electrode in the described order. If desired, an auxiliary electrode and a sealing layer are provided on the electron injecting electrode.

The organic EL device of the invention is not limited to the above exemplary construction and may have various other constructions. In another exemplary construction, the light emitting layer is provided singly and an electron injecting and transporting layer is interposed between the light emitting layer and the electron injecting electrode. Also, the light emitting layer may be mixed with the hole injecting and transporting layer, if desired.

The thicknesses of the light emitting layer, hole injecting and transporting layer, and electron injecting and transporting layer are not critical and vary with a particular formation technique. Usually a single layer is about 5 to 500 nm thick, especially about 10 to 300 nm thick.

The thicknesses of the hole injecting and transporting layer and electron injecting and transporting layer are equal to or range from 1/10 to 10 times the thickness of the light emitting layer although they depend on the design of a recombination/light emitting region. When the electron or hole injecting and transporting layer is divided into an injecting layer and a transporting layer, preferably the injecting layer is at least 1 nm thick and the transporting layer is at least 1 nm thick. The upper limit of thickness is generally about 500 nm for the injecting layer and about 500 nm for the transporting layer. The same applies when two injecting and transporting layers are provided.

The hole injecting and transporting layer has functions of facilitating injection of holes from the hole injecting electrode, transporting them stably, and obstructing electrons. The electron injecting and transporting layer has functions of facilitating injection of electrons from the electron injecting electrode, transporting them stably, and obstructing holes. These layers are effective for increasing the number of holes and electrons injected into the light emitting layer and confining holes and electrons therein for optimizing the recombination region to improve light emission efficiency.

In the hole injecting and transporting layer, there may be used various organic compounds as described, for example, in JP-A 63-295695, 2-191694, 3-792, 5-234681, 5-239455, 5-299174, 7-126225, 7-126226, and 8-100172, and EP 0650955A1. Exemplary are tetraarylbenzidine compounds (triaryldiamines or triphenyldiamines: TPD), aromatic tertiary amines, hydrazone derivatives, carbazole derivatives, triazole derivatives, imidazole derivatives, oxadiazole derivatives having an amino group, and polythiophenes. Two or more of these compounds may be used, and on such combined use, they may be formed as separate layers or mixed.

Where the hole injecting and transporting layer is formed separately as a hole injecting layer and a hole transporting layer, two or more compounds are selected in a proper combination from the compounds commonly used in hole injecting and transporting layers. In this regard, it is preferred to laminate layers in such an order that a layer of a compound having a lower ionization potential may be disposed adjacent the hole injecting electrode (ITO). It is also preferred to use a compound having good thin film forming ability at the hole injecting electrode surface. The order of lamination also applies where a plurality of hole injecting and transporting layers are provided. Such an order of lamination is effective for lowering the drive voltage and preventing current leakage and the development and growth of dark spots. Since evaporation is utilized in the manufacture of devices, films as thin as about 1 to 10 nm can be formed uniform and pinhole-free, which restrains any change in color tone of light emission and a drop of efficiency by re-absorption even if a compound having a low ionization potential and absorption in the visible range is used in the hole injecting layer. Like the light emitting layer, the hole injecting and transporting layer may be formed by evaporating the above-mentioned compounds.

In the electron injecting and transporting layer which is optionally provided, there may be used quinoline derivatives including organic metal complexes having 8-quinolinol or a derivative thereof as a ligand such as tris(8-quinolinolato) aluminum (Alq3), oxadiazole derivatives, perylene derivatives, pyridine derivatives, pyrimidine derivatives, quinoxaline derivatives, diphenylquinone derivatives, and nitro-substituted fluorene derivatives. The electron injecting and transporting layer can also serve as the light emitting layer. In this case, use of tris(8-quinolinolato)aluminum etc. is preferred. Like the light emitting layer, the electron injecting and transporting layer may be formed by evaporation or the like.

Where the electron injecting and transporting layer is formed separately as an electron injecting layer and an electron transporting layer, two or more compounds are selected in a proper combination from the compounds commonly used in electron injecting and transporting layers. In this regard, it is preferred to stack layers in such an order that a layer of a compound having a greater electron affinity may be disposed adjacent the electron injecting electrode. The order of stacking also applies where a plurality of electron injecting and transporting layers are provided.

In forming the hole injecting and transporting layer, the light emitting layer, and the electron injecting and transporting layer, vacuum evaporation is preferably used because homogeneous thin films are available. By utilizing vacuum evaporation, there is obtained a homogeneous thin film which is amorphous or has a crystal grain size of less than 0.1 µm. If the grain size is more than 0.1 µm, uneven light emission would take place and the drive voltage of the device must be increased with a substantial drop of charge injection efficiency.

The conditions for vacuum evaporation are not critical although a vacuum of $10^{-4}$ Pa or lower and a deposition rate of about 0.01 to 1 nm/sec are preferred. It is preferred to successively form layers in vacuum because the successive formation in vacuum can avoid adsorption of impurities on the interface between the layers, thus ensuring better performance. Also, the drive voltage of a device can be reduced and the development and growth of dark spots be restrained.

In the embodiment wherein the respective layers are formed by vacuum evaporation, where it is desired for a single layer to contain two or more compounds, preferably boats having the compounds received therein are individually temperature controlled to achieve co-deposition.

The electron injecting electrode is preferably made of metals, alloys or intermetallic compounds having a work function of up to 4 eV. With a work function of more than 4 eV, the electron injecting efficiency lowers and consequently, the light emission efficiency lowers. Examples of the metal having a work function of up to 4 eV of which the electron injecting electrode film is constructed include alkali metals such as Li, Na and K, alkaline earth metals such as Mg, Ca, Sr and Ba, rare earth metals such as La and Ce, and Al, In, Ag, Sn, Zn, and Zr. Examples of the film-forming alloy having a work function of up to 4 eV include Ag—Mg (Ag: 0.1 to 50 at %), Al—Li (Li: 0.01 to 12 at %), In—Mg (Mg: 50 to 80 at %), and Al—Ca (Ca: 0.01 to 20 at %). These materials may be present alone or in combination of two or more. Where two or more materials are combined, their mixing ratio is arbitrary. It is also acceptable that an oxide or halide of an alkali metal, alkaline earth metal or rare earth metal is thinly deposited and a supporting electrode (auxiliary electrode or wiring electrode) of aluminum etc. is used.

The electron injecting electrode may be formed by evaporation or sputtering.

The electron injecting electrode may have at least a sufficient thickness to effect electron injection, for example, a thickness of at least 0.5 nm, preferably at least 1 nm. Although the upper limit is not critical, the electrode thickness is typically about 1 to about 500 nm.

The hole injecting electrode is preferably formed of such a material to such a thickness that the electrode may have a transmittance of at least 80% of emitted light. Illustratively, oxide transparent conductive thin films are preferred. For example, materials based on tin-doped indium oxide (ITO), zinc-doped indium oxide (IZO), indium oxide ($In_2O_3$), tin oxide ($SnO_2$) or zinc oxide (ZnO) are preferable. These oxides may deviate somewhat from their stoichiometry. An appropriate proportion of $SnO_2$ mixed with $In_2O_3$ is about 1 to 20%, more preferably about 5 to 12% by weight. An appropriate proportion of $ZnO_2$ mixed with $In_2O_3$ is about 12 to 32% by weight.

The hole injecting electrode should preferably have a light transmittance of at least 80%, especially at least 90% in the light emission band, typically from 350 to 800 nm, and especially at each light emission. Since the emitted light is generally taken out through the hole injecting electrode, with a lower transmittance, the light emitted by the light emitting layer would be attenuated through the electrode, failing to provide a luminance necessary as a light emitting device. It is noted that only the side from which the emitted light exits has a transmittance of at least 80%.

The hole injecting electrode has at least a sufficient thickness to effect hole injection, preferably a thickness of 50 to 500 nm, especially 50 to 300 nm. Although the upper limit of the electrode thickness is not critical, a too thick electrode would have the risk of separation. Too thin an electrode would have problems with respect to film strength during fabrication, hole transporting ability, and resistance value.

In depositing the hole injecting electrode, a sputtering process is preferred. The sputtering process may be a high-frequency sputtering process using an RF power supply although a dc sputtering process is preferably used when the ease of control of physical properties of the hole injecting electrode being deposited and the flatness of the deposited film are taken into account.

A protective film may be formed if necessary. The protective film may be formed using an inorganic material such as SiOx or an organic material such as Teflon. The protective film may be either transparent or opaque and have a thickness of about 50 to 1,200 nm. Apart from the reactive sputtering process mentioned above, the protective film may also be formed by an ordinary sputtering or evaporation process.

Further, a sealing layer is provided on the device in order to prevent the organic layers and electrodes from oxidation. In order to prevent the ingress of moisture, the sealing layer is formed by attaching a sealing plate such as a glass plate to the substrate with an adhesive resin layer such as a commercially available low moisture absorption photo-curable adhesive, epoxy base adhesive, silicone base adhesive, or crosslinking ethylene-vinyl acetate copolymer adhesive sheet. Metal plates and plastic plates may also be used instead of the glass plate.

Transparent or translucent materials such as glass, quartz and resins are used as the substrate when the emitted light exits from the substrate side. The substrate may be provided with a color filter film, a fluorescent material-containing color conversion film or a dielectric reflecting film for controlling the color of light emission. In the case of the inversely stacked layer structure, the substrate may be either transparent or opaque. For the opaque substrate, ceramic and other materials may be used.

The color filter film used herein may be a color filter as used in liquid crystal displays and the like. The properties of a color filter may be adjusted in accordance with the light emission of the organic EL device so as to optimize the extraction efficiency and color purity.

It is also preferred to use a color filter capable of cutting external light of short wavelength which is otherwise absorbed by the EL device materials and fluorescence conversion layer, because the light resistance and display contrast of the device are improved.

An optical thin film such as a dielectric multilayer film may be used instead of the color filter.

The fluorescence conversion filter film is to convert the color of light emission by absorbing electroluminescence and allowing the fluorescent material in the film to emit light. It is formed from three components: a binder, a fluorescent material, and a light absorbing material.

The fluorescent material used may basically have a high fluorescent quantum yield and desirably exhibits strong absorption in the electroluminescent wavelength region. In practice, laser dyes are appropriate. Use may be made of rhodamine compounds, perylene compounds, cyanine compounds, phthalocyanine compounds (including sub-phthalocyanines), naphthalimide compounds, fused ring hydrocarbon compounds, fused heterocyclic compounds, styryl compounds, and coumarin compounds.

The binder is selected from materials which do not cause extinction of fluorescence, preferably those materials which can be finely patterned by photolithography or printing technique. Also, those materials which are not damaged during deposition of ITO are preferable.

The light absorbing material is used when the light absorption of the fluorescent material is short and may be omitted if unnecessary. The light absorbing material may also be selected from materials which do not cause extinction of fluorescence of the fluorescent material.

Referring to FIG. 1, there is illustrated one exemplary construction of the organic EL device fabricated according to the invention. The organic EL device is shown in FIG. 1 as having on a substrate 1, a hole injecting electrode 2, a hole injecting and transporting layer 3, a light emitting layer 4, an electron injecting and transporting layer 5, and an electron injecting electrode 6 in the described order. The organic EL device of the invention is not limited to the illustrated construction and various other constructions are possible.

The organic EL device of the invention is generally of the dc or pulse drive type while it can be of the ac drive type. The applied voltage is generally about 2 to 30 volts.

EXAMPLE

Examples of the present invention are given below together with Comparative Examples for further illustrating the invention.

Synthetic Example 1

Synthesis of 5,12-bis(2-Naphthyl)-6,11-diphenylnaphthacene (Illustrative Compound I-85)

Boron tribromide was added over one hour to a mixed solution of 5.2 g (33.3 mmol) of naphthoquinone and 10 g (37 mmol) of 1,3-diphenylisobenzofuran in methylene chloride, yielding 7.1 g of 6,11-diphenyl-5,11-naphthacenequinone (yellow acicular crystal: 80%).

Next, 2.05 g (5 mmol) of the above-prepared naphthacenequinone and 100 ml of toluene were admitted into a Schlenk flask which had been purged with argon. To this solution, a toluene/ether solution of a lithiation reagent (15 mmol) separately synthesized from a hexane solution of n-butyllithium and 2-bromonaphthalene was added dropwise over one hour. After the completion of addition, the solution was stirred for 12 hours at room temperature and poured into an ice bath. The reaction solution was extracted 5 times with toluene, washed with water, and dried over magnesium sulfate. After the solvent was distilled off, the reminder was washed with methanol and hexane, yielding 2.4 g of a diol product (white powder: 71%), from which 1.3 g of an end product of the following structure was obtained (red solid: 76%). Sublimation of 1 g of the end product left 0.8 g of a red solid. The results of analysis of the resulting red solid are shown below.

(CF 14)

I-85

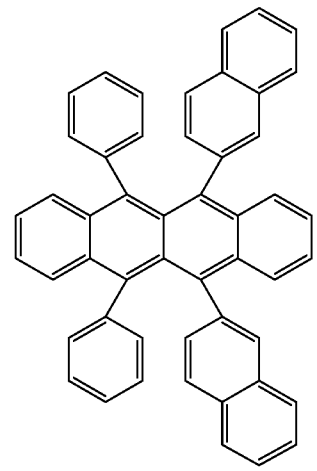

Figure 2:
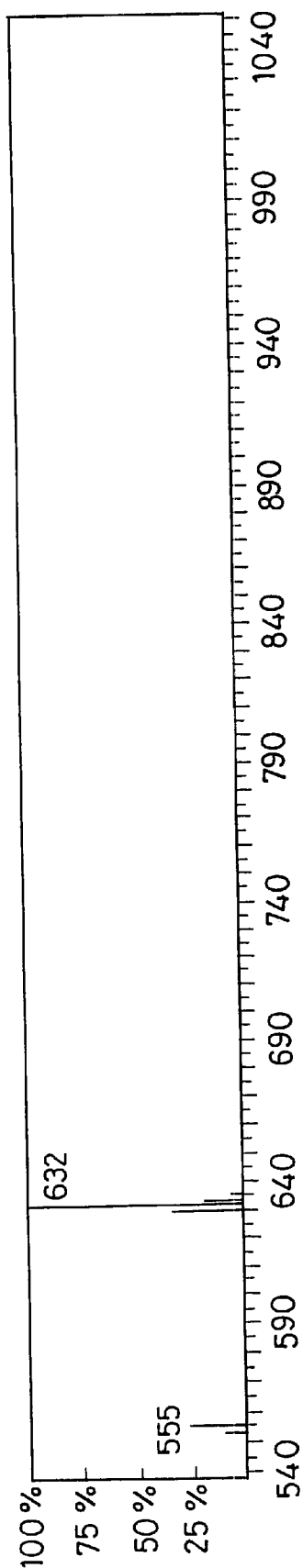
FIG. 2 is a diagram showing a mass analysis spectrum of compound I-85 according to the invention.
Figure 3:
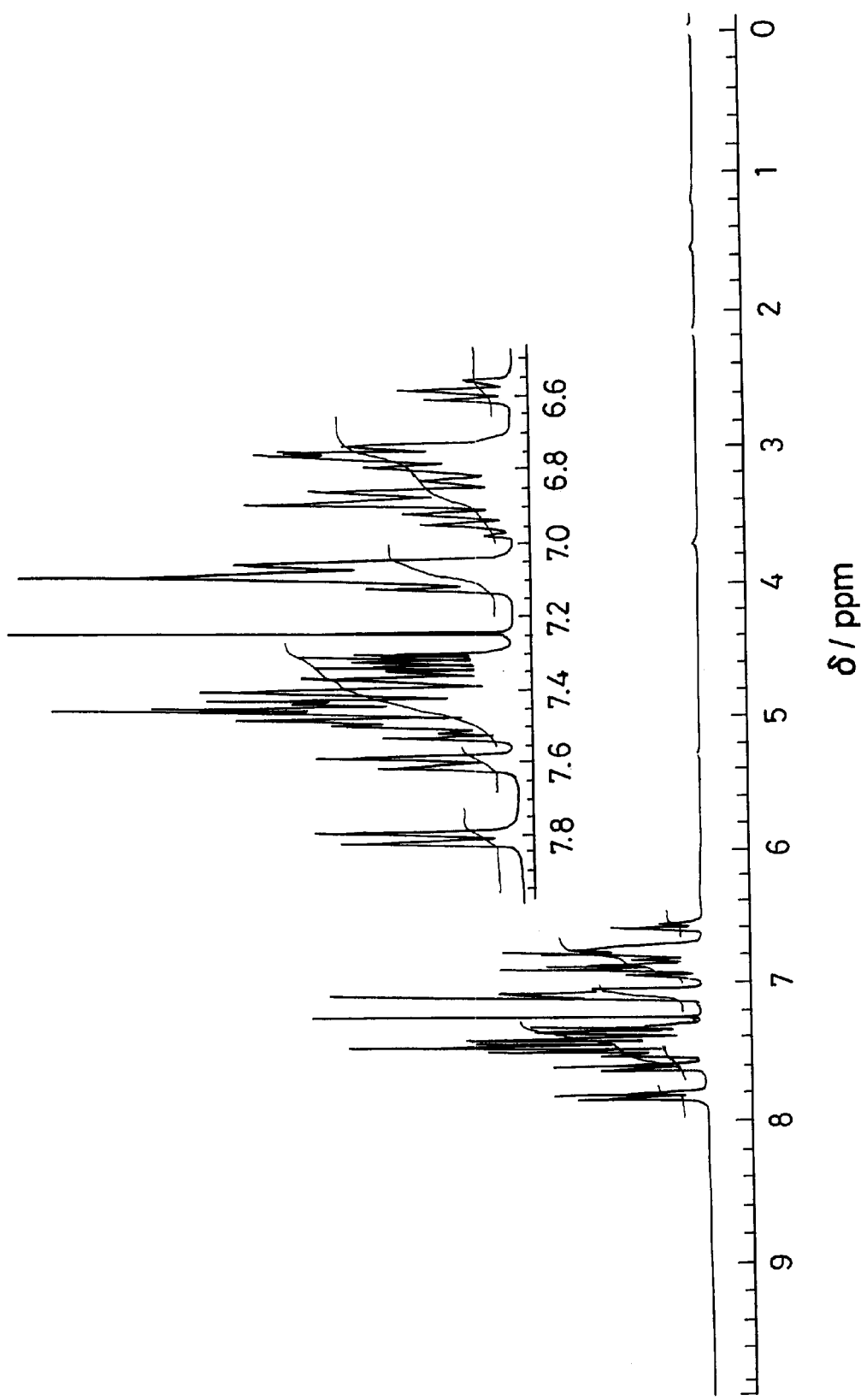
FIG. 3 is a diagram showing a $^1$H-NMR spectrum of compound I-85 according to the invention.
Figure 4:
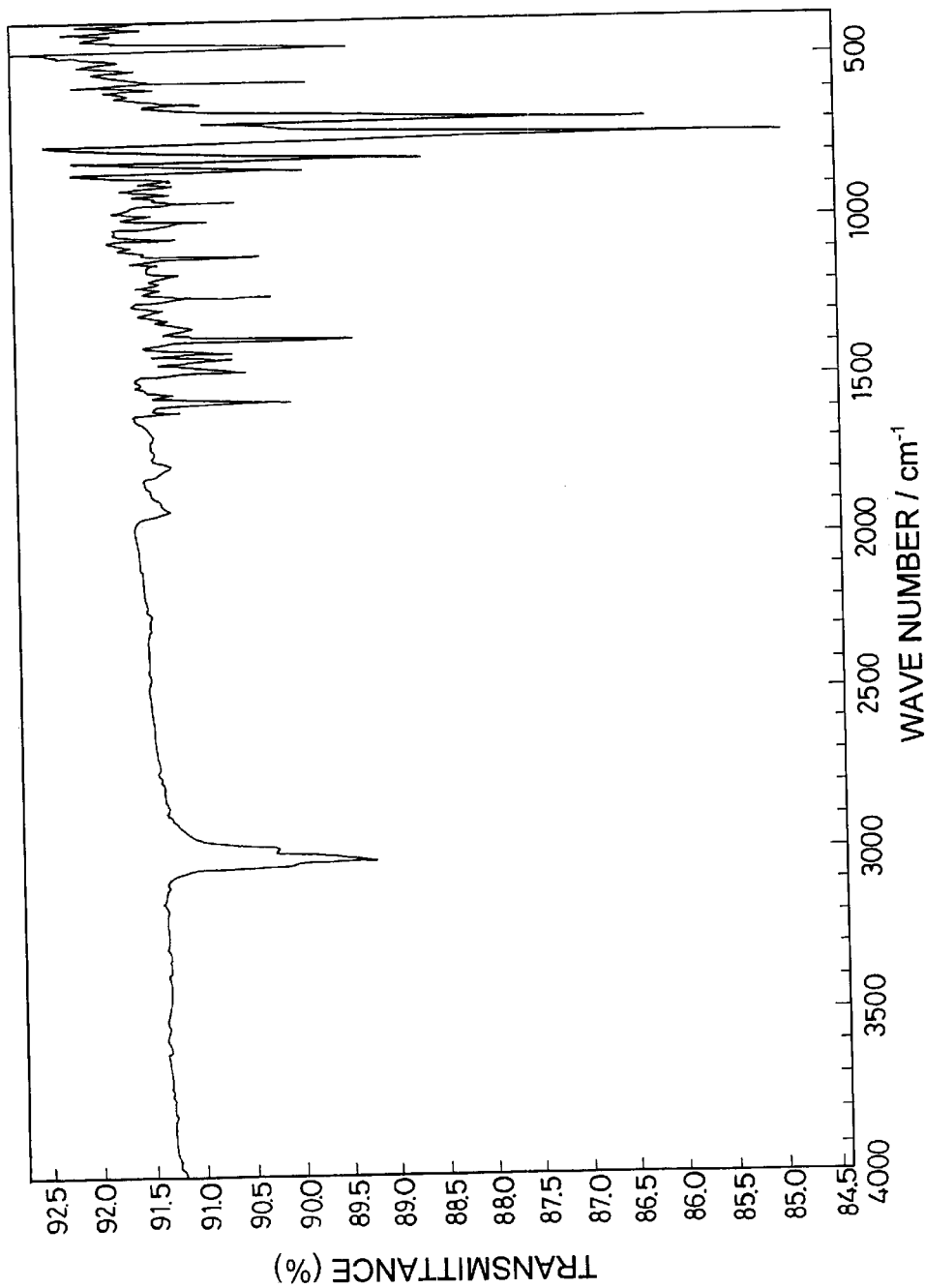
FIG. 4 is a diagram showing an infrared absorption spectrum of compound I-85 according to the invention.

Mass analysis: m/e 632 (M$^+$) (the spectrum shown in FIG. 2); $^1$H-NMR spectrum: shown in FIG. 3; Infrared absorption spectrum: shown in FIG. 4.

Synthetic Example 2

Synthesis of 5,12-diphenyl-6,11-triphenylaminonaphthacene (Illustrative Compound II-40)

By following the same reaction procedure as in Synthetic Example 1, but using 6,11-diphenyl-5,11- naphthacenequinone and p-diiodobenzene, there was yielded 2.2 g of a diol product (white powder: 67%), from which 1.3 g of 5,12-bis(4-iodophenyl)-6,11-diphenylnaphthacene was obtained (red solid: 62%).

Next, Ullman reaction was carried out using 1.2 g (1.5 mmol) of the above-prepared iodide, 1.0 g (6.0 mmol) of diphenylamine, 0.5 g of copper powder, 1.5 g of potassium carbonate, and 10 cm$^3$ of decalin, yielding 0.9 g of 5,12-diphenyl-6,11-triphenylaminonaphthacene of the following structure (red solid: 68%). Sublimation of 0.9 g of the red solid for purification left 0.8 g of a red solid. The results of analysis of the resulting red solid are shown below.

(CF 15)

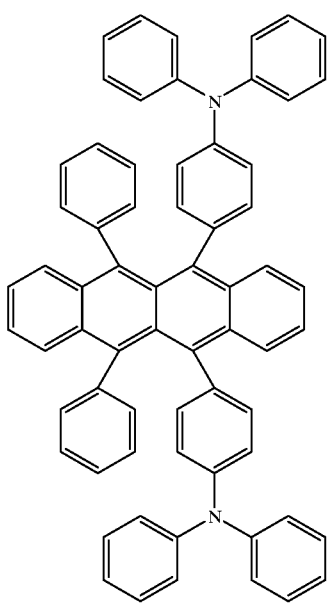

II-40

Figure 5:
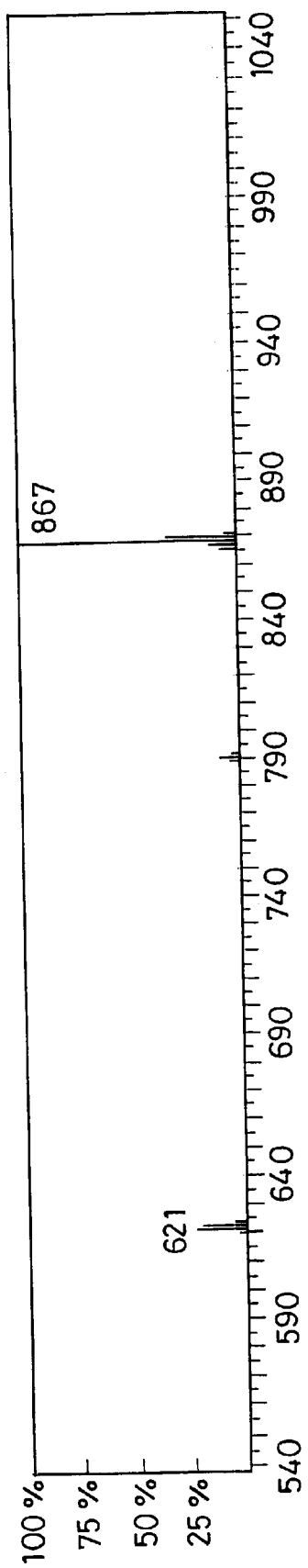
FIG. 5 is a diagram showing a mass analysis spectrum of compound II-40 according to the invention.
Figure 6:
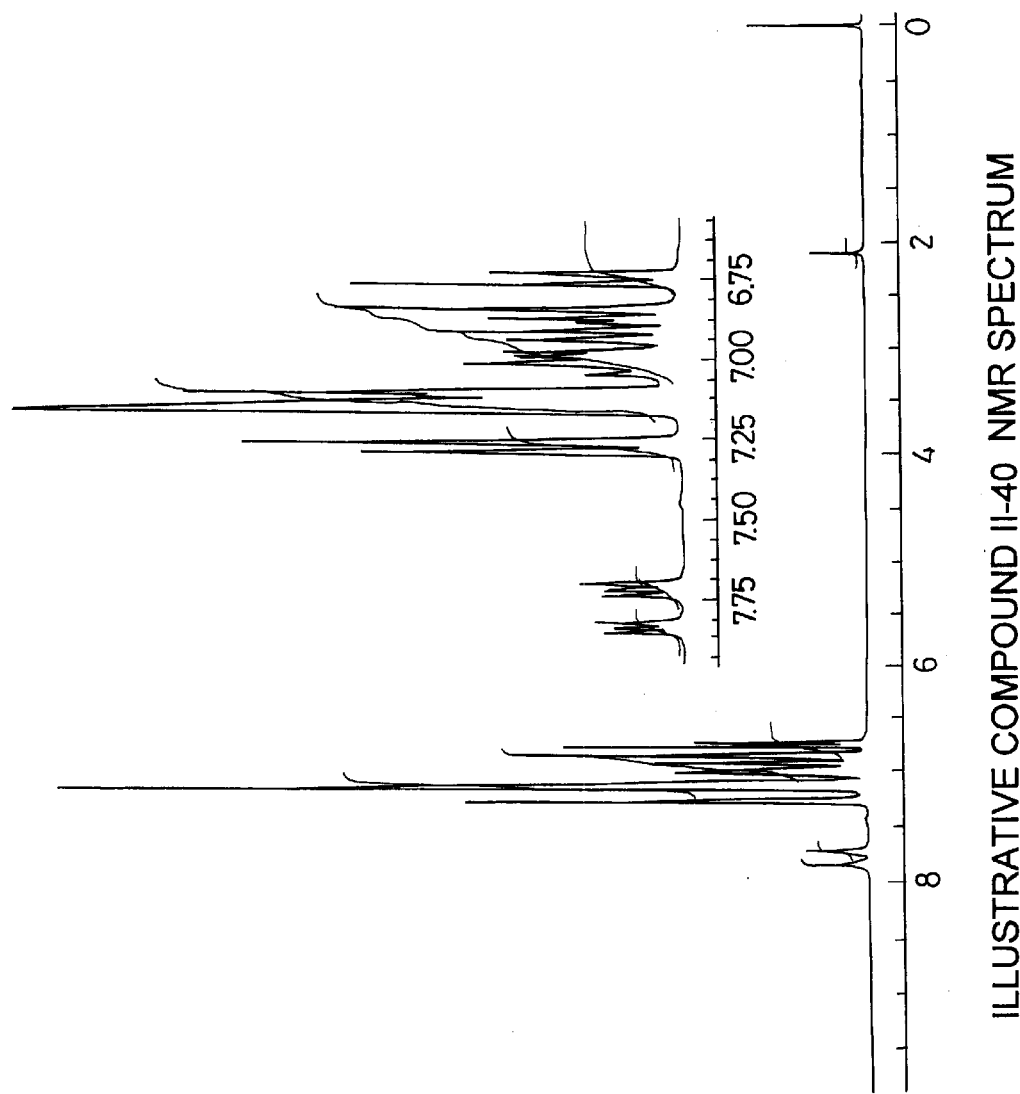
FIG. 6 is a diagram showing a $^1$H-NMR spectrum of compound II-40 according to the invention.
Figure 7:
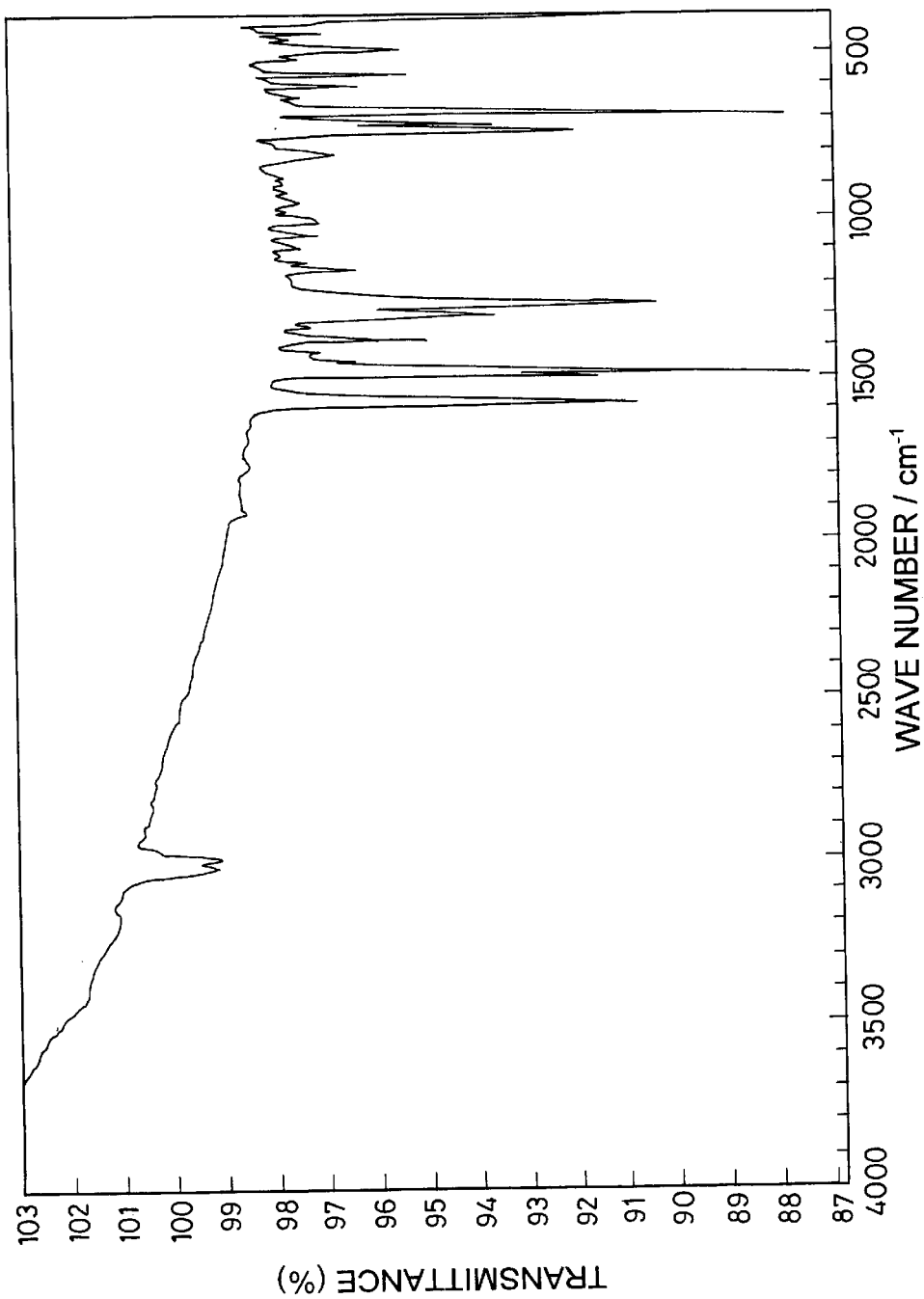
FIG. 7 is a diagram showing an infrared absorption spectrum of compound II-40 according to the invention.

Mass analysis: m/e 868 (M$^+$) (the spectrum shown in FIG. 5); $^1$H-NMR spectrum: shown in FIG. 6; Infrared absorption spectrum: shown in FIG. 7.

Synthetic Example 3

Synthesis of 5,12-diphenyl-6,11-bis(triphenylethenyl)naphthacene (Illustrative Compound III-38)

By following the same reaction procedure as in Synthetic Example 1, but using 6,11-diphenyl-5,11-naphthacenequinone and 2-bromo-1,1,2-triphenylethylene, there was yielded 2.2 g of a diol product (white powder: 68%), from which 1.4 g of an end product of the following structure was obtained (red solid: 72%). Sublimation of 0.9 g of the red solid for purification left 0.8 g of a red solid. The results of analysis of the resulting red solid are shown below.

(CF 16)

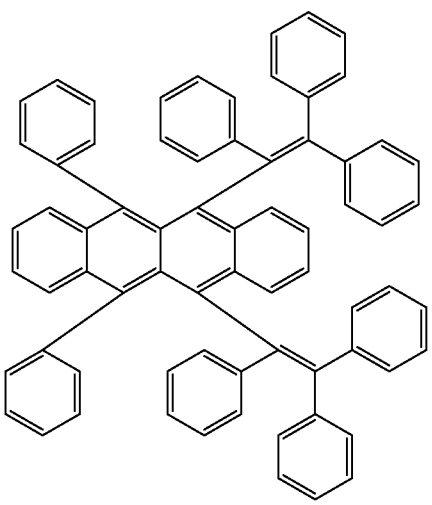

III-38

Figure 8:
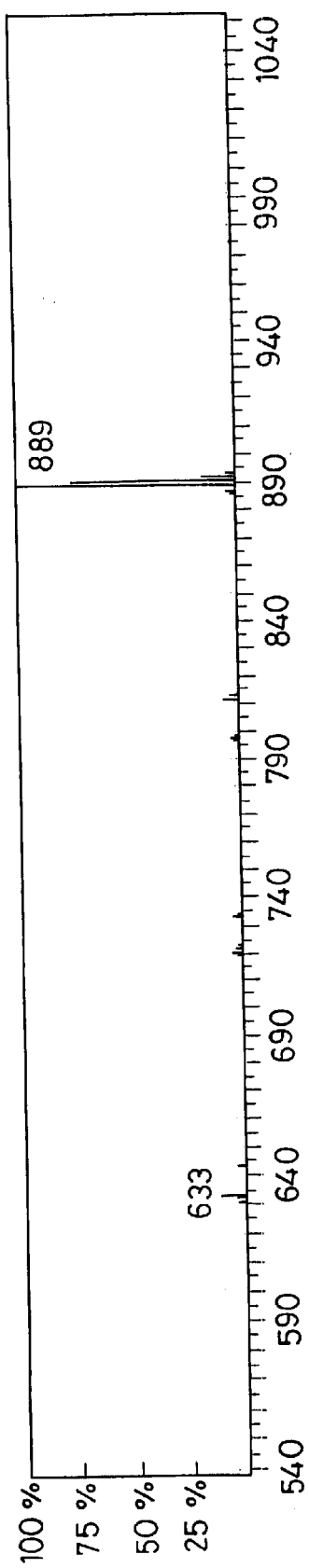
FIG. 8 is a diagram showing a mass analysis spectrum of compound III-38 according to the invention.
Figure 9:
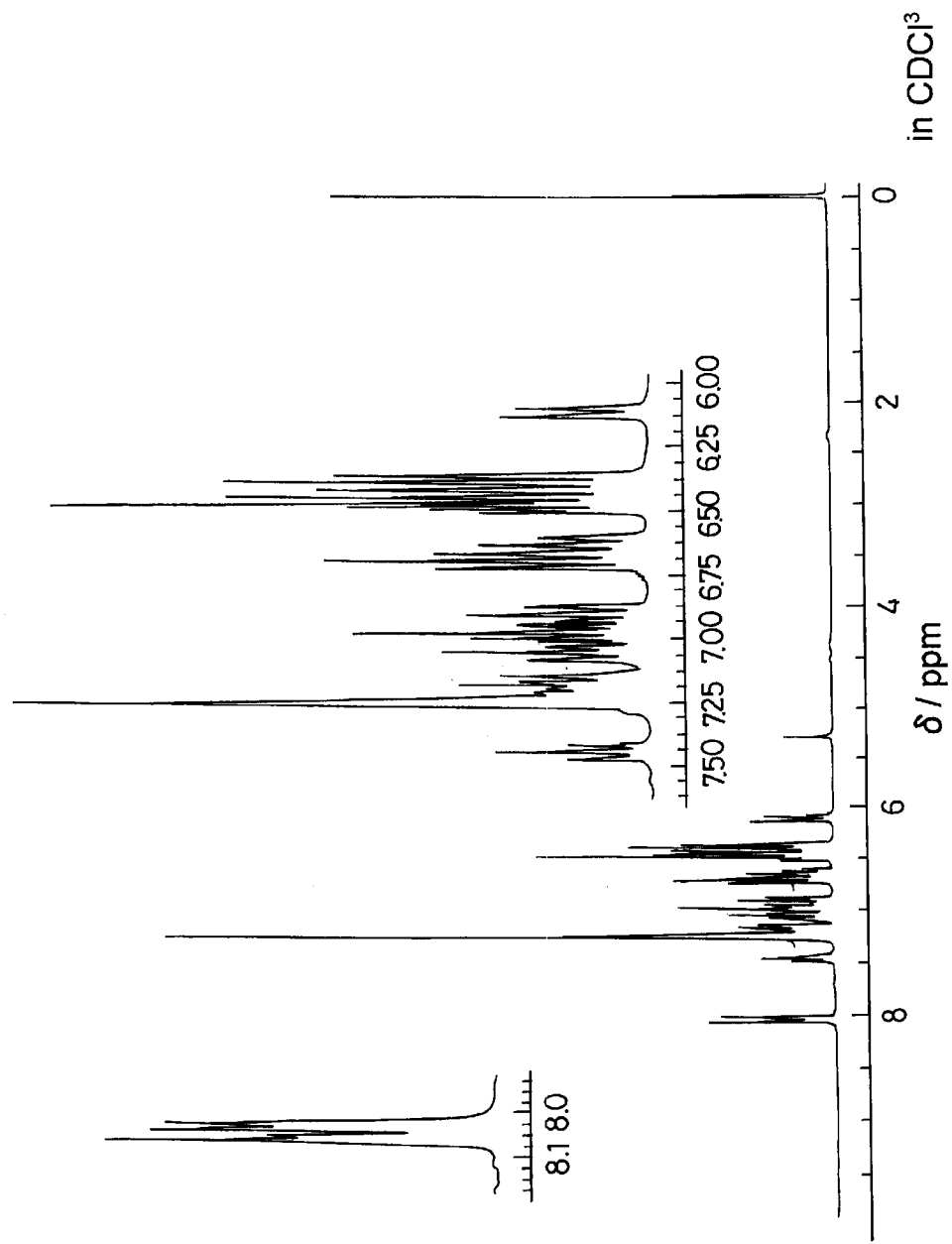
FIG. 9 is a diagram showing a $^1$H-NMR spectrum of compound III-38 according to the invention.
Figure 10:
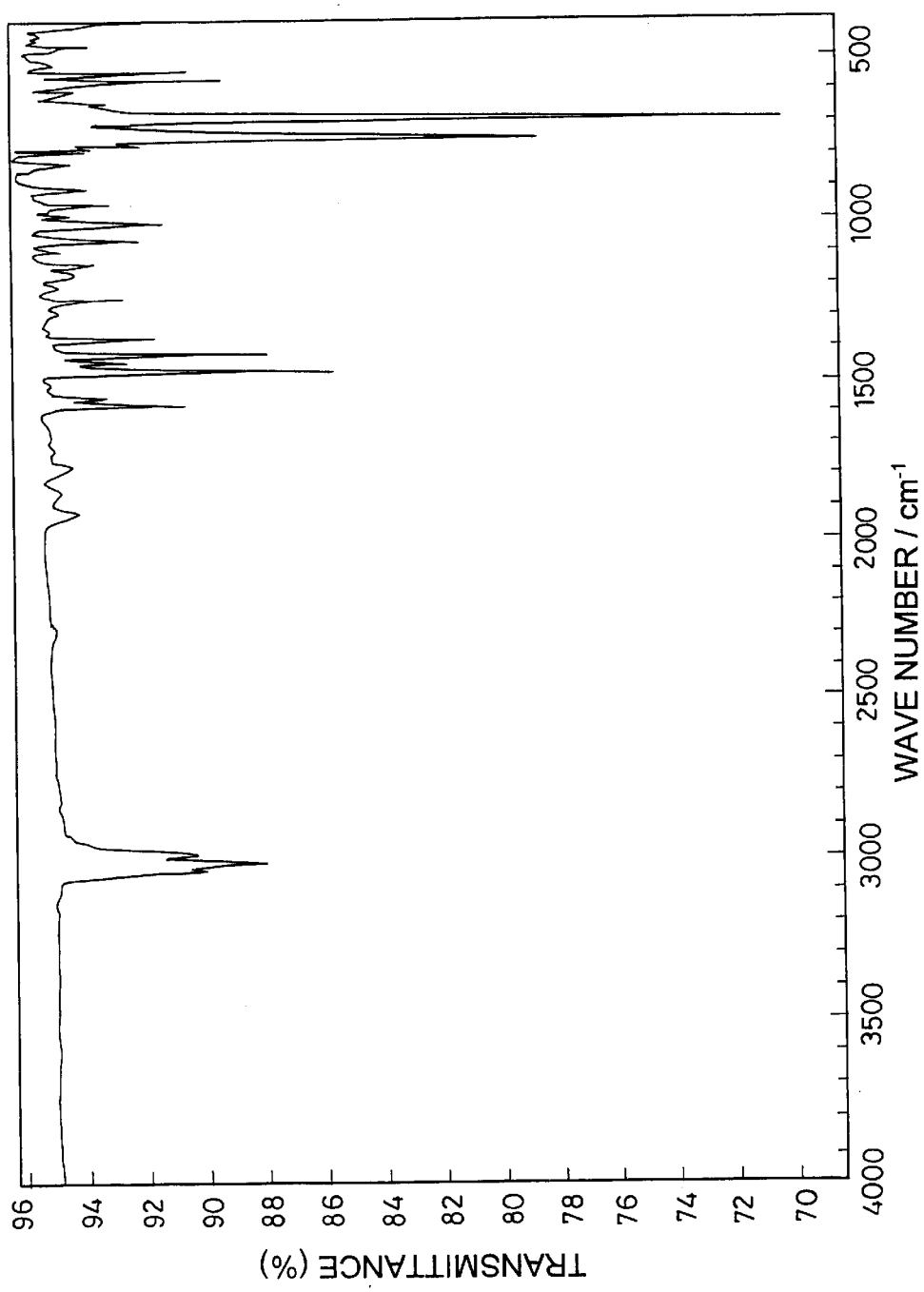
FIG. 10 is a diagram showing an infrared absorption spectrum of compound III-38 according to the invention.

Mass analysis: m/e 889 ((M+1)$^+$) (the spectrum shown in FIG. 8); $^1$H-NMR spectrum: shown in FIG. 9; Infrared absorption spectrum: shown in FIG. 10.

Example 1

On a glass substrate, a transparent ITO electrode thin film was deposited to a thickness of 100 nm by RF sputtering and patterned. The glass substrate having the transparent ITO electrode was subjected to ultrasonic washing with neutral detergent, acetone, and ethanol, pulled up from boiling ethanol, and dried. The transparent electrode surface was further cleaned with UV/ozone. Thereafter, the substrate was secured by a holder in a vacuum evaporation chamber, which was evacuated to a vacuum of 1×10$^{-4}$ Pa or lower.

With the vacuum kept, N,N'-diphenyl-N,N'-bis[N-(4-methylphenyl)-N-phenyl-(4-aminophenyl)]-1,1'-biphenyl-4,4'-diamine was evaporated at a deposition rate of 0.2 nm/sec. to a thickness of 50 nm, forming a hole injecting layer.

Then, N,N,N',N'-tetrakis(m-biphenyl)-1,1'-biphenyl-4,4'-diamine (TPD) was evaporated at a deposition rate of 0.2 nm/sec to a thickness of 20 nm, forming a hole transporting layer.

With the vacuum kept, the compound of the following structure according to the invention (Illustrative Compound I-33) and tris(8-quinolinolato)aluminum (Alq3) were evaporated in a weight ratio of 2:100 and at an overall deposition rate of 0.2 nm/sec to a thickness of 70 nm, forming an electron injecting and transporting/light emitting layer.

(CF 17)

III-33

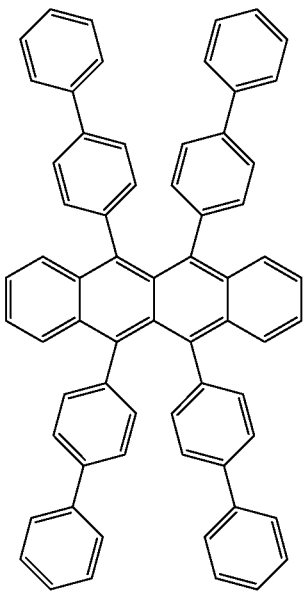

Next, with the vacuum kept, Mg—Ag (weight ratio 10:1) was evaporated at a deposition rate of 0.2 nm/sec to a thickness of 200 nm, forming an electron injecting electrode. Finally, aluminum was evaporated to a thickness of 100 nm to form a protective electrode, completing an organic EL device.

A dc voltage was applied across the organic EL device. Initially, the device was found to produce light emission at a current density of 10 mA/cm² and a drive voltage of 8.8 volts to a luminance of 810 cd/m². The light emission had a maximum wavelength λmax of 570 nm and chromaticity coordinates (x, y) of (0.53, 0.46).

While the device was operated to continue light emission with a constant current of 10 mA/Cm² conducted, measurement was made by means of a luminance meter equipped with a red filter for LCD, finding emission of red light at a luminance of 150 cd/m², a maximum wavelength λmax of 620 nm, and chromaticity coordinates (x, y) of (0.66, 0.34). The red filter used herein was to cut wavelengths of shorter than 590 nm and had a transmittance of 30% at a wavelength of 600 nm.

The device was continuously operated for light emission with a constant current of 50 mA/cm² conducted. It exhibited an extended life as demonstrated by a luminance half-life period of more than 2,700 hours.

Example 2

An organic EL device was fabricated as in Example 1 except that the compound used along with Alq3 in the electron injecting and transporting/light emitting layer was changed to the compound of the following structure (Illustrative Compound I-17).

(CF 18)

I-17

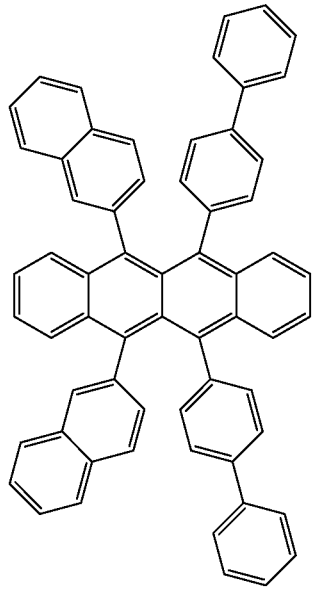

A dc voltage was applied across the organic EL device. The device was found to produce light emission at a current density of 10 mA/cm² and a drive voltage of 8.6 volts to a luminance of 820 cd/m². The light emission had a maximum wavelength λmax of 575 nm and chromaticity coordinates (x, y) of (0.53, 0.46).

Measurement was similarly made using the same red filter as in Example 1, finding emission of red light at a luminance of 155 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 2,700 hours.

Example 3

An organic EL device was fabricated as in Example 1 except that the compound used along with Alq3 in the electron injecting and transporting/light emitting layer was changed to the compound of the following structure (Illustrative Compound I-223).

(CF 19)

I-223

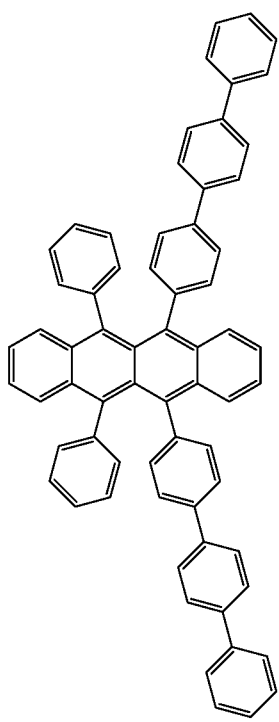

A dc voltage was applied across the organic EL device. The device was found to produce light emission at a current density of 10 mA/cm² and a drive voltage of 9.0 volts to a luminance of 850 cd/m². The light emission had a maximum wavelength λmax of 576 nm and chromaticity coordinates (x, y) of (0.53, 0.46).

Measurement was similarly made using the same red filter as in Example 1, finding emission of red light at a luminance of 165 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 3,000 hours.

Example 4

An organic EL device was fabricated as in Example 1 except that the compound used along with Alq3 in the electron injecting and transporting/light emitting layer was changed to the compound of the following structure (Illustrative Compound I-273).

(CF 20)

I-273

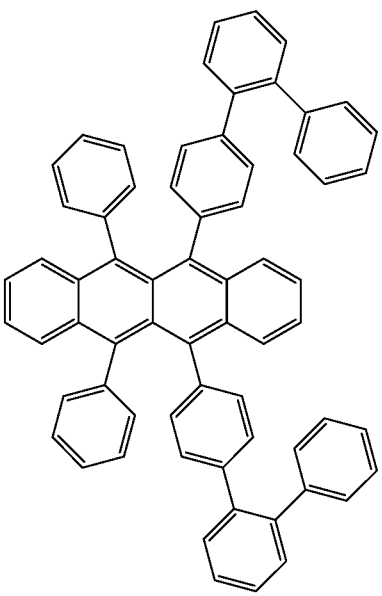

A dc voltage was applied across the organic EL device. The device was found to produce light emission at a current density of 10 mA/cm² and a drive voltage of 8.8 volts to a luminance of 810 cd/m². The light emission had a maximum wavelength λmax of 573 nm and chromaticity coordinates (x, y) of (0.53, 0.46).

Measurement was similarly made using the same red filter as in Example 1, finding emission of red light at a luminance of 155 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 2,700 hours.

Example 5

An organic EL device was fabricated as in Example 1 except that the compound used along with Alq3 in the electron injecting and transporting/light emitting layer was changed to the compound of the following structure (Illustrative Compound I-226).

(CF 21)

I-226

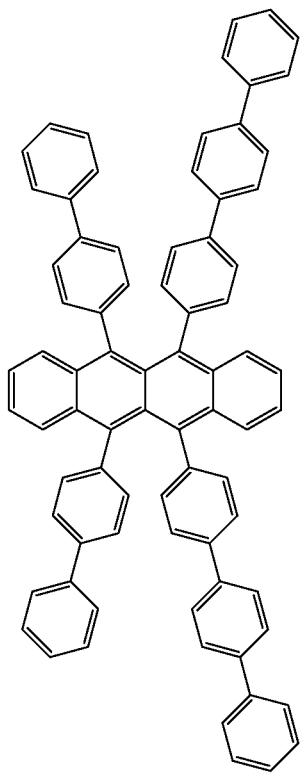

A dc voltage was applied across the organic EL device. The device was found to produce light emission at a current density of 10 mA/cm² and a drive voltage of 8.7 volts to a luminance of 855 cd/m². The light emission had a maximum wavelength µmax of 575 nm and chromaticity coordinates (x, y) of (0.53, 0.46).

Measurement was similarly made using the same red filter as in Example 1, finding emission of red light at a luminance of 162 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 3,000 hours.

Example 6

An organic EL device was fabricated as in Example 1 except that the compound used along with Alq3 in the electron injecting and transporting/light emitting layer was changed to the compound of the following structure (Illustrative Compound II-86).

(CF 22)

II-86

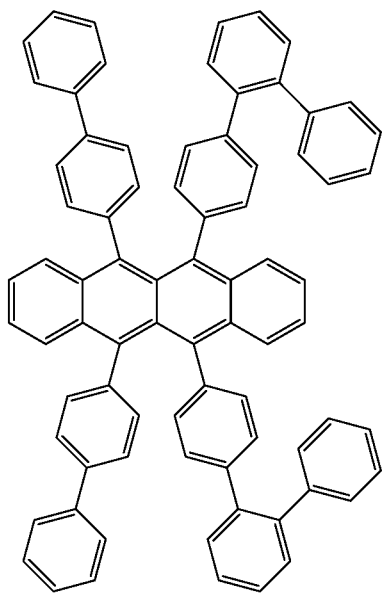

A dc voltage was applied across the organic EL device. The device was found to produce light emission at a current density of 10 mA/cm² and a drive voltage of 9.1 volts to a luminance of 830 cd/m². The light emission had a maximum wavelength λmax of 575 nm and chromaticity coordinates (x, y) of (0.53, 0.46).

Measurement was similarly made using the same red filter as in Example 1, finding emission of red light at a luminance of 157 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 2,700 hours.

Example 7

Organic EL devices were fabricated as in Example 1 except that the compound used along with Alq3 in the electron injecting and transporting/light emitting layer was changed to the compounds shown in Tables 1 to 33 other than the Illustrative Compounds used in the foregoing Examples, obtaining substantially the same results.

Example 8

An organic EL device was fabricated as in Example 1 except that TPD and the compound of the following structure (Illustrative Compound I-33) were evaporated in a weight ratio of 2:100 when the hole injecting and transporting layer was formed by evaporation, and Alq3 was evaporated as a single layer.

(CF 23)

I-33

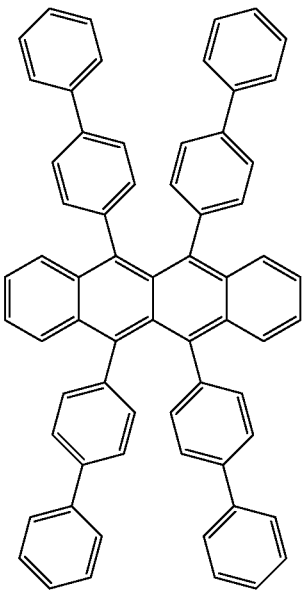

(CF 24)

I-17

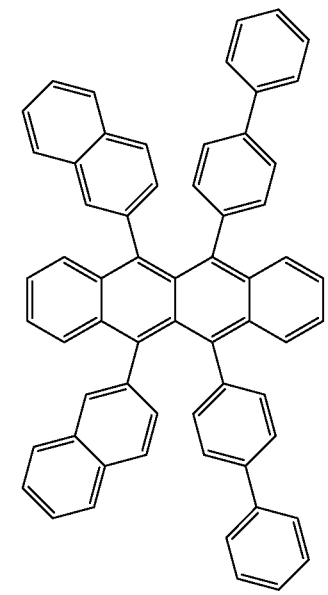

A dc voltage was applied across the organic EL device. The device was found to produce light emission at a current density of 10 mA/cm² and a drive voltage of 5.7 volts to a luminance of 970 cd/m². The light emission had a maximum wavelength λmax of 560 nm and chromaticity coordinates (x, y) of (0.44, 0.53).

Measurement was similarly made using the same red filter as in Example 1, finding emission of red light at a luminance of 145 cd/m², a maximum wavelength λmax of 615 nm, and chromaticity coordinates (x, y) of (0.61, 0.37).

The device was continuously operated for light emission with a constant current of 50 mA/cm² conducted. It exhibited an extended life as demonstrated by a luminance half-life period of more than 2,000 hours.

Example 9

An organic EL device was fabricated as in Example 8 except that the compound used along with TPD in evaporating the hole injecting and transporting layer was changed to the compound of the following structure (Illustrative Compound I-17).

A dc voltage was applied across the organic EL device. The device was found to produce light emission at a current density of 10 mA/cm² and a drive voltage of 5.73 volts to a luminance of 980 cd/m². The light emission had a maximum wavelength λmax of 565 nm and chromaticity coordinates (x, y) of (0.45, 0.53).

Measurement was similarly made using the same red filter as in Example 1, finding emission of red light at a luminance of 140 cd/m², a maximum wavelength λmax of 615 nm, and chromaticity coordinates (x, y) of (0.62, 0.37).

The device was continuously operated for light emission with a constant current of 50 mA/cm² conducted. It exhibited an extended life as demonstrated by a luminance half-life period of more than 1,700 hours.

Example 10

An organic EL device was fabricated as in Example 8 except that the compound used along with TPD in evaporating the hole injecting and transporting layer was changed to the compound of the following structure (Illustrative Compound I-223).

(CF 25)

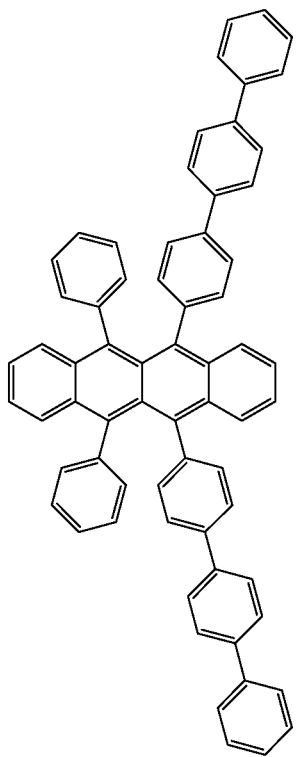

I-223

A dc voltage was applied across the organic EL device. The device was found to produce light emission at a current density of 10 mA/cm² and a drive voltage of 5.65 volts to a luminance of 985 cd/m². The light emission had a maximum wavelength λmax of 565 nm and chromaticity coordinates (x, y) of (0.44, 0.53).

Measurement was similarly made using the same red filter as in Example 1, finding emission of red light at a luminance of 145 cd/m², a maximum wavelength λmax of 615 nm, and chromaticity coordinates (x, y) of (0.62, 0.37).

The device was continuously operated for light emission with a constant current of 50 mA/cm² conducted. It exhibited an extended life as demonstrated by a luminance half-life period of more than 2,000 hours.

Example 11

An organic EL device was fabricated as in Example 8 except that the compound used along with TPD in evaporating the hole injecting and transporting layer was changed to the compound of the following structure (Illustrative Compound I-273).

(CF 26)

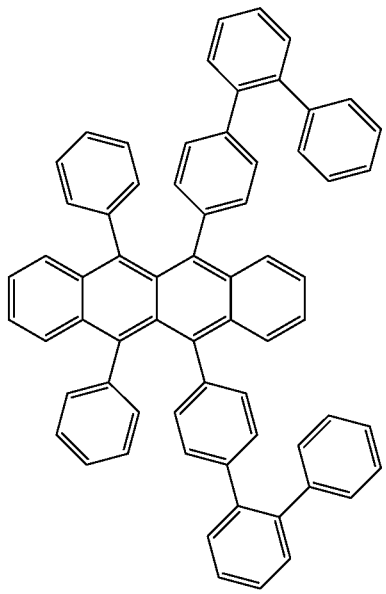

I-273

A dc voltage was applied across the organic EL device. The device was found to produce light emission at a current density of 10 mA/cm² and a drive voltage of 5.65 volts to a luminance of 985 cd/m². The light emission had a maximum wavelength λmax of 565 nm and chromaticity coordinates (x, y) of (0.44, 0.53).

Measurement was similarly made using the same red filter as in Example 1, finding emission of red light at a luminance of 145 cd/m², a maximum wavelength λmax of 615 nm, and chromaticity coordinates (x, y) of (0.62, 0.37).

The device was continuously operated for light emission with a constant current of 50 mA/cm² conducted. It exhibited an extended life as demonstrated by a luminance half-life period of more than 2,000 hours.

Example 12

An organic EL device was fabricated as in Example 8 except that the compound used along with TPD in evaporating the hole injecting and transporting layer was changed to the compound of the following structure (Illustrative Compound I-226).

(CF 27)

I-226

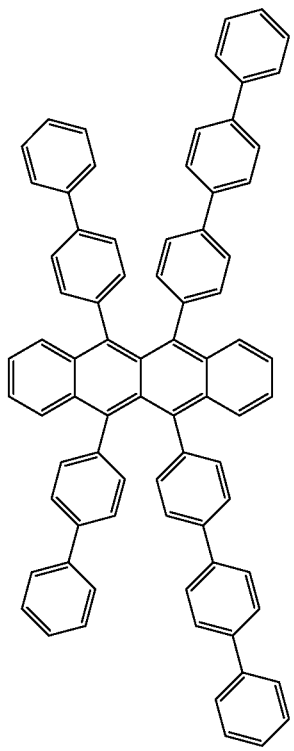

A dc voltage was applied across the organic EL device. The device was found to produce light emission at a current density of 10 mA/cm² and a drive voltage of 5.75 volts to a luminance of 980 cd/m². The light emission had a maximum wavelength λmax of 563 nm and chromaticity coordinates (x, y) of (0.44, 0.53).

Measurement was similarly made using the same red filter as in Example 1, finding emission of red light at a luminance of 140 cd/m², a maximum wavelength λmax of 615 nm, and chromaticity coordinates (x, y) of (0.61, 0.37).

The device was continuously operated for light emission with a constant current of 50 mA/cm² conducted. It exhibited an extended life as demonstrated by a luminance half-life period of more than 2,000 hours.

Example 13

An organic EL device was fabricated as in Example 8 except that the compound used along with TPD in evaporating the hole injecting and transporting layer was changed to the compound of the following structure (Illustrative Compound II-86).

(CF 28)

II-86

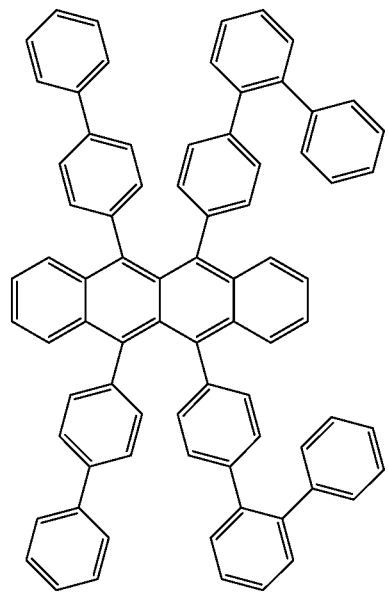

A dc voltage was applied across the organic EL device. The device was found to produce light emission at a current density of 10 mA/cm² and a drive voltage of 5.0 volts to a luminance of 970 cd/m². The light emission had a maximum wavelength λmax of 563 nm and chromaticity coordinates (x, y) of (0.44, 0.53).

Measurement was similarly made using the same red filter as in Example 1, finding emission of red light at a luminance of 140 cd/m², a maximum wavelength λmax of 615 nm, and chromaticity coordinates (x, y) of (0.61, 0.37).

The device was continuously operated for light emission with a constant current of 50 mA/cm² conducted. It exhibited an extended life as demonstrated by a luminance half-life period of more than 2,000 hours.

Example 14

Organic EL devices were fabricated as in Example 10 except that the compound used along with TPD in evaporating the hole injecting and transporting layer was changed to the compounds shown in Tables 1 to 33 other than the Illustrative Compounds used in the foregoing Examples 10 to 13, obtaining substantially the same results.

Example 15

After the hole injecting layer was formed as in Example 1, two compounds of the following structure having different carrier trapping capabilities and N,N,N',N'-tetrakis(m-biphenyl)-1,1'-biphenyl-4,4'-diamine (TPD) were evaporated in a weight ratio of 2:2:100 at a deposition rate of 0.2 nm/sec to a thickness of 40 nm, forming a light emitting layer.

(CF 29)

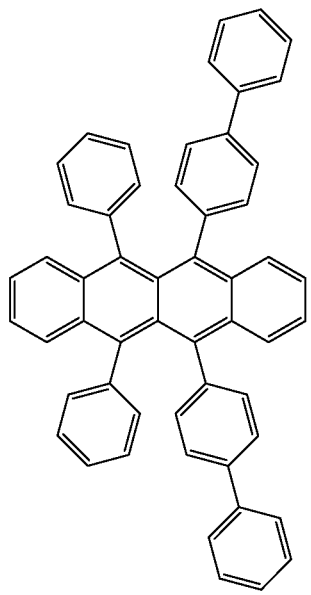

(CF 30)

IV-257

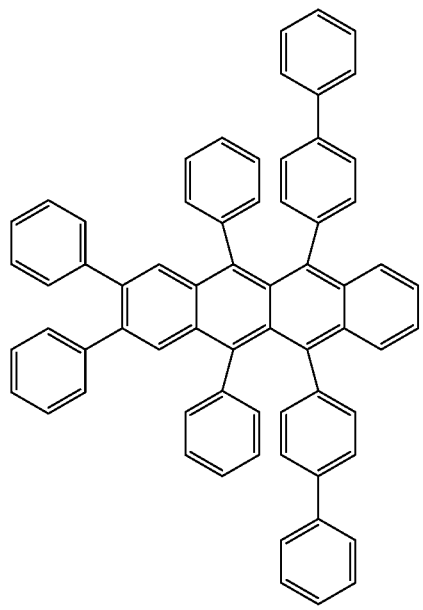

With the vacuum kept, tris(8-quinolinolato)aluminum (Alq3) was evaporated at a deposition rate of 0.2 nm/sec to a thickness of 30 nm, forming an electron injecting and transporting layer.

Subsequently as in Example 1, an electron injecting electrode of Mg—Ag (weight ratio 10:1) and a protective electrode of aluminum were formed, completing an organic EL device.

A dc voltage was applied across the organic EL device. The device was found to produce light emission at a current density of 10 mA/cm² and a drive voltage of 9.2 volts to a luminance of 800 cd/m². The light emission had a maximum wavelength λmax of 580 nm and chromaticity coordinates (x, y) of (0.54, 0.46).

Measurement was similarly made using the same red filter as in Example 1, finding emission of red light at a luminance of 175 cd/m², a maximum wavelength λmax of 620 nm, and chromaticity coordinates (x, y) of (0.66, 0.34).

The device was continuously operated for light emission with a constant current of 50 mA/cm² conducted. It exhibited an extremely extended life as demonstrated by a luminance half-life period of more than 3,000 hours.

Example 16

After the hole injecting layer was formed as in Example 1, two compounds of the following structure having different carrier trapping capabilities and N,N,N',N'-tetrakis(m-biphenyl)-1,1'-biphenyl-4,4'-diamine (TPD) were evaporated in a weight ratio of 2:2:100 at a deposition rate of 0.2 nm/sec to a thickness of 40 nm, forming a light emitting layer.

(CF 31)

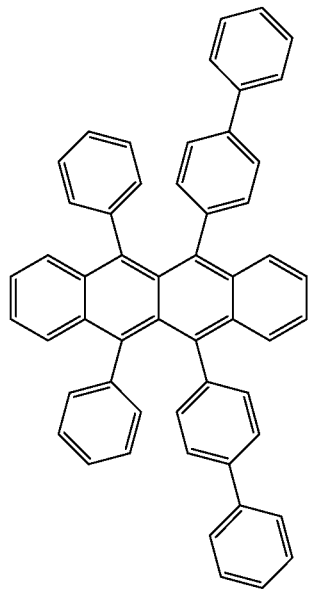

(CF 32)

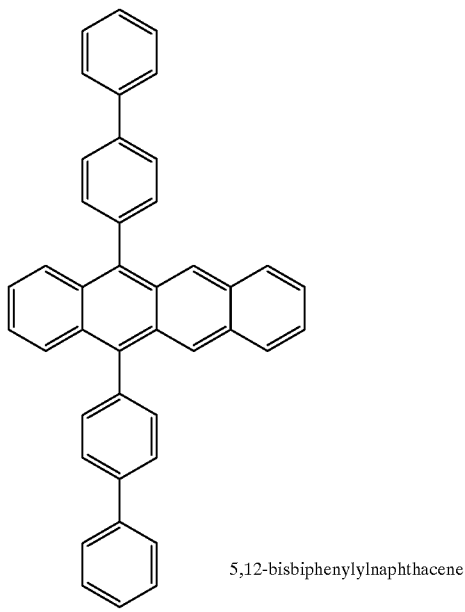

5,12-bisbiphenylylnaphthacene (CF 33)

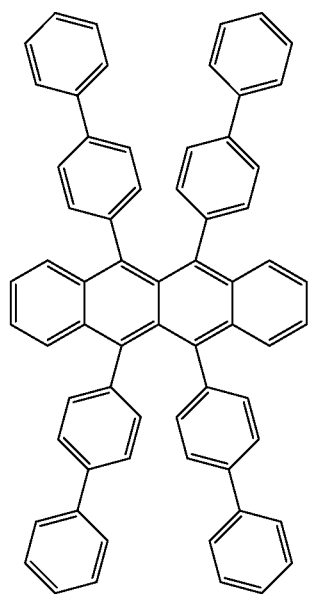

I-33

With the vacuum kept, tris(8-quinolinolato)aluminum (Alq3) was evaporated at a deposition rate of 0.2 nm/sec to a thickness of 30 nm, forming an electron injecting and transporting layer.

Subsequently as in Example 1, an electron injecting electrode of Mg—Ag (weight ratio 10:1) and a protective electrode of aluminum were formed, completing an organic EL device.

A dc voltage was applied across the organic EL device. The device was found to produce light emission at a current density of 10 mA/cm² and a drive voltage of 9.2 volts to a luminance of 850 cd/m². The light emission had a maximum wavelength λmax of 558 nm and chromaticity coordinates (x, y) of (0.54, 0.46).

Measurement was similarly made using the same red filter as in Example 1, finding emission of red light at a luminance of 165 cd/m², a maximum wavelength λmax of 620 nm, and chromaticity coordinates (x, y) of (0.66, 0.34).

The device was continuously operated for light emission with a constant current of 50 mA/cm² conducted. It exhibited an extremely extended life as demonstrated by a luminance half-life period of more than 3,000 hours.

Example 17

After the hole injecting layer was formed as in Example 1, the compound of the following structure (I-33) and 9,9',10,10'-tetra(2-biphenylyl)-2,2'-dianthracene (DPA) having different carrier trapping capabilities were evaporated in a weight ratio of 2:100 at a deposition rate of 0.2 nm/sec to a thickness of 40 nm, forming a light emitting layer.

With the vacuum kept, tris(8-quinolinolato)aluminum (Alq3) was evaporated at a deposition rate of 0.2 nm/sec to a thickness of 15 nm, forming an electron injecting and transporting layer. Otherwise as in Example 1, an organic EL device was fabricated.

A dc voltage was applied across the organic EL device. The device was found to produce light emission at a current density of 10 mA/cm² and a drive voltage of 7.7 volts to a luminance of 1,300 cd/m². The light emission had a maximum wavelength λmax of 570 nm and chromaticity coordinates (x, y) of (0.53, 0.46).

Measurement was similarly made using the same red filter as in Example 1, finding emission of red light at a luminance of 235 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 1,300 hours.

Example 18

After the hole injecting layer was formed as in Example 1, the compound of the following structure (I-223) and 9,9',10,10'-tetra(2-biphenylyl)-2,2'-dianthracene (DPA) having different carrier trapping capabilities were evaporated in a weight ratio of 2:100 at a deposition rate of 0.2 nm/sec to a thickness of 40 nm, forming a light emitting layer.

(CF 34)

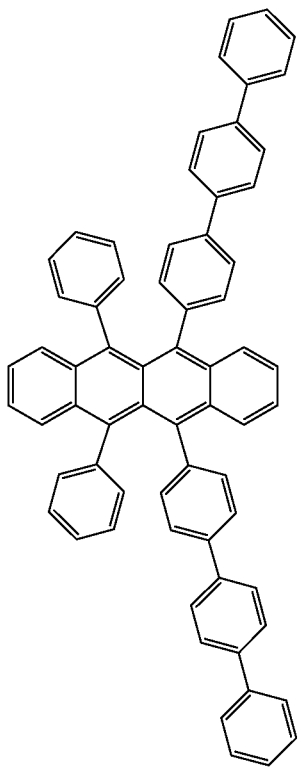

I-223

(CF 35)

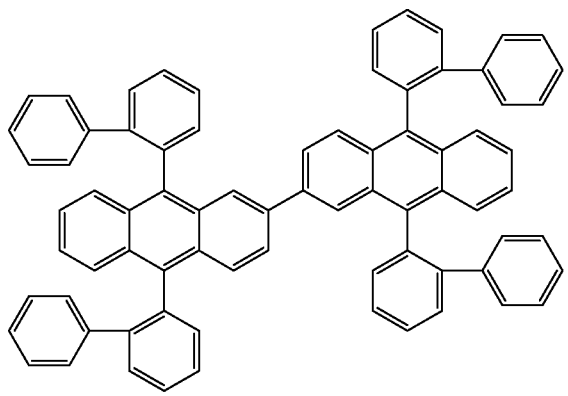

abbreviation: DPA
9,9',10,10'-tetra(2-biphenylyl)-2,2'-dianthracene

With the vacuum kept, tris(8-quinolinolato)aluminum (Alq3) was evaporated at a deposition rate of 0.2 nm/sec to a thickness of 15 nm, forming an electron injecting and transporting layer. Otherwise as in Example 1, an organic EL device was fabricated.

A dc voltage was applied across the organic EL device. The device was found to produce light emission at a current density of 10 mA/cm² and a drive voltage of 7.8 volts to a luminance of 1,250 cd/m². The light emission had a maximum wavelength λmax of 576 nm and chromaticity coordinates (x, y) of (0.53, 0.46).

Measurement was similarly made using the same red filter as in Example 1, finding emission of red light at a luminance of 230 cd/m², a maximum wavelength λmax of 620 nm, and chromaticity coordinates (x, y) of (0.66, 0.34).

The device was continuously operated for light emission with a constant current of 50 mA/cm² conducted. It exhibited an extended life as demonstrated by a luminance half-life period of more than 1,300 hours.

Example 19

When the hole injecting and transporting layer was formed by evaporation in Example 1, the compound to be evaporated along with TPD was changed to the compound of the following structure and they were evaporated at a deposition rate ratio of 100:2, forming a hole injecting and transporting layer.

(CF 36)

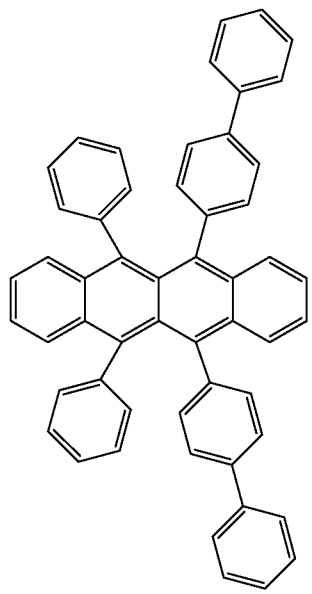

After the hole injecting layer was formed, the compound of the following structure (DPA) and 4,4'-bis(N-phenyl-N-1-naphthyl)aminostilbene having different carrier trapping capabilities were evaporated in a weight ratio of 100:2 at a deposition rate of 0.2 nm/sec to a thickness of 40 nm, forming a light emitting layer.

(CF 37)

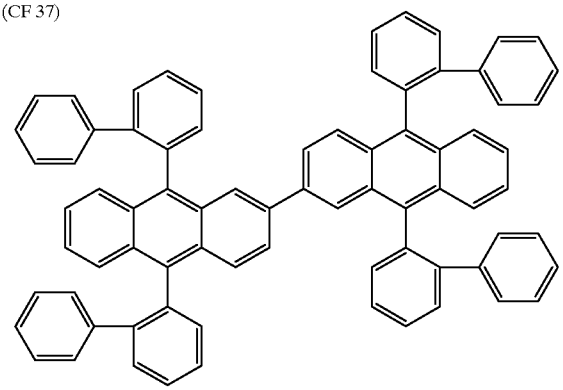

abbreviation: DPA
9,9',10,10'-tetra(2-biphenylyl)-2,2'-dianthracene (CF 38)

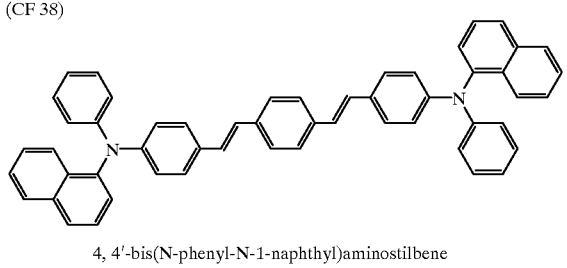

4, 4'-bis(N-phenyl-N-1-naphthyl)aminostilbene

With the vacuum kept, tris(8-quinolinolato)aluminum (Alq3) was evaporated at a deposition rate of 0.2 nm/sec to a thickness of 20 nm, forming an electron injecting and transporting layer. Otherwise as in Example 1, an organic EL device was fabricated.

A dc voltage was applied across the organic EL device. The device was found to produce light emission at a current density of 10 mA/cm² and a drive voltage of 7.1 volts to a luminance of 750 cd/m². The light emission had chromaticity coordinates (x, y) of (0.34, 0.42).

The device was continuously operated for light emission with a constant current of 50 mA/cm² conducted. It exhibited a luminance half-life period of more than 400 hours.

Example 20

When the hole injecting and transporting layer was formed by evaporation in Example 1, the compound to be evaporated along with TPD was changed to the compound of the following structure (I-33) and they were evaporated at a deposition rate ratio of 100:2, forming a hole injecting and transporting layer.

(CF 39)

I-33

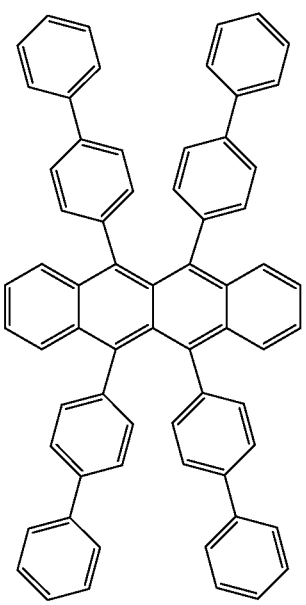

After the hole injecting layer was formed, the compound of the following structure (DPA) and 4,4'-bis(N-phenyl-N-1-naphthyl)aminostilbene having different carrier trapping capabilities were evaporated in a weight ratio of 100:2 at a deposition rate of 0.2 nm/sec to a thickness of 40 nm, forming a light emitting layer.

(CF 40)

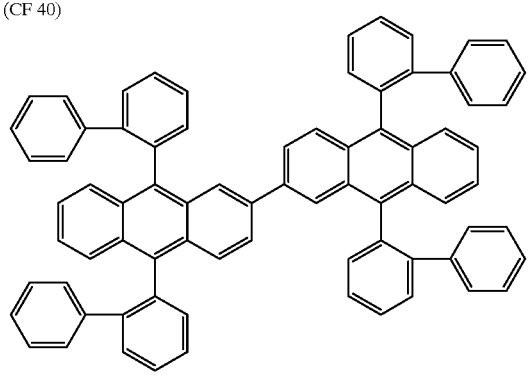

abbreviation: DPA
9, 9', 10, 10'-tetra(2-biphenylyl)-2, 2'-dianthracene (CF 41)

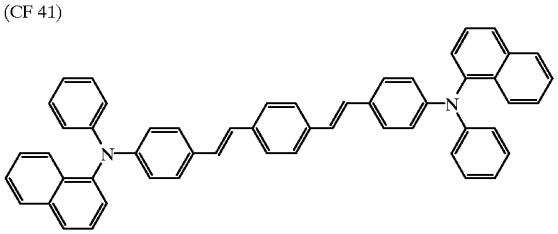

4, 4'-bis(N-phenyl-N-1-naphthyl)aminostilbene

With the vacuum kept, tris(8-quinolinolato)aluminum (Alq3) was evaporated at a deposition rate of 0.2 nm/sec to a thickness of 20 nm, forming an electron injecting and transporting layer. Otherwise as in Example 1, an organic EL device was fabricated.

A dc voltage was applied across the organic EL device. The device was found to produce light emission at a current density of 10 mA/cm² and a drive voltage of 7.3 volts to a luminance of 1,000 cd/m². The light emission had chromaticity coordinates (x, y) of (0.33, 0.41).

The device was continuously operated for light emission with a constant current of 50 mA/cm² conducted. It exhibited a luminance half-life period of more than 500 hours.

Example 21

When the hole injecting and transporting layer was formed by evaporation in Example 1, the compound to be evaporated along with TPD was changed to the compound of the following structure (I-223) and they were evaporated at a deposition rate ratio of 100:2, forming a hole injecting and transporting layer.

(CF 42)

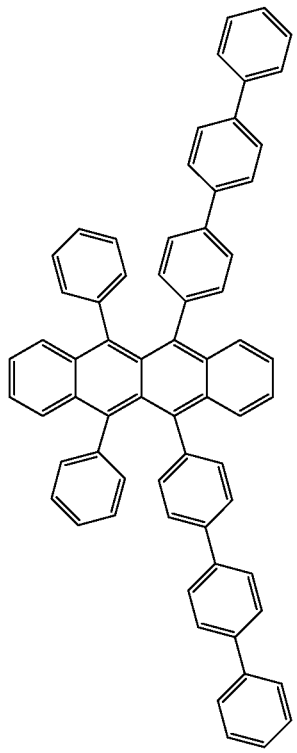

After the hole injecting layer was formed, the compound of the following structure (DPA) and 4,4'-bis(N-phenyl-N-1-naphthyl)aminostilbene having different carrier trapping capabilities were evaporated in a weight ratio of 100:2 at a deposition rate of 0.2 nm/sec to a thickness of 40 nm, forming a light emitting layer.

(CF 43)

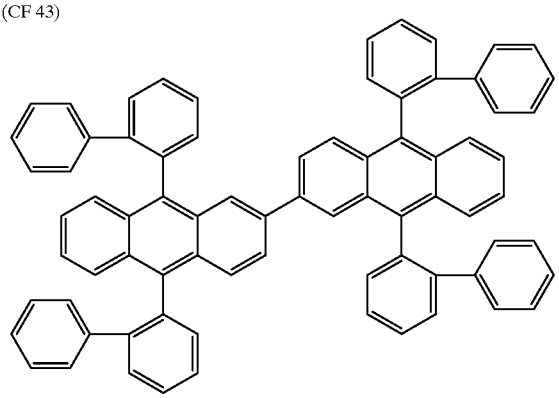

abbreviation: DPA
9, 9', 10, 10'-tetra(2-biphenylyl)-2, 2'-dianthracene (CF 44)

I-223

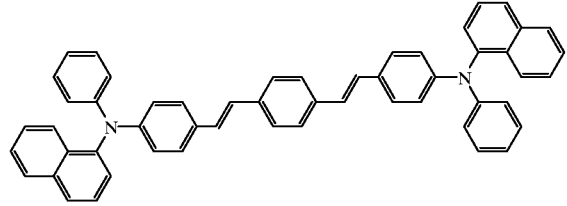

4, 4'-bis(N-phenyl-N-1-naphthyl)aminostilbene

With the vacuum kept, tris(8-quinolinolato)aluminum (Alq3) was evaporated at a deposition rate of 0.2 nm/sec to a thickness of 20 nm, forming an electron injecting and transporting layer. Otherwise as in Example 1, an organic EL device was fabricated.

A dc voltage was applied across the organic EL device. The device was found to produce light emission at a current density of 10 mA/cm$^2$ and a drive voltage of 7.3 volts to a luminance of 900 cd/m$^2$. The light emission had chromaticity coordinates (x, y) of (0.34, 0.41).

The device was continuously operated for light emission with a constant current of 50 mA/cm$^2$ conducted. It exhibited a luminance half-life period of more than 500 hours.

Comparative Example 1

An organic EL device was fabricated as in Example 1 except that the compound used along with Alq3 in the electron injecting and transporting/light emitting layer was changed to rubrene of the following structure.

(CF 45)

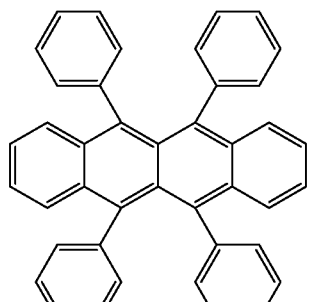

Comparison

A dc voltage was applied across the organic EL device. The device was found to produce light emission at a current density of 10 mA/cm$^2$ and a drive voltage of 9.0 volts to a luminance of 700 cd/m$^2$. The light emission had a maximum wavelength λmax of 558 nm and chromaticity coordinates (x, y) of (0.48, 0.51).

Measurement was similarly made using the same red filter as in Example 1, finding emission of red light at a luminance of 90 cd/m$^2$, a maximum wavelength λmax of 620 nm, and chromaticity coordinates (x, y) of (0.65, 0.35).

The device was continuously operated for light emission with a constant current of 50 mA/cm$^2$ conducted. It exhibited a luminance half-life period of less than 1,500 hours.

Comparative Example 2

An organic EL device was fabricated as in Example 1 except that the compound used along with Alq3 in the electron injecting and transporting/light emitting layer was changed to the compound of the following structure.

(CF 46)

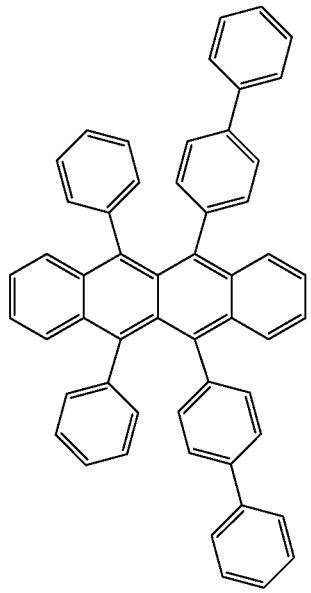

A dc voltage was applied across the organic EL device. The device was found to produce light emission at a current density of 10 mA/cm² and a drive voltage of 9.0 volts to a luminance of 800 cd/m². The light emission had a maximum wavelength λmax of 572 nm and chromaticity coordinates (x, y) of (0.53, 0.46).

Measurement was similarly made using the same red filter as in Example 1, finding emission of red light at a luminance of 153 cd/m², a maximum wavelength λmax of 620 nm, and chromaticity coordinates (x, y) of (0.66, 0.34).

The device was continuously operated for light emission with a constant current of 50 mA/cm² conducted. It exhibited a luminance half-life period of more than 2,500 hours.

Comparative Example 3

An organic EL device was fabricated as in Example 8 except that the compound used along with TPD in evaporating the hole injecting and transporting layer was changed to rubrene of the following structure.

(CF 47)

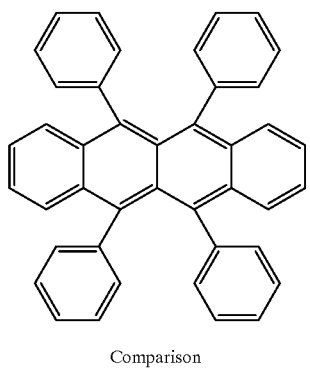

Comparison

A dc voltage was applied across the organic EL device. The device was found to produce light emission at a current density of 10 mA/cm² and a drive voltage of 5.46 volts to a luminance of 788 cd/m². The light emission had a maximum wavelength λmax of 553 nm and chromaticity coordinates (x, y) of (0.43, 0.54).

Measurement was similarly made using the same red filter as in Example 1, finding emission of red light at a luminance of 80 cd/m², a maximum wavelength λmax of 612 nm, and chromaticity coordinates (x, y) of (0.59, 0.39).

The device was continuously operated for light emission with a constant current of 50 mA/cm² conducted. It exhibited a luminance half-life period of less than 900 hours.

Comparative Example 4

An organic EL device was fabricated as in Example 8 except that the compound used along with TPD in evaporating the hole injecting and transporting layer was changed to the compound of the following structure.

(CF 48)

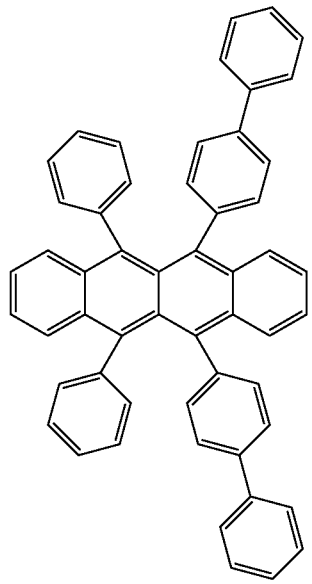

A dc voltage was applied across the organic EL device. The device was found to produce light emission at a current density of 10 mA/cm² and a drive voltage of 5.77 volts to a luminance of 974 cd/m². The light emission had a maximum wavelength λmax of 563 nm and chromaticity coordinates (x, y) of (0.44, 0.53).

Measurement was similarly made using the same red filter as in Example 1, finding emission of red light at a luminance of 140 cd/m$^2$, a maximum wavelength λmax of 615 nm, and chromaticity coordinates (x, y) of (0.61, 0.37).

The device was continuously operated for light emission with a constant current of 50 mA/cm$^2$ conducted. It exhibited a luminance half-life period of more than 1,700 hours.

Comparative Example 5

After the hole injecting layer was formed as in Example 1, rubrene and 9,9',10,10'-tetra(2-biphenylyl)-2,2'-dianthracene (DPA) of the following structure having different carrier trapping capabilities were evaporated in a weight ratio of 2:100 at a deposition rate of 0.2 nm/sec to a thickness of 40 nm, forming a light emitting layer.

(CF 49)

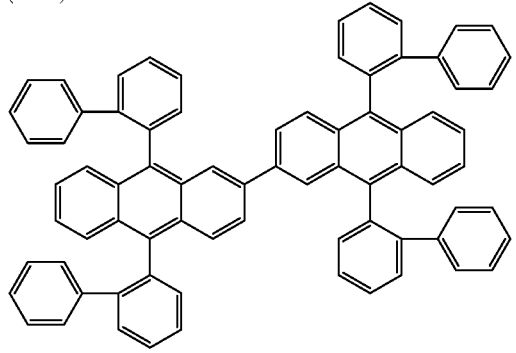

abbreviation: DPA
9,9',10,10'-tetra(2-biphenylyl)-2,2'-dianthracene

With the vacuum kept, tris(8-quinolinolato)aluminum (Alq3) was evaporated at a deposition rate of 0.2 nm/sec to a thickness of 15 nm, forming an electron injecting and transporting layer. Otherwise as in Example 1, an organic EL device was fabricated.

A dc voltage was applied across the organic EL device. The device was found to produce light emission at a current density of 10 mA/cm$^2$ and a drive voltage of 7.3 volts to a luminance of 850 cd/m$^2$. The light emission had a maximum wavelength λmax of 558 nm and chromaticity coordinates (x, y) of (0.48, 0.51).

Measurement was similarly made using the same red filter as in Example 1, finding emission of red light at a luminance of 160 cd/m$^2$, a maximum wavelength λmax of 620 nm, and chromaticity coordinates (x, y) of (0.65, 0.35).

The device was continuously operated for light emission with a constant current of 50 mA/cm$^2$ conducted. It exhibited a luminance half-life period of less than 500 hours.

Comparative Example 6

After the hole injecting layer was formed as in Example 1, the compound of the following structure and 9,9',10,10'-tetra(2-biphenylyl)-2,2'-dianthracene (DPA) having different carrier trapping capabilities were evaporated in a weight ratio of 2:100 at a deposition rate of 0.2 nm/sec to a thickness of 40 nm, forming a light emitting layer.

(CF 50)

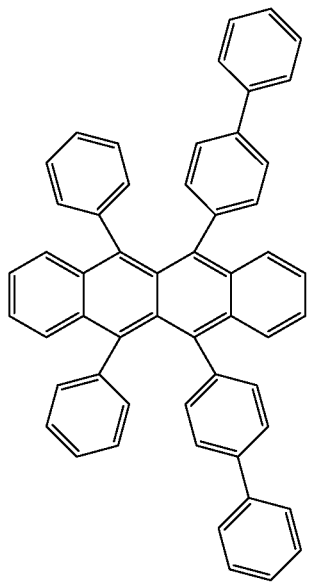

With the vacuum kept, tris(8-quinolinolato)aluminum (Alq3) was evaporated at a deposition rate of 0.2 nm/sec to a thickness of 15 nm, forming an electron injecting and transporting layer. Otherwise as in Example 1, an organic EL device was fabricated.

A dc voltage was applied across the organic EL device. The device was found to produce light emission at a current density of 10 mA/cm$^2$ and a drive voltage of 7.5 volts to a luminance of 1,200 cd/m$^2$. The light emission had a maximum wavelength λmax of 572 nm and chromaticity coordinates (x, y) of (0.54, 0.46).

Measurement was similarly made using the same red filter as in Example 1, finding emission of red light at a luminance of 230 cd/m$^2$, a maximum wavelength λmax of 620 nm, and chromaticity coordinates (x, y) of (0.66, 0.34).

The device was continuously operated for light emission with a constant current of 50 mA/cm$^2$ conducted. It exhibited a luminance half-life period of more than 1,000 hours.

Comparative Example 7

When the hole injecting and transporting layer was formed by evaporation in Example 1, the compound evaporated along with TPD was changed to rubrene of the following structure and they were evaporated at a deposition rate ratio of 100:2, forming a hole injecting and transporting layer.

(CF 51)

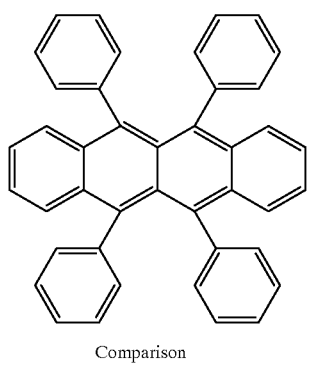

Comparison

After the hole injecting layer was formed, the compound of the following structure (DPA) and 4,4'-bis(N-phenyl-N-1-naphthyl)aminostilbene having different carrier trapping capabilities were evaporated in a weight ratio of 100:2 at a deposition rate of 0.2 nm/sec to a thickness of 40 nm, forming a light emitting layer.

(CF 52)

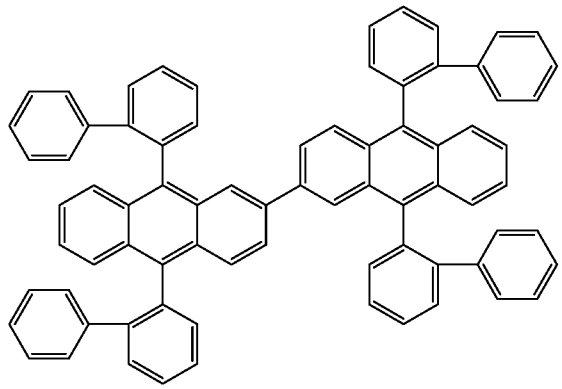

abbreviation: DPA
9,9',10,10'-tetra(2-biphenylyl)-2,2'-dianthracene (CF 53)

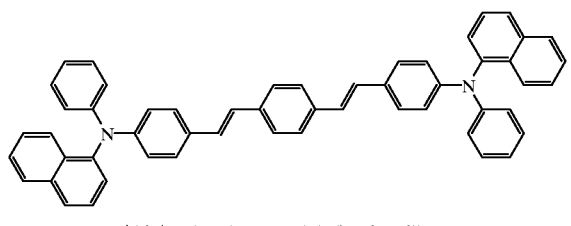

4,4'-bis(N-phenyl-N-1-naphthyl)aminostilbene

With the vacuum kept, tris(8-quinolinolato)aluminum (Alq3) was evaporated at a deposition rate of 0.2 nm/sec to a thickness of 20 nm, forming an electron injecting and transporting layer. Otherwise as in Example 1, an organic EL device was fabricated.

A dc voltage was applied across the organic EL device. The device was found to produce light emission at a current density of 10 mA/cm² and a drive voltage of 7.1 volts to a luminance of 750 cd/m². The light emission had chromaticity coordinates (x, y) of (0.34, 0.42).

The device was continuously operated for light emission with a constant current of 50 mA/cm² conducted. It exhibited a luminance half-life period of less than 200 hours.

BENEFITS OF THE INVENTION

There have been described compounds for organic EL devices and organic EL devices which produce light emission of satisfactory luminance, especially at long wavelength and are durable in that improved light emitting performance lasts for a long time.

What is claimed is:

1. A compound for organic electroluminescent devices, having a basic skeleton represented by the following formula (I):

(CF1)

formula (I)

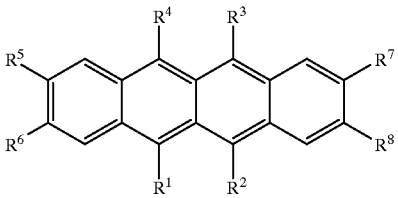

wherein $R^1$, $R^2$, $R^3$ and $R^4$ are each alkenyl or substituted aryl with the proviso that at least two of $R^1$ to $R^4$ are alkenyl, bicyclic aryl, or aryl substituted by aryl, amino, alkenyl, aryloxy or heterocyclic substituents, such that when the aryl substituents are monocyclic aryl, the monocyclic aryl groups are substituted and such that when the substituents of aryl are amino groups, at least two of $R^1$ to $R^4$ are substituted or unsubstituted aryl groups; and $R^5$, $R^6$, $R^7$ and $R^8$ are each hydrogen.

2. The compound for organic electroluminescent devices of claim 1, having a basic skeleton represented by the following formula (II):

(CF 2)

formula (II)

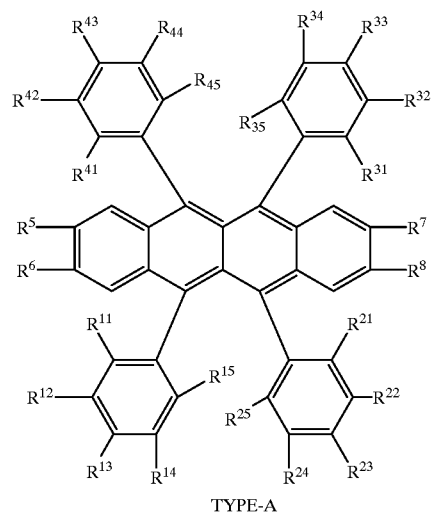

TYPE-A wherein each R group in sets of $R^{11}$ to $R^{15}$, $R^{21}$ to $R^{25}$, $R^{31}$ to $R^{35}$, and $R^{41}$ to $R^{45}$ is hydrogen or a substituted or unsubstituted alkyl, aryl, amino, heterocyclic or phenoxy group, the R groups in at least two sets have substituted or unsubstituted aryl, heterocyclic or aryloxy groups as substituents, or when the R groups are all hydrogen, at least two R groups in each of the sets of $R^{11}$ to $R^{15}$, $R^{21}$ to $R^{25}$, $R^{31}$ to $R^{35}$, and $R^{41}$ to $R^{45}$ form a fused ring.

3. The compound for organic electroluminescent devices of claim 1, having a basic skeleton represented by the following formula (III):

(CF 3)

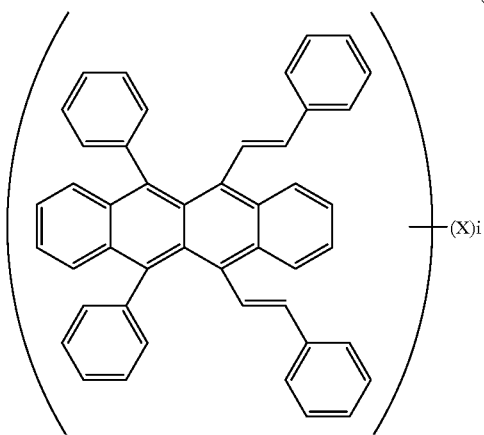

(III)

wherein X represents a substituent as defined for the substituents on $R^1$, $R^2$, $R^3$ and $R^4$, and i is an integer of 0 to 20.

4. An organic electroluminescent device comprising a hole injecting electrode, an electron injecting electrode, and an organic layer disposed between the electrodes and including at least a light emitting layer, wherein
said light emitting layer contains the compound of claim 1.

5. The organic electroluminescent device of claim 4 wherein said light emitting layer further contains an electron injecting and transporting compound and/or a hole injecting and transporting compound.

6. The organic electroluminescent device of claim 4 wherein said light emitting layer contains at least two compounds.

7. The organic electroluminescent device of claim 4 wherein said light emitting layer contains at least two dopants, the content of the dopants combined being up to 30% by weight based on a host material.

8. The organic electroluminescent device of claim 4 wherein the overall content of the compound of claim 1 in said light emitting layer is up to 30% by weight based on a host material.

9. The organic electroluminescent device of claim 7 wherein said light emitting layer contains at least two compounds having different carrier trapping capabilities.

10. The organic electroluminescent device of claim 7 wherein said light emitting layer contains at least a compound having a hole trapping capability and a compound having an electron trapping capability.

11. The organic electroluminescent device of claim 4 wherein at least two light emitting layers are included, and said light emitting layers contain dopants having different carrier trapping capabilities.

12. The organic electroluminescent device of claim 4 wherein at least two light emitting layers are included, at least one layer of said light emitting layers contains a dopant having a hole trapping capability, and at least one other layer of said light emitting layers contains a dopant having an electron trapping capability.

13. An organic electroluminescent device comprising a hole injecting electrode, an electron injecting electrode, and an organic layer disposed between the electrodes and including at least a light emitting layer, wherein
said light emitting layer contains at least two organic electroluminescent device-forming compounds having different carrier trapping capabilities, each said compound having a basic skeleton represented by the following formula (IV):

(CF 4)

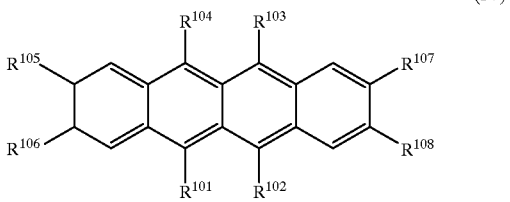

(IV)

wherein $R^{101}$, $R^{102}$, $R^{103}$, and $R^{104}$ each are hydrogen or a substituted or unsubstituted aryl or alkenyl group, excluding the case where at least three R's are hydrogen atoms; $R^{105}$, $R^{106}$, $R^{107}$, and $R^{108}$ each are hydrogen or a substituted or unsubstituted aryl or alkenyl group; at least two of $R^{101}$ to $R^{104}$ are aryl groups which are at least bicyclic or alkenyl groups, or have alkyl, aryl, amino, alkenyl, aryloxy or heterocyclic groups as substituents.

* * * * *